(12) United States Patent
Bachelet et al.

(10) Patent No.: US 10,316,320 B2
(45) Date of Patent: Jun. 11, 2019

(54) SYSTEMS COMPRISING NON-IMMUNOGENIC AND NUCLEASE RESISTANT NUCLEIC ACID ORIGAMI DEVICES FOR MOLECULAR COMPUTATION

(71) Applicant: BAR-ILAN UNIVERSITY, Ramat Gan (IL)

(72) Inventors: Ido Bachelet, Modiin (IL); Almogit Abu-Horowitz, Hertzeliya (IL); Eldad Ben-Ishay, Shoham (IL); Yaniv Amir, Yehud (IL); Joel De Beer, Zollikon (CH); Shmulik Ittah, Jerusalem (IL)

(73) Assignee: BAR ILAN UNIVERSITY, Ramat Gan (IL)

( * ) Notice: Subject to any disclaimer, the term of this patent is extended or adjusted under 35 U.S.C. 154(b) by 648 days.

(21) Appl. No.: 14/785,201

(22) PCT Filed: Apr. 13, 2014

(86) PCT No.: PCT/IL2014/050357
§ 371 (c)(1),
(2) Date: Oct. 16, 2015

(87) PCT Pub. No.: WO2014/170899
PCT Pub. Date: Oct. 23, 2014

(65) Prior Publication Data
US 2016/0083730 A1    Mar. 24, 2016

Related U.S. Application Data

(60) Provisional application No. 61/813,417, filed on Apr. 18, 2013.

(51) Int. Cl.
*C12N 15/115* (2010.01)
*A61K 47/69* (2017.01)
*B82Y 5/00* (2011.01)

(52) U.S. Cl.
CPC ........ *C12N 15/115* (2013.01); *A61K 47/6901* (2017.08); *A61K 47/6923* (2017.08);
(Continued)

(58) Field of Classification Search
None
See application file for complete search history.

(56) References Cited

U.S. PATENT DOCUMENTS

2007/0117109 A1* 5/2007 Rothemund ............ C12P 19/34
435/6.12

FOREIGN PATENT DOCUMENTS

| WO | 2004011680 A1 | 2/2004 |
| WO | 2008040095 A1 | 4/2008 |
| WO | 2012061719 A3 | 5/2012 |

OTHER PUBLICATIONS

ISR and WO as issued in PCT/IL2014/050357 dated Aug. 3, 2014.
(Continued)

*Primary Examiner* — Robert T. Crow
(74) *Attorney, Agent, or Firm* — Symbus Law Group, LLC; Clifford D. Hyra

(57) ABSTRACT

Systems acting as logic gates and systems exhibiting quorum sensing are provided, wherein said systems comprise at least one effector nucleic acid origami device, at least one regulator nucleic acid origami device, at least one input and at least one output, and the nucleic acid origami devices are non-immunogenic and/or resistant to nucleases.

21 Claims, 15 Drawing Sheets

Specification includes a Sequence Listing.

(52) U.S. Cl.
CPC ............. *B82Y 5/00* (2013.01); *C12N 2310/16* (2013.01); *C12N 2310/3519* (2013.01)

(56) References Cited

OTHER PUBLICATIONS

Douglas SM et al. A logic-gated nanorobot for targeted transport of molecular payloads Science Feb. 17, 2012.
Schuller, Verena J., et al Cellular immunostimulation by CpG-sequence-coated DNA origami structures. Dec. 27, 2011.
Tuite E, et al. Effects of Minor and Major Groove Binding Drugs and Intercalators on the DNA Association of Minor Groove Binding Proteins RecA and Deoxyribonuclease I Decected by Flow Linear Dichroism Jan. 15, 1997.
Amir Y et al., Universal computing by DNA origami robots in a living animal. May 9, 2014.
Smith, David, et al. Nucleic acid nanostructures for biomedical applications. Jan. 31, 2013.

\* cited by examiner

SEQUENCE LISTING

<160> NUMBER OF SEQ ID NOS: 283

<210> SEQ ID NO 1
<211> LENGTH: 6
<212> TYPE: PRT
<213> ORGANISM: artificial sequence
<220> FEATURE:
<223> OTHER INFORMATION: synthetic

<400> SEQUENCE: 1

Lys Ile Glu Ala Arg Cys
1               5

<210> SEQ ID NO 2
<211> LENGTH: 12
<212> TYPE: PRT
<213> ORGANISM: artificial sequence
<220> FEATURE:
<223> OTHER INFORMATION: synthetic

<400> SEQUENCE: 2

Gly Arg Lys Lys Arg Arg Gln Arg Arg Arg Pro Gln
1               5                   10

<210> SEQ ID NO 3
<211> LENGTH: 9
<212> TYPE: PRT
<213> ORGANISM: artificial sequence
<220> FEATURE:
<223> OTHER INFORMATION: synthetic

<400> SEQUENCE: 3

Lys Pro Leu Gly Met Trp Ser Arg Cys
1               5

<210> SEQ ID NO 4
<211> LENGTH: 7249
<212> TYPE: DNA
<213> ORGANISM: Artificial Sequence
<220> FEATURE:
<223> OTHER INFORMATION: synthetic

<400> SEQUENCE: 4
aatgctacta ctattagtag aattgatgcc accttttcag ctcgcgcccc aaatgaaaat      60
atagctaaac aggttattga ccatttgcga aatgtatcta atggtcaaac taaatctact     120
cgttcgcaga attgggaatc aactgttata tggaatgaaa cttccagaca ccgtacttta     180
gttgcatatt taaaacatgt tgagctacag cattatattc agcaattaag ctctaagcca     240
tccgcaaaaa tgacctctta tcaaaaggag caattaaagg tactctctaa tcctgacctg     300
ttggagtttg cttccggtct ggttcgcttt gaagctcgaa ttaaaacgcg atatttgaag     360
tctttcgggc ttcctcttaa tcttttttgat gcaatccgct ttgcttctga ctataatagt     420
cagggtaaag acctgatttt tgatttatgg tcattctcgt tttctgaact gtttaaagca     480
tttgaggggg attcaatgaa tatttatgac gattccgcag tattggacgc tatccagtct     540
aaacatttta ctattacccc ctctggcaaa acttcttttg caaaagcctc tcgctatttt     600
ggtttttatc gtcgtctggt aaacgagggt tatgatagtg ttgctcttac tatgcctcgt     660
aattcctttt ggcgttatgt atctgcatta gttgaatgtg gtattcctaa atctcaactg     720

```
atgaatcttt ctacctgtaa taatgttgtt ccgttagttc gttttattaa cgtagatttt      780
tcttcccaac gtcctgactg gtataatgag ccagttctta aaatcgcata aggtaattca      840
caatgattaa agttgaaatt aaaccatctc aagcccaatt tactactcgt tctggtgttt      900
ctcgtcaggg caagccttat tcactgaatg agcagctttg ttacgttgat ttgggtaatg      960
aatatccggt tcttgtcaag attactcttg atgaaggtca gccagcctat gcgcctggtc     1020
tgtacaccgt tcatctgtcc tctttcaaag ttggtcagtt cggttccctt atgattgacc     1080
gtctgcgcct cgttccggct aagtaacatg gagcaggtcg cggatttcga cacaatttat     1140
caggcgatga tacaaatctc cgttgtactt tgtttcgcgc ttggtataat cgctgggggt     1200
caaagatgag tgtttagtg tattctttg cctctttcgt tttaggttgg tgccttcgta       1260
gtggcattac gtattttacc cgtttaatgg aaacttcctc atgaaaaagt ctttagtcct     1320
caaagcctct gtagccgttg ctaccctcgt tccgatgctg tctttcgctg ctgagggtga     1380
cgatcccgca aaagcggcct ttaactccct gcaagcctca gcgaccgaat atatcggtta     1440
tgcgtgggcg atggttgttg tcattgtcgg cgcaactatc ggtatcaagc tgtttaagaa     1500
attcacctcg aaagcaagct gataaaccga tacaattaaa ggctcctttt ggagcctttt     1560
ttttggagat tttcaacgtg aaaaaattat tattcgcaat cctttagtt gttcctttct      1620 attctcactc cgctgaaact gttgaaagtt gtttagcaaa atcccataca gaaaattcat     1680
ttactaacgt ctggaaagac gacaaaactt tagatcgtta cgctaactat gagggctgtc     1740
tgtggaatgc tacaggcgtt gtagtttgta ctggtgacga aactcagtgt tacggtacat     1800
gggttcctat tgggcttgct atccctgaaa atgagggtgg tggctctgag ggtggcggtt     1860
ctgagggtgg cggttctgag ggtggcggta ctaaacctcc tgagtacggt gatacaccta     1920
ttccgggcta ctttatatc aaccctctcg acggcactta tccgcctggt actgagcaaa      1980
accccgctaa tcctaatcct tctcttgagg agtctcagcc tcttaatact ttcatgtttc     2040
agaataatag gttccgaaat aggcaggggg cattaactgt ttatacgggc actgttactc     2100
aaggcactga ccccgttaaa acttattacc agtacactcc tgtatcatca aaagccatgt     2160
atgacgctta ctggaacggt aaattcagag actgcgcttt ccattctggc tttaatgagg     2220
atttatttgt ttgtgaatat caaggccaat cgtctgacct gcctcaacct cctgtcaatg     2280
ctggcggcgg ctctggtggt ggttctggtg cggctctga gggtggtggc tctgagggtg      2340
gcggttctga gggtggcggc tctgaggag gcggttccgg tggtggctct ggttccggtg      2400
attttgatta tgaaaagatg gcaaacgcta ataaggggc tatgaccgaa atgccgatg       2460 aaaacgcgct acagtctgac gctaaaggca aacttgattc tgtcgctact gattacggtg     2520
ctgctatcga tggtttcatt ggtgacgttt ccggccttgc taatggtaat ggtgctactg     2580
gtgattttgc tggctctaat tcccaaatgg ctcaagtcgg tgacggtgat aattcacctt     2640
taatgaataa tttccgtcaa tatttacctt ccctccctca atcggttgaa tgtcgccctt     2700
ttgtctttgg cgctggtaaa ccatatgaat tttctattga ttgtgacaaa ataaacttat     2760
tccgtggtgt ctttgcgttt cttttatatg ttgccacctt tatgtatgta ttttctacgt     2820
ttgctaacat actgcgtaat aaggagtctt aatcatgcca gttcttttgg gtattccgtt     2880
attattgcgt ttcctcggtt tccttctggt aactttgttc ggctatctgc ttacttttct     2940 taaaagggc ttcggtaaga tagctattgc tatttcattg tttcttgctc ttattattgg      3000
gcttaactca attcttgtgg gttatctctc tgatattagc gctcaattac cctctgactt     3060
```

```
tgttcagggt gttcagttaa ttctcccgtc taatgcgctt ccctgttttt atgttattct    3120
ctctgtaaag gctgctattt tcattttga cgttaaacaa aaatcgtttt cttatttgga    3180
ttgggataaa taatatggct gtttattttg taactggcaa attaggctct ggaaagacgc    3240
tcgttagcgt tggtaagatt caggataaaa ttgtagctgg gtgcaaaata gcaactaatc    3300
ttgatttaag gcttcaaaac ctcccgcaag tcgggaggtt cgctaaaacg cctcgcgttc    3360
ttagaatacc ggataagcct tctatatctg atttgcttgc tattgggcgc ggtaatgatt    3420
cctacgatga aaataaaaac ggcttgcttg ttctcgatga gtgcggtact tggtttaata    3480
cccgttcttg gaatgataag gaaagacagc cgattattga ttggtttcta catgctcgta    3540
aattaggatg ggatattatt tttcttgttc aggacttatc tattgttgat aaacaggcgc    3600
gttctgcatt agctgaacat gttgtttatt gtcgtcgtct ggacagaatt actttacctt    3660
ttgtcggtac tttatattct cttattactg gctcgaaaat gcctctgcct aaattacatg    3720
ttggcgttgt taaatatggc gattctcaat taagccctac tgttgagcgt tggctttata    3780
ctggtaagaa tttgtataac gcatatgata ctaaacaggc tttttctagt aattatgatt    3840
ccggtgttta tcttattta acgccttatt tatcacacgg tcggtatttc aaaccattaa    3900
atttaggtca gaagatgaaa ttaactaaaa tatatttgaa aaagttttct cgcgttcttt    3960
gtcttgcgat tggatttgca tcagcattta catatagtta tataacccaa cctaagccgg    4020
aggttaaaaa ggtagtctct cagacctatg attttgataa attcactatt gactcttctc    4080
agcgtcttaa tctaagctat cgctatgttt tcaaggattc taagggaaaa ttaattaata    4140
gcgacgattt acagaagcaa ggttattcac tcacatatat tgatttatgt actgtttcca    4200
ttaaaaaagg taattcaaat gaaattgtta aatgtaatta attttgtttt cttgatgttt    4260
gtttcatcat cttcttttgc tcaggtaatt gaaatgaata attcgcctct gcgcgatttt    4320
gtaacttggt attcaaagca atcaggcgaa tccgttattg tttctcccga tgtaaaaggt    4380
actgttactg tatattcatc tgacgttaaa cctgaaaatc tacgcaattt ctttatttct    4440
gttttacgtg caaataattt tgatatggta ggttctaacc cttccattat tcagaagtat    4500
aatccaaaca atcaggatta tattgatgaa ttgccatcat ctgataatca ggaatatgat    4560
gataattccg ctccttctgg tggtttcttt gttccgcaaa atgataatgt tactcaaact    4620
tttaaaatta ataacgttcg ggcaaaggat ttaatacgag ttgtcgaatt gtttgtaaag    4680
tctaatactt ctaaatcctc aaatgtatta tctattgacg gctctaatct attagttgtt    4740
agtgctccta aagatatttt agataacctt cctcaattcc tttcaactgt tgatttgcca    4800
actgaccaga tattgattga gggtttgata tttgaggttc agcaaggtga tgctttagat    4860
ttttcatttg ctgctggctc tcagcgtggc actgttgcag gcggtgttaa tactgaccgc    4920
ctcacctctg ttttatcttc tgctggtggt tcgttcggta tttttaatgg cgatgtttta    4980
gggctatcag ttcgcgcatt aaagactaat agccattcaa aaatattgtc tgtgccacgt    5040
attcttacgc tttcaggtca gaagggttct atctctgttg gccagaatgt ccctttat   5100 actggtcgtg tgactggtga atctgccaat gtaaataatc catttcagac gattgagcgt    5160
caaaatgtag gtatttccat gagcgttttt cctgttgcaa tggctggcgg taatattgtt    5220
ctggatatta ccagcaaggc cgatagtttg agttcttcta ctcaggcaag tgatgttatt    5280
actaatcaaa gaagtattgc tacaacggtt aatttgcgtg atggacagac tcttttactc    5340
ggtggcctca ctgattataa aaacacttct caggattctg gcgtaccgtt cctgtctaaa    5400
atccctttaa tcggcctcct gtttagctcc cgctctgatt ctaacgagga aagcacgtta    5460
```

```
tacgtgctcg tcaaagcaac catagtacgc gccctgtagc ggcgcattaa gcgcggcggg    5520
tgtggtggtt acgcgcagcg tgaccgctac acttgccagc gccctagcgc ccgctccttt    5580
cgctttcttc ccttcctttc tcgccacgtt cgccggcttt ccccgtcaag ctctaaatcg    5640
ggggctccct ttagggttcc gatttagtgc tttacggcac ctcgacccca aaaaacttga    5700
tttgggtgat ggttcacgta gtgggccatc gccctgatag acggttttc gccctttgac     5760 gttgagtcc acgttcttta atagtggact cttgttccaa actggaacaa cactcaaccc      5820
tatctcgggc tattctttg atttataagg gattttgccg atttcggaac caccatcaaa     5880
caggattttc gcctgctggg gcaaaccagc gtggaccgct tgctgcaact ctctcagggc    5940
caggcggtga agggcaatca gctgttgccc gtctcactgg tgaaaagaaa aaccaccctg    6000
gcgcccaata cgcaaaccgc ctctccccgc gcgttggccg attcattaat gcagctggca    6060
cgacaggttt cccgactgga aagcgggcag tgagcgcaac gcaattaatg tgagttagct    6120
cactcattag gcaccccagg ctttacactt tatgcttccg gctcgtatgt tgtgtggaat    6180
tgtgagcgga taacaatttc acacaggaaa cagctatgac catgattacg aattcgagct    6240
cggtacccgg ggatcctcta gagtcgacct gcaggcatgc aagcttggca ctggccgtcg    6300
ttttacaacg tcgtgactgg gaaaaccctg gcgttaccca acttaatcgc cttgcagcac    6360 atccccctt cgccagctgg cgtaatagcg aagaggcccg caccgatcgc ccttcccaac     6420
agttgcgcag cctgaatggc gaatggcgct ttgcctggtt tccggcacca gaagcggtgc    6480
cggaaagctg gctggagtgc gatcttcctg aggccgatac tgtcgtcgtc ccctcaaact    6540
ggcagatgca cggttacgat gcgcccatct acaccaacgt gacctatccc attacggtca    6600
atccgccgtt tgttcccacg gagaatccga cgggttgtta ctcgctcaca tttaatgttg    6660
atgaaagctg gctacaggaa ggccagacgc gaattatttt tgatggcgtt cctattggtt    6720
aaaaaatgag ctgatttaac aaaaatttaa tgcgaatttt aacaaaatat taacgtttac    6780
aatttaaata tttgcttata caatcttcct gttttggggg cttttctgat tatcaaccgg    6840
ggtacatatg attgacatgc tagttttacg attaccgttc atcgattctc ttgtttgctc    6900
cagactctca ggcaatgacc tgatagcctt tgtagatctc tcaaaaatag ctaccctctc    6960
cggcattaat ttatcagcta gaacggttga atatcatatt gatggtgatt tgactgtctc    7020
cggcctttct caccctttg aatctttacc tacacattac tcaggcattg catttaaaat    7080
atatgagggt tctaaaaatt tttatccttg cgttgaaata aaggcttctc ccgcaaaagt    7140
attacagggt cataatgttt ttggtacaac cgatttagct ttatgctctg aggctttatt    7200
gcttaatttt gctaattctt tgccttgcct gtatgattta ttggatgtt                 7249
```

<210> SEQ ID NO 5
<211> LENGTH: 35
<212> TYPE: DNA
<213> ORGANISM: artificial sequence
<220> FEATURE:
<223> OTHER INFORMATION: synthetic

<400> SEQUENCE: 5
aaaaaccaaa ccctcgttgt gaatatggtt tggtc                               35

<210> SEQ ID NO 6
<211> LENGTH: 42
<212> TYPE: DNA
<213> ORGANISM: artificial sequence
<220> FEATURE:

<223> OTHER INFORMATION: synthetic

<400> SEQUENCE: 6
ggaagaagtg tagcggtcac gttataatca gcagactgat ag          42

<210> SEQ ID NO 7
<211> LENGTH: 24
<212> TYPE: DNA
<213> ORGANISM: artificial sequence
<220> FEATURE:
<223> OTHER INFORMATION: synthetic

<400> SEQUENCE: 7
tacgatatag ataatcgaac aaca          24

<210> SEQ ID NO 8
<211> LENGTH: 28
<212> TYPE: DNA
<213> ORGANISM: artificial sequence
<220> FEATURE:
<223> OTHER INFORMATION: synthetic

<400> SEQUENCE: 8
cttttgctta agcaataaag cgagtaga          28

<210> SEQ ID NO 9
<211> LENGTH: 32
<212> TYPE: DNA
<213> ORGANISM: artificial sequence
<220> FEATURE:
<223> OTHER INFORMATION: synthetic

<400> SEQUENCE: 9
gtctgaaata acatcggtac ggccgcgcac gg          32

<210> SEQ ID NO 10
<211> LENGTH: 31
<212> TYPE: DNA
<213> ORGANISM: artificial sequence
<220> FEATURE:
<223> OTHER INFORMATION: synthetic

<400> SEQUENCE: 10
ggaagagcca acagcttgc agggaaccta a          31

<210> SEQ ID NO 11
<211> LENGTH: 28
<212> TYPE: DNA
<213> ORGANISM: artificial sequence
<220> FEATURE:
<223> OTHER INFORMATION: synthetic

<400> SEQUENCE: 11
aaaatcaccg gaagcaaact ctgtagct          28

<210> SEQ ID NO 12
<211> LENGTH: 39
<212> TYPE: DNA
<213> ORGANISM: artificial sequence
<220> FEATURE:
<223> OTHER INFORMATION: synthetic

<400> SEQUENCE: 12
cctacatgaa gaactaaagg gcagggcgga gccccgggc          39

<210> SEQ ID NO 13
<211> LENGTH: 28
<212> TYPE: DNA
<213> ORGANISM: artificial sequence
<220> FEATURE:
<223> OTHER INFORMATION: synthetic

<400> SEQUENCE: 13
catgtaaaaa ggtaaagtaa taagaacg                              28

<210> SEQ ID NO 14
<211> LENGTH: 42
<212> TYPE: DNA
<213> ORGANISM: artificial sequence
<220> FEATURE:
<223> OTHER INFORMATION: synthetic

<400> SEQUENCE: 14
attaaatcag gtcattgcct gtctagctga taaattgtaa ta              42

<210> SEQ ID NO 15
<211> LENGTH: 24
<212> TYPE: DNA
<213> ORGANISM: artificial sequence
<220> FEATURE:
<223> OTHER INFORMATION: synthetic

<400> SEQUENCE: 15
atagtcgtct tttgcggtaa tgcc                                  24

<210> SEQ ID NO 16
<211> LENGTH: 31
<212> TYPE: DNA
<213> ORGANISM: artificial sequence
<220> FEATURE:
<223> OTHER INFORMATION: synthetic

<400> SEQUENCE: 16
agtcatggtc atagctgaac tcactgccag t                          31

<210> SEQ ID NO 17
<211> LENGTH: 31
<212> TYPE: DNA
<213> ORGANISM: artificial sequence
<220> FEATURE:
<223> OTHER INFORMATION: synthetic

<400> SEQUENCE: 17
aactattgac ggaaatttga gggaatataa a                          31

<210> SEQ ID NO 18
<211> LENGTH: 39
<212> TYPE: DNA
<213> ORGANISM: artificial sequence
<220> FEATURE:
<223> OTHER INFORMATION: synthetic

<400> SEQUENCE: 18
atcgcgtctg gaagtttcat tccatataga aagaccatc                  39

<210> SEQ ID NO 19
<211> LENGTH: 42
<212> TYPE: DNA
<213> ORGANISM: artificial sequence
<220> FEATURE:
<223> OTHER INFORMATION: synthetic

<400> SEQUENCE: 19
aaatattgaa cggtaatcgt agccggagac agtcataaaa at                              42

<210> SEQ ID NO 20
<211> LENGTH: 38
<212> TYPE: DNA
<213> ORGANISM: artificial sequence
<220> FEATURE:
<223> OTHER INFORMATION: synthetic

<400> SEQUENCE: 20
gtctttacag gattagtatt ctaacgagca tagaacgc                                   38

<210> SEQ ID NO 21
<211> LENGTH: 28
<212> TYPE: DNA
<213> ORGANISM: artificial sequence
<220> FEATURE:
<223> OTHER INFORMATION: synthetic

<400> SEQUENCE: 21
gcaccgcgac gacgctaatg aacagctg                                              28

<210> SEQ ID NO 22
<211> LENGTH: 24
<212> TYPE: DNA
<213> ORGANISM: artificial sequence
<220> FEATURE:
<223> OTHER INFORMATION: synthetic

<400> SEQUENCE: 22
aacttcattt tagaatcgca aatc                                                  24

<210> SEQ ID NO 23
<211> LENGTH: 38
<212> TYPE: DNA
<213> ORGANISM: artificial sequence
<220> FEATURE:
<223> OTHER INFORMATION: synthetic

<400> SEQUENCE: 23
cgtagagtct tgttaaggc cttcgttttc ctaccgag                                    38

<210> SEQ ID NO 24
<211> LENGTH: 28
<212> TYPE: DNA
<213> ORGANISM: artificial sequence
<220> FEATURE:
<223> OTHER INFORMATION: synthetic

<400> SEQUENCE: 24
ccaatcaaag gcttatccgg ttgctatt                                              28

<210> SEQ ID NO 25
<211> LENGTH: 28
<212> TYPE: DNA
<213> ORGANISM: artificial sequence
<220> FEATURE:
<223> OTHER INFORMATION: synthetic

<400> SEQUENCE: 25
agaggcgata taatcctgat tcatcata                                              28

<210> SEQ ID NO 26
<211> LENGTH: 32

```
<212> TYPE: DNA
<213> ORGANISM: artificial sequence
<220> FEATURE:
<223> OTHER INFORMATION: synthetic

<400> SEQUENCE: 26
ccgtaatccc tgaataataa cggaatacta cg                                32

<210> SEQ ID NO 27
<211> LENGTH: 25
<212> TYPE: DNA
<213> ORGANISM: artificial sequence
<220> FEATURE:
<223> OTHER INFORMATION: synthetic

<400> SEQUENCE: 27
aaatggtata cagggcaagg aaatc                                        25

<210> SEQ ID NO 28
<211> LENGTH: 24
<212> TYPE: DNA
<213> ORGANISM: artificial sequence
<220> FEATURE:
<223> OTHER INFORMATION: synthetic

<400> SEQUENCE: 28
tcctcatcgt aaccaagacc gaca                                         24

<210> SEQ ID NO 29
<211> LENGTH: 35
<212> TYPE: DNA
<213> ORGANISM: artificial sequence
<220> FEATURE:
<223> OTHER INFORMATION: synthetic

<400> SEQUENCE: 29
cattatctgg ctttagggaa ttatgtttgg attac                             35

<210> SEQ ID NO 30
<211> LENGTH: 24
<212> TYPE: DNA
<213> ORGANISM: artificial sequence
<220> FEATURE:
<223> OTHER INFORMATION: synthetic

<400> SEQUENCE: 30
acccgcccaa tcattcctct gtcc                                         24

<210> SEQ ID NO 31
<211> LENGTH: 39
<212> TYPE: DNA
<213> ORGANISM: artificial sequence
<220> FEATURE:
<223> OTHER INFORMATION: synthetic

<400> SEQUENCE: 31
cgaccagtca cgcagccacc gctggcaaag cgaaagaac                         39

<210> SEQ ID NO 32
<211> LENGTH: 32
<212> TYPE: DNA
<213> ORGANISM: artificial sequence
<220> FEATURE:
<223> OTHER INFORMATION: synthetic

<400> SEQUENCE: 32
```
ctaaaggcgt actatggttg caacaggaga ga                                    32

<210> SEQ ID NO 33
<211> LENGTH: 32
<212> TYPE: DNA
<213> ORGANISM: artificial sequence
<220> FEATURE:
<223> OTHER INFORMATION: synthetic

<400> SEQUENCE: 33
ttggcaggca atacagtgtt tctgcgcggg cg                                    32

<210> SEQ ID NO 34
<211> LENGTH: 42
<212> TYPE: DNA
<213> ORGANISM: artificial sequence
<220> FEATURE:
<223> OTHER INFORMATION: synthetic

<400> SEQUENCE: 34
tatacaggaa ataaagaaat tttgcccgaa cgttaagact tt                         42

<210> SEQ ID NO 35
<211> LENGTH: 42
<212> TYPE: DNA
<213> ORGANISM: artificial sequence
<220> FEATURE:
<223> OTHER INFORMATION: synthetic

<400> SEQUENCE: 35
aagtatagta taaacagtta actgaattta ccgttgagcc ac                         42

<210> SEQ ID NO 36
<211> LENGTH: 28
<212> TYPE: DNA
<213> ORGANISM: artificial sequence
<220> FEATURE:
<223> OTHER INFORMATION: synthetic

<400> SEQUENCE: 36
acattcagat agcgtccaat attcagaa                                         28

<210> SEQ ID NO 37
<211> LENGTH: 35
<212> TYPE: DNA
<213> ORGANISM: artificial sequence
<220> FEATURE:
<223> OTHER INFORMATION: synthetic

<400> SEQUENCE: 37
aaacatcttt accctcacca gtaaagtgcc cgccc                                 35

<210> SEQ ID NO 38
<211> LENGTH: 28
<212> TYPE: DNA
<213> ORGANISM: artificial sequence
<220> FEATURE:
<223> OTHER INFORMATION: synthetic

<400> SEQUENCE: 38
gagatgaccc taatgccagg ctattttt                                         28

<210> SEQ ID NO 39
<211> LENGTH: 32
<212> TYPE: DNA
<213> ORGANISM: artificial sequence

```
<220> FEATURE:
<223> OTHER INFORMATION: synthetic

<400> SEQUENCE: 39
tcctgaattt tttgtttaac gatcagagcg ga                                32

<210> SEQ ID NO 40
<211> LENGTH: 31
<212> TYPE: DNA
<213> ORGANISM: artificial sequence
<220> FEATURE:
<223> OTHER INFORMATION: synthetic

<400> SEQUENCE: 40
gccgaaaaat ctaaagccaa tcaaggaaat a                                 31

<210> SEQ ID NO 41
<211> LENGTH: 49
<212> TYPE: DNA
<213> ORGANISM: artificial sequence
<220> FEATURE:
<223> OTHER INFORMATION: synthetic

<400> SEQUENCE: 41
agcgtagcgc gttttcacaa aatctatgtt agcaaacgaa cgcaacaaa              49

<210> SEQ ID NO 42
<211> LENGTH: 28
<212> TYPE: DNA
<213> ORGANISM: artificial sequence
<220> FEATURE:
<223> OTHER INFORMATION: synthetic

<400> SEQUENCE: 42
accaatcgat taaattgcgc cattatta                                     28

<210> SEQ ID NO 43
<211> LENGTH: 32
<212> TYPE: DNA
<213> ORGANISM: artificial sequence
<220> FEATURE:
<223> OTHER INFORMATION: synthetic

<400> SEQUENCE: 43
atcttactta ttttcagcgc cgacaggatt ca                                32

<210> SEQ ID NO 44
<211> LENGTH: 21
<212> TYPE: DNA
<213> ORGANISM: artificial sequence
<220> FEATURE:
<223> OTHER INFORMATION: synthetic

<400> SEQUENCE: 44
ccctaaaaga acccagtcac a                                            21

<210> SEQ ID NO 45
<211> LENGTH: 35
<212> TYPE: DNA
<213> ORGANISM: artificial sequence
<220> FEATURE:
<223> OTHER INFORMATION: synthetic

<400> SEQUENCE: 45
ggaagggcga aaatcgggtt tttcgcgttg ctcgt                             35
```

<210> SEQ ID NO 46
<211> LENGTH: 35
<212> TYPE: DNA
<213> ORGANISM: artificial sequence
<220> FEATURE:
<223> OTHER INFORMATION: synthetic

<400> SEQUENCE: 46
cagaccggaa gccgccattt tgatggggtc agtac                            35

<210> SEQ ID NO 47
<211> LENGTH: 42
<212> TYPE: DNA
<213> ORGANISM: artificial sequence
<220> FEATURE:
<223> OTHER INFORMATION: synthetic

<400> SEQUENCE: 47
taatattgga gcaaacaaga gatcaatatg atattgcctt ta                    42

<210> SEQ ID NO 48
<211> LENGTH: 28
<212> TYPE: DNA
<213> ORGANISM: artificial sequence
<220> FEATURE:
<223> OTHER INFORMATION: synthetic

<400> SEQUENCE: 48
ttccttatag caagcaaatc aaatttta                                    28

<210> SEQ ID NO 49
<211> LENGTH: 36
<212> TYPE: DNA
<213> ORGANISM: artificial sequence
<220> FEATURE:
<223> OTHER INFORMATION: synthetic

<400> SEQUENCE: 49
actacgagga gatttttca cgttgaaact tgcttt                            36

<210> SEQ ID NO 50
<211> LENGTH: 42
<212> TYPE: DNA
<213> ORGANISM: artificial sequence
<220> FEATURE:
<223> OTHER INFORMATION: synthetic

<400> SEQUENCE: 50
aaacaggcat gtcaatcata tagattcaaa agggttatat tt                    42

<210> SEQ ID NO 51
<211> LENGTH: 38
<212> TYPE: DNA
<213> ORGANISM: artificial sequence
<220> FEATURE:
<223> OTHER INFORMATION: synthetic

<400> SEQUENCE: 51
aacaggcacc agttaaaggc cgctttgtga atttctta                         38

<210> SEQ ID NO 52
<211> LENGTH: 40
<212> TYPE: DNA
<213> ORGANISM: artificial sequence
<220> FEATURE:
<223> OTHER INFORMATION: synthetic

<400> SEQUENCE: 52
ttcctgagtt atctaaaata ttcagttgtt caaatagcag                40

<210> SEQ ID NO 53
<211> LENGTH: 24
<212> TYPE: DNA
<213> ORGANISM: artificial sequence
<220> FEATURE:
<223> OTHER INFORMATION: synthetic

<400> SEQUENCE: 53
aaagaaacaa gagaagatcc ggct                                24

<210> SEQ ID NO 54
<211> LENGTH: 28
<212> TYPE: DNA
<213> ORGANISM: artificial sequence
<220> FEATURE:
<223> OTHER INFORMATION: synthetic

<400> SEQUENCE: 54
ttgagggttc tggtcaggct gtataagc                            28

<210> SEQ ID NO 55
<211> LENGTH: 42
<212> TYPE: DNA
<213> ORGANISM: artificial sequence
<220> FEATURE:
<223> OTHER INFORMATION: synthetic

<400> SEQUENCE: 55
tttaaccgtc aatagtgaat tcaaaagaag atgatatcgc gc            42

<210> SEQ ID NO 56
<211> LENGTH: 32
<212> TYPE: DNA
<213> ORGANISM: artificial sequence
<220> FEATURE:
<223> OTHER INFORMATION: synthetic

<400> SEQUENCE: 56
acgagcgccc aatccaaata aaattgagca cc                       32

<210> SEQ ID NO 57
<211> LENGTH: 32
<212> TYPE: DNA
<213> ORGANISM: artificial sequence
<220> FEATURE:
<223> OTHER INFORMATION: synthetic

<400> SEQUENCE: 57
aataagtcga agcccaataa ttatttattc tt                       32

<210> SEQ ID NO 58
<211> LENGTH: 35
<212> TYPE: DNA
<213> ORGANISM: artificial sequence
<220> FEATURE:
<223> OTHER INFORMATION: synthetic

<400> SEQUENCE: 58
acgaaatatc atagattaag aaacaatgga actga                    35

<210> SEQ ID NO 59

```
<211> LENGTH: 31
<212> TYPE: DNA
<213> ORGANISM: artificial sequence
<220> FEATURE:
<223> OTHER INFORMATION: synthetic

<400> SEQUENCE: 59
tttcatagtt gtaccgtaac actggggttt t                              31

<210> SEQ ID NO 60
<211> LENGTH: 42
<212> TYPE: DNA
<213> ORGANISM: artificial sequence
<220> FEATURE:
<223> OTHER INFORMATION: synthetic

<400> SEQUENCE: 60
aggagcgagc actaacaact aaaaccctat cacctaacag tg                  42

<210> SEQ ID NO 61
<211> LENGTH: 35
<212> TYPE: DNA
<213> ORGANISM: artificial sequence
<220> FEATURE:
<223> OTHER INFORMATION: synthetic

<400> SEQUENCE: 61
caaagtatta attagcgagt ttcgccacag aacga                          35

<210> SEQ ID NO 62
<211> LENGTH: 35
<212> TYPE: DNA
<213> ORGANISM: artificial sequence
<220> FEATURE:
<223> OTHER INFORMATION: synthetic

<400> SEQUENCE: 62
tggggagcta tttgacgact aaataccatc agttt                          35

<210> SEQ ID NO 63
<211> LENGTH: 28
<212> TYPE: DNA
<213> ORGANISM: artificial sequence
<220> FEATURE:
<223> OTHER INFORMATION: synthetic

<400> SEQUENCE: 63
ataacgcaat agtaaaatgt ttaaatca                                  28

<210> SEQ ID NO 64
<211> LENGTH: 28
<212> TYPE: DNA
<213> ORGANISM: artificial sequence
<220> FEATURE:
<223> OTHER INFORMATION: synthetic

<400> SEQUENCE: 64
acgaatcaac cttcatctta taccgagg                                  28

<210> SEQ ID NO 65
<211> LENGTH: 21
<212> TYPE: DNA
<213> ORGANISM: artificial sequence
<220> FEATURE:
<223> OTHER INFORMATION: synthetic

<400> SEQUENCE: 65
```
taatggtttg aaatacgcca a                                                 21

<210> SEQ ID NO 66
<211> LENGTH: 42
<212> TYPE: DNA
<213> ORGANISM: artificial sequence
<220> FEATURE:
<223> OTHER INFORMATION: synthetic

<400> SEQUENCE: 66
cggaacaaga gccgtcaata ggcacagaca atatcctcaa tc                          42

<210> SEQ ID NO 67
<211> LENGTH: 31
<212> TYPE: DNA
<213> ORGANISM: artificial sequence
<220> FEATURE:
<223> OTHER INFORMATION: synthetic

<400> SEQUENCE: 67
attaaaggtg aattatcaaa gggcaccacg g                                      31

<210> SEQ ID NO 68
<211> LENGTH: 31
<212> TYPE: DNA
<213> ORGANISM: artificial sequence
<220> FEATURE:
<223> OTHER INFORMATION: synthetic

<400> SEQUENCE: 68
ggcaacccat agcgtaagca gcgaccatta a                                      31

<210> SEQ ID NO 69
<211> LENGTH: 32
<212> TYPE: DNA
<213> ORGANISM: artificial sequence
<220> FEATURE:
<223> OTHER INFORMATION: synthetic

<400> SEQUENCE: 69
agaaacgtaa gcagccacaa ggaaacgatc tt                                     32

<210> SEQ ID NO 70
<211> LENGTH: 28
<212> TYPE: DNA
<213> ORGANISM: artificial sequence
<220> FEATURE:
<223> OTHER INFORMATION: synthetic

<400> SEQUENCE: 70
agaggtcttt aggggggtcaa aaggcagt                                         28

<210> SEQ ID NO 71
<211> LENGTH: 42
<212> TYPE: DNA
<213> ORGANISM: artificial sequence
<220> FEATURE:
<223> OTHER INFORMATION: synthetic

<400> SEQUENCE: 71
ggggactttt tcatgaggac ctgcgagaat agaaaggagg at                          42

<210> SEQ ID NO 72
<211> LENGTH: 28
<212> TYPE: DNA

```
<213> ORGANISM: artificial sequence
<220> FEATURE:
<223> OTHER INFORMATION: synthetic

<400> SEQUENCE: 72
ttttagaaca tccaataaat ccaataac                                            28

<210> SEQ ID NO 73
<211> LENGTH: 28
<212> TYPE: DNA
<213> ORGANISM: artificial sequence
<220> FEATURE:
<223> OTHER INFORMATION: synthetic

<400> SEQUENCE: 73
aaatgtggta gatggcccgc ttgggcgc                                            28

<210> SEQ ID NO 74
<211> LENGTH: 31
<212> TYPE: DNA
<213> ORGANISM: artificial sequence
<220> FEATURE:
<223> OTHER INFORMATION: synthetic

<400> SEQUENCE: 74
acggatcgtc accctcacga tctagaattt t                                        31

<210> SEQ ID NO 75
<211> LENGTH: 28
<212> TYPE: DNA
<213> ORGANISM: artificial sequence
<220> FEATURE:
<223> OTHER INFORMATION: synthetic

<400> SEQUENCE: 75
cgccataaga cgacgacaat agctgtct                                            28

<210> SEQ ID NO 76
<211> LENGTH: 31
<212> TYPE: DNA
<213> ORGANISM: artificial sequence
<220> FEATURE:
<223> OTHER INFORMATION: synthetic

<400> SEQUENCE: 76
gcgtattagt ctttaatcgt aagaatttac a                                        31

<210> SEQ ID NO 77
<211> LENGTH: 35
<212> TYPE: DNA
<213> ORGANISM: artificial sequence
<220> FEATURE:
<223> OTHER INFORMATION: synthetic

<400> SEQUENCE: 77
agagaacgtg aatcaaatgc gtatttccag tcccc                                    35

<210> SEQ ID NO 78
<211> LENGTH: 33
<212> TYPE: DNA
<213> ORGANISM: artificial sequence
<220> FEATURE:
<223> OTHER INFORMATION: synthetic

<400> SEQUENCE: 78
aacgaaaaag cgcgaaaaaa aggctccaaa agg                                      33
```

<210> SEQ ID NO 79
<211> LENGTH: 28
<212> TYPE: DNA
<213> ORGANISM: artificial sequence
<220> FEATURE:
<223> OTHER INFORMATION: synthetic

<400> SEQUENCE: 79
taatttagaa cgcgaggcgt taagcctt                                    28

<210> SEQ ID NO 80
<211> LENGTH: 28
<212> TYPE: DNA
<213> ORGANISM: artificial sequence
<220> FEATURE:
<223> OTHER INFORMATION: synthetic

<400> SEQUENCE: 80
accaggcgtg catcattaat tttttcac                                    28

<210> SEQ ID NO 81
<211> LENGTH: 28
<212> TYPE: DNA
<213> ORGANISM: artificial sequence
<220> FEATURE:
<223> OTHER INFORMATION: synthetic

<400> SEQUENCE: 81
cagcctgacg acagatgtcg cctgaaat                                    28

<210> SEQ ID NO 82
<211> LENGTH: 35
<212> TYPE: DNA
<213> ORGANISM: artificial sequence
<220> FEATURE:
<223> OTHER INFORMATION: synthetic

<400> SEQUENCE: 82
attagtcaga ttgcaaagta agagttaaga agagt                            35

<210> SEQ ID NO 83
<211> LENGTH: 21
<212> TYPE: DNA
<213> ORGANISM: artificial sequence
<220> FEATURE:
<223> OTHER INFORMATION: synthetic

<400> SEQUENCE: 83
ctcgaatgct cactggcgca t                                           21

<210> SEQ ID NO 84
<211> LENGTH: 31
<212> TYPE: DNA
<213> ORGANISM: artificial sequence
<220> FEATURE:
<223> OTHER INFORMATION: synthetic

<400> SEQUENCE: 84
gggcagtcac gacgttgaat aattaacaac c                                31

<210> SEQ ID NO 85
<211> LENGTH: 38
<212> TYPE: DNA
<213> ORGANISM: artificial sequence
<220> FEATURE:

<223> OTHER INFORMATION: synthetic

<400> SEQUENCE: 85
taaaaacagg ggttttgtta gcgaataata taatagat                              38

<210> SEQ ID NO 86
<211> LENGTH: 31
<212> TYPE: DNA
<213> ORGANISM: artificial sequence
<220> FEATURE:
<223> OTHER INFORMATION: synthetic

<400> SEQUENCE: 86
tcaaccctca gcgccgaata tattaagaat a                                     31

<210> SEQ ID NO 87
<211> LENGTH: 35
<212> TYPE: DNA
<213> ORGANISM: artificial sequence
<220> FEATURE:
<223> OTHER INFORMATION: synthetic

<400> SEQUENCE: 87
attatacgtg ataatacaca ttatcatatc agaga                                 35

<210> SEQ ID NO 88
<211> LENGTH: 25
<212> TYPE: DNA
<213> ORGANISM: artificial sequence
<220> FEATURE:
<223> OTHER INFORMATION: synthetic

<400> SEQUENCE: 88
gcaaatctgc aacaggaaaa attgc                                            25

<210> SEQ ID NO 89
<211> LENGTH: 21
<212> TYPE: DNA
<213> ORGANISM: artificial sequence
<220> FEATURE:
<223> OTHER INFORMATION: synthetic

<400> SEQUENCE: 89
ataattacta gaaattctta c                                                21

<210> SEQ ID NO 90
<211> LENGTH: 42
<212> TYPE: DNA
<213> ORGANISM: artificial sequence
<220> FEATURE:
<223> OTHER INFORMATION: synthetic

<400> SEQUENCE: 90
tatcaccgtg ccttgagtaa cgcgtcatac atggcccctc ag                         42

<210> SEQ ID NO 91
<211> LENGTH: 28
<212> TYPE: DNA
<213> ORGANISM: artificial sequence
<220> FEATURE:
<223> OTHER INFORMATION: synthetic

<400> SEQUENCE: 91
aagtagggtt aacgcgctgc cagctgca                                         28

```
<210> SEQ ID NO 92
<211> LENGTH: 32
<212> TYPE: DNA
<213> ORGANISM: artificial sequence
<220> FEATURE:
<223> OTHER INFORMATION: synthetic

<400> SEQUENCE: 92
ccagtagtta agccctttt aagaaaagca aa                                    32

<210> SEQ ID NO 93
<211> LENGTH: 21
<212> TYPE: DNA
<213> ORGANISM: artificial sequence
<220> FEATURE:
<223> OTHER INFORMATION: synthetic

<400> SEQUENCE: 93
tggcgaagtt gggactttcc g                                               21

<210> SEQ ID NO 94
<211> LENGTH: 42
<212> TYPE: DNA
<213> ORGANISM: artificial sequence
<220> FEATURE:
<223> OTHER INFORMATION: synthetic

<400> SEQUENCE: 94
cagtgagtga tggtggttcc gaaaaccgtc tatcacgatt ta                        42

<210> SEQ ID NO 95
<211> LENGTH: 32
<212> TYPE: DNA
<213> ORGANISM: artificial sequence
<220> FEATURE:
<223> OTHER INFORMATION: synthetic

<400> SEQUENCE: 95
aaatcaaaga gaataacata actgaacaca gt                                   32

<210> SEQ ID NO 96
<211> LENGTH: 21
<212> TYPE: DNA
<213> ORGANISM: artificial sequence
<220> FEATURE:
<223> OTHER INFORMATION: synthetic

<400> SEQUENCE: 96
ctgtatgaca actagtgtcg a                                               21

<210> SEQ ID NO 97
<211> LENGTH: 42
<212> TYPE: DNA
<213> ORGANISM: artificial sequence
<220> FEATURE:
<223> OTHER INFORMATION: synthetic

<400> SEQUENCE: 97
atcataaata gcgagaggct tagcaaagcg gattgttcaa at                        42

<210> SEQ ID NO 98
<211> LENGTH: 42
<212> TYPE: DNA
<213> ORGANISM: artificial sequence
<220> FEATURE:
<223> OTHER INFORMATION: synthetic
```

<400> SEQUENCE: 98
ttgagtaatt tgaggattta gctgaaaggc gcgaaagata aa                           42

<210> SEQ ID NO 99
<211> LENGTH: 21
<212> TYPE: DNA
<213> ORGANISM: artificial sequence
<220> FEATURE:
<223> OTHER INFORMATION: synthetic

<400> SEQUENCE: 99
ataagaataa acaccgctca a                                                  21

<210> SEQ ID NO 100
<211> LENGTH: 32
<212> TYPE: DNA
<213> ORGANISM: artificial sequence
<220> FEATURE:
<223> OTHER INFORMATION: synthetic

<400> SEQUENCE: 100
cgttgtaatt caccttctga caagtatttt aa                                      32

<210> SEQ ID NO 101
<211> LENGTH: 28
<212> TYPE: DNA
<213> ORGANISM: artificial sequence
<220> FEATURE:
<223> OTHER INFORMATION: synthetic

<400> SEQUENCE: 101
aaccgcctca taattcggca tagcagca                                           28

<210> SEQ ID NO 102
<211> LENGTH: 38
<212> TYPE: DNA
<213> ORGANISM: artificial sequence
<220> FEATURE:
<223> OTHER INFORMATION: synthetic

<400> SEQUENCE: 102
aaataggtca cgttggtagc gagtcgcgtc taattcgc                                38

<210> SEQ ID NO 103
<211> LENGTH: 28
<212> TYPE: DNA
<213> ORGANISM: artificial sequence
<220> FEATURE:
<223> OTHER INFORMATION: synthetic

<400> SEQUENCE: 103
cagtatagcc tgtttatcaa ccccatcc                                           28

<210> SEQ ID NO 104
<211> LENGTH: 42
<212> TYPE: DNA
<213> ORGANISM: artificial sequence
<220> FEATURE:
<223> OTHER INFORMATION: synthetic

<400> SEQUENCE: 104
ttgcacctga aaatagcagc cagagggtca tcgattttcg gt                           42

<210> SEQ ID NO 105
<211> LENGTH: 28

```
<212> TYPE: DNA
<213> ORGANISM: artificial sequence
<220> FEATURE:
<223> OTHER INFORMATION: synthetic

<400> SEQUENCE: 105
cgtcggaaat gggacctgtc gggggaga                                      28

<210> SEQ ID NO 106
<211> LENGTH: 28
<212> TYPE: DNA
<213> ORGANISM: artificial sequence
<220> FEATURE:
<223> OTHER INFORMATION: synthetic

<400> SEQUENCE: 106
aagaaactag aagattgcgc aactaggg                                      28

<210> SEQ ID NO 107
<211> LENGTH: 28
<212> TYPE: DNA
<213> ORGANISM: artificial sequence
<220> FEATURE:
<223> OTHER INFORMATION: synthetic

<400> SEQUENCE: 107
ccagaacctg gctcattata caattacg                                      28

<210> SEQ ID NO 108
<211> LENGTH: 32
<212> TYPE: DNA
<213> ORGANISM: artificial sequence
<220> FEATURE:
<223> OTHER INFORMATION: synthetic

<400> SEQUENCE: 108
acgggtaata aattaaggaa ttgcgaatag ta                                 32

<210> SEQ ID NO 109
<211> LENGTH: 32
<212> TYPE: DNA
<213> ORGANISM: artificial sequence
<220> FEATURE:
<223> OTHER INFORMATION: synthetic

<400> SEQUENCE: 109
ccacgctggc cgattcaaac tatcggcccg ct                                 32

<210> SEQ ID NO 110
<211> LENGTH: 31
<212> TYPE: DNA
<213> ORGANISM: artificial sequence
<220> FEATURE:
<223> OTHER INFORMATION: synthetic

<400> SEQUENCE: 110
gccttcaccg aaagcctccg ctcacgccag c                                  31

<210> SEQ ID NO 111
<211> LENGTH: 28
<212> TYPE: DNA
<213> ORGANISM: artificial sequence
<220> FEATURE:
<223> OTHER INFORMATION: synthetic

<400> SEQUENCE: 111
```
cagcattaaa gacaaccgtc aaaaatca                                              28

<210> SEQ ID NO 112
<211> LENGTH: 28
<212> TYPE: DNA
<213> ORGANISM: artificial sequence
<220> FEATURE:
<223> OTHER INFORMATION: synthetic

<400> SEQUENCE: 112
acatcggaaa ttatttgcac gtaaaagt                                              28

<210> SEQ ID NO 113
<211> LENGTH: 42
<212> TYPE: DNA
<213> ORGANISM: artificial sequence
<220> FEATURE:
<223> OTHER INFORMATION: synthetic

<400> SEQUENCE: 113
caacggtcgc tgaggcttga tacctatcgg tttatcagat ct                              42

<210> SEQ ID NO 114
<211> LENGTH: 28
<212> TYPE: DNA
<213> ORGANISM: artificial sequence
<220> FEATURE:
<223> OTHER INFORMATION: synthetic

<400> SEQUENCE: 114
aaatcgtaca gtacataaat cagatgaa                                              28

<210> SEQ ID NO 115
<211> LENGTH: 32
<212> TYPE: DNA
<213> ORGANISM: artificial sequence
<220> FEATURE:
<223> OTHER INFORMATION: synthetic

<400> SEQUENCE: 115
ttaacacaca ggaacacttg cctgagtatt tg                                         32

<210> SEQ ID NO 116
<211> LENGTH: 28
<212> TYPE: DNA
<213> ORGANISM: artificial sequence
<220> FEATURE:
<223> OTHER INFORMATION: synthetic

<400> SEQUENCE: 116
aggcataaga agttttgcca gaccctga                                              28

<210> SEQ ID NO 117
<211> LENGTH: 35
<212> TYPE: DNA
<213> ORGANISM: artificial sequence
<220> FEATURE:
<223> OTHER INFORMATION: synthetic

<400> SEQUENCE: 117
gacgacattc accagagatt aaagcctatt aacca                                      35

<210> SEQ ID NO 118
<211> LENGTH: 28
<212> TYPE: DNA
<213> ORGANISM: artificial sequence

```
<220> FEATURE:
<223> OTHER INFORMATION: synthetic

<400> SEQUENCE: 118
agctgctcgt taataaaacg agaatacc                                               28

<210> SEQ ID NO 119
<211> LENGTH: 39
<212> TYPE: DNA
<213> ORGANISM: artificial sequence
<220> FEATURE:
<223> OTHER INFORMATION: synthetic

<400> SEQUENCE: 119
cttagagtac cttttaaaca gctgcggaga tttagacta                                   39

<210> SEQ ID NO 120
<211> LENGTH: 28
<212> TYPE: DNA
<213> ORGANISM: artificial sequence
<220> FEATURE:
<223> OTHER INFORMATION: synthetic

<400> SEQUENCE: 120
caccctctaa ttagcgtttg ctacatac                                               28

<210> SEQ ID NO 121
<211> LENGTH: 42
<212> TYPE: DNA
<213> ORGANISM: artificial sequence
<220> FEATURE:
<223> OTHER INFORMATION: synthetic

<400> SEQUENCE: 121
gaaccgaaaa ttgggcttga gtaccttatg cgattcaaca ct                               42

<210> SEQ ID NO 122
<211> LENGTH: 39
<212> TYPE: DNA
<213> ORGANISM: artificial sequence
<220> FEATURE:
<223> OTHER INFORMATION: synthetic

<400> SEQUENCE: 122
gcaaggcaga taacatagcc gaacaaagtg gcaacggga                                   39

<210> SEQ ID NO 123
<211> LENGTH: 32
<212> TYPE: DNA
<213> ORGANISM: artificial sequence
<220> FEATURE:
<223> OTHER INFORMATION: synthetic

<400> SEQUENCE: 123
atgaaacaat tgagaaggaa accgaggata ga                                          32

<210> SEQ ID NO 124
<211> LENGTH: 31
<212> TYPE: DNA
<213> ORGANISM: artificial sequence
<220> FEATURE:
<223> OTHER INFORMATION: synthetic

<400> SEQUENCE: 124
ggatgtgaaa ttgttatggg gtgcacagta t                                           31
```

<210> SEQ ID NO 125
<211> LENGTH: 28
<212> TYPE: DNA
<213> ORGANISM: artificial sequence
<220> FEATURE:
<223> OTHER INFORMATION: synthetic

<400> SEQUENCE: 125
ggcttgcgac gttgggaaga acagatac                                28

<210> SEQ ID NO 126
<211> LENGTH: 28
<212> TYPE: DNA
<213> ORGANISM: artificial sequence
<220> FEATURE:
<223> OTHER INFORMATION: synthetic

<400> SEQUENCE: 126
taaatgccta ctaatagtag ttttcatt                                28

<210> SEQ ID NO 127
<211> LENGTH: 45
<212> TYPE: DNA
<213> ORGANISM: artificial sequence
<220> FEATURE:
<223> OTHER INFORMATION: synthetic

<400> SEQUENCE: 127
tgccgtctgc ctatttcgga accagaatgg aaagcccacc agaac             45

<210> SEQ ID NO 128
<211> LENGTH: 25
<212> TYPE: DNA
<213> ORGANISM: artificial sequence
<220> FEATURE:
<223> OTHER INFORMATION: synthetic

<400> SEQUENCE: 128
tgaccatagc aaaagggaga acaac                                   25

<210> SEQ ID NO 129
<211> LENGTH: 27
<212> TYPE: DNA
<213> ORGANISM: artificial sequence
<220> FEATURE:
<223> OTHER INFORMATION: synthetic

<400> SEQUENCE: 129
cgagccagac gttaataatt tgtatca                                 27

<210> SEQ ID NO 130
<211> LENGTH: 42
<212> TYPE: DNA
<213> ORGANISM: artificial sequence
<220> FEATURE:
<223> OTHER INFORMATION: synthetic

<400> SEQUENCE: 130
gctcagtttc tgaaacatga acaaataaa tcctcccgcc gc                 42

<210> SEQ ID NO 131
<211> LENGTH: 28
<212> TYPE: DNA
<213> ORGANISM: artificial sequence
<220> FEATURE:
<223> OTHER INFORMATION: synthetic

<400> SEQUENCE: 131
agacgctaca tcaagaaaac actttgaa                                              28

<210> SEQ ID NO 132
<211> LENGTH: 31
<212> TYPE: DNA
<213> ORGANISM: artificial sequence
<220> FEATURE:
<223> OTHER INFORMATION: synthetic

<400> SEQUENCE: 132
agtactgacc aatccgcgaa gtttaagaca g                                          31

<210> SEQ ID NO 133
<211> LENGTH: 38
<212> TYPE: DNA
<213> ORGANISM: artificial sequence
<220> FEATURE:
<223> OTHER INFORMATION: synthetic

<400> SEQUENCE: 133
gattcctgtt acgggcagtg agcttttcct gtgtgctg                                   38

<210> SEQ ID NO 134
<211> LENGTH: 28
<212> TYPE: DNA
<213> ORGANISM: artificial sequence
<220> FEATURE:
<223> OTHER INFORMATION: synthetic

<400> SEQUENCE: 134
ggtattaagg aatcattacc gaacgcta                                              28

<210> SEQ ID NO 135
<211> LENGTH: 35
<212> TYPE: DNA
<213> ORGANISM: artificial sequence
<220> FEATURE:
<223> OTHER INFORMATION: synthetic

<400> SEQUENCE: 135
gttcatcaaa taaaacgcga ctctagagga tcggg                                      35

<210> SEQ ID NO 136
<211> LENGTH: 40
<212> TYPE: DNA
<213> ORGANISM: artificial sequence
<220> FEATURE:
<223> OTHER INFORMATION: synthetic

<400> SEQUENCE: 136
agcctttaat tggatagttg aaccgccacc ctcataggtg                                 40

<210> SEQ ID NO 137
<211> LENGTH: 32
<212> TYPE: DNA
<213> ORGANISM: artificial sequence
<220> FEATURE:
<223> OTHER INFORMATION: synthetic

<400> SEQUENCE: 137
acagaggcct gagattcttt gattagtaat gg                                         32

<210> SEQ ID NO 138

<211> LENGTH: 28
<212> TYPE: DNA
<213> ORGANISM: artificial sequence
<220> FEATURE:
<223> OTHER INFORMATION: synthetic

<400> SEQUENCE: 138
aacgagatca ggattagaga gcttaatt                                28

<210> SEQ ID NO 139
<211> LENGTH: 28
<212> TYPE: DNA
<213> ORGANISM: artificial sequence
<220> FEATURE:
<223> OTHER INFORMATION: synthetic

<400> SEQUENCE: 139
taccaagtta tacttctgaa tcaccaga                                28

<210> SEQ ID NO 140
<211> LENGTH: 28
<212> TYPE: DNA
<213> ORGANISM: artificial sequence
<220> FEATURE:
<223> OTHER INFORMATION: synthetic

<400> SEQUENCE: 140
cagtaggtgt tcagctaatg cgtagaaa                                28

<210> SEQ ID NO 141
<211> LENGTH: 49
<212> TYPE: DNA
<213> ORGANISM: artificial sequence
<220> FEATURE:
<223> OTHER INFORMATION: synthetic

<400> SEQUENCE: 141
aggatgacca tagactgact aatgaaatct acattcagca ggcgcgtac         49

<210> SEQ ID NO 142
<211> LENGTH: 28
<212> TYPE: DNA
<213> ORGANISM: artificial sequence
<220> FEATURE:
<223> OTHER INFORMATION: synthetic

<400> SEQUENCE: 142
tttcaaccaa ggcaaagaat ttagatac                                28

<210> SEQ ID NO 143
<211> LENGTH: 24
<212> TYPE: DNA
<213> ORGANISM: artificial sequence
<220> FEATURE:
<223> OTHER INFORMATION: synthetic

<400> SEQUENCE: 143
ttgaaattaa gatagcttaa ctat                                    24

<210> SEQ ID NO 144
<211> LENGTH: 28
<212> TYPE: DNA
<213> ORGANISM: artificial sequence
<220> FEATURE:
<223> OTHER INFORMATION: synthetic

<400> SEQUENCE: 144

```
ctattatcga gcttcaaagc gtatgcaa                                              28
```

<210> SEQ ID NO 145
<211> LENGTH: 42
<212> TYPE: DNA
<213> ORGANISM: artificial sequence
<220> FEATURE:
<223> OTHER INFORMATION: synthetic

<400> SEQUENCE: 145

```
cagggtgcaa atcccttat agactccaac gtcaaaagcc gg                              42
```

<210> SEQ ID NO 146
<211> LENGTH: 42
<212> TYPE: DNA
<213> ORGANISM: artificial sequence
<220> FEATURE:
<223> OTHER INFORMATION: synthetic

<400> SEQUENCE: 146

```
gagcttgtta atgcgccgct aattttagcg cctgctgctg aa                             42
```

<210> SEQ ID NO 147
<211> LENGTH: 32
<212> TYPE: DNA
<213> ORGANISM: artificial sequence
<220> FEATURE:
<223> OTHER INFORMATION: synthetic

<400> SEQUENCE: 147

```
cgaacgttaa ccaccacacc cccagaattg ag                                        32
```

<210> SEQ ID NO 148
<211> LENGTH: 21
<212> TYPE: DNA
<213> ORGANISM: artificial sequence
<220> FEATURE:
<223> OTHER INFORMATION: synthetic

<400> SEQUENCE: 148

```
gtgtgataaa taagtgagaa t                                                    21
```

<210> SEQ ID NO 149
<211> LENGTH: 25
<212> TYPE: DNA
<213> ORGANISM: artificial sequence
<220> FEATURE:
<223> OTHER INFORMATION: synthetic

<400> SEQUENCE: 149

```
gctatatagc attaccctc agaga                                                 25
```

<210> SEQ ID NO 150
<211> LENGTH: 35
<212> TYPE: DNA
<213> ORGANISM: artificial sequence
<220> FEATURE:
<223> OTHER INFORMATION: synthetic

<400> SEQUENCE: 150

```
aggagagccg gcagtcttgc ccccgagagg gaggg                                     35
```

<210> SEQ ID NO 151
<211> LENGTH: 28
<212> TYPE: DNA

<210> SEQ ID NO 152
<211> LENGTH: 31
<212> TYPE: DNA
<213> ORGANISM: artificial sequence
<220> FEATURE:
<223> OTHER INFORMATION: synthetic

<400> SEQUENCE: 151
cggcctccag ccagagggcg agcccccaa                                       28

<210> SEQ ID NO 152
<211> LENGTH: 31
<212> TYPE: DNA
<213> ORGANISM: artificial sequence
<220> FEATURE:
<223> OTHER INFORMATION: synthetic

<400> SEQUENCE: 152
ccaaaacaaa ataggctggc tgacgtaaca a                                    31

<210> SEQ ID NO 153
<211> LENGTH: 42
<212> TYPE: DNA
<213> ORGANISM: artificial sequence
<220> FEATURE:
<223> OTHER INFORMATION: synthetic

<400> SEQUENCE: 153
ggcggttaga atagcccgag aagtccacta ttaaaaagga ag                        42

<210> SEQ ID NO 154
<211> LENGTH: 32
<212> TYPE: DNA
<213> ORGANISM: artificial sequence
<220> FEATURE:
<223> OTHER INFORMATION: synthetic

<400> SEQUENCE: 154
ataaaggtta ccagcgctaa ttcaaaaaca gc                                   32

<210> SEQ ID NO 155
<211> LENGTH: 42
<212> TYPE: DNA
<213> ORGANISM: artificial sequence
<220> FEATURE:
<223> OTHER INFORMATION: synthetic

<400> SEQUENCE: 155
attgccccca gcaggcgaaa aggcccacta cgtgacggaa cc                        42

<210> SEQ ID NO 156
<211> LENGTH: 38
<212> TYPE: DNA
<213> ORGANISM: artificial sequence
<220> FEATURE:
<223> OTHER INFORMATION: synthetic

<400> SEQUENCE: 156
ttttaaaaca taacagtaat ggaacgctat tagaacgc                             38

<210> SEQ ID NO 157
<211> LENGTH: 38
<212> TYPE: DNA
<213> ORGANISM: artificial sequence
<220> FEATURE:
<223> OTHER INFORMATION: synthetic

<400> SEQUENCE: 157
aattgggtaa cgccaggctg tagccagcta gtaaacgt                             38

<210> SEQ ID NO 158
<211> LENGTH: 41
<212> TYPE: DNA
<213> ORGANISM: artificial sequence
<220> FEATURE:
<223> OTHER INFORMATION: synthetic

<400> SEQUENCE: 158
ttacccagaa caacattatt acaggttttt tttttttttt t                          41

<210> SEQ ID NO 159
<211> LENGTH: 28
<212> TYPE: DNA
<213> ORGANISM: artificial sequence
<220> FEATURE:
<223> OTHER INFORMATION: synthetic

<400> SEQUENCE: 159
tttttttttt tttttaata agagaata                                          28

<210> SEQ ID NO 160
<211> LENGTH: 48
<212> TYPE: DNA
<213> ORGANISM: artificial sequence
<220> FEATURE:
<223> OTHER INFORMATION: synthetic

<400> SEQUENCE: 160
tttttttttt tttttccag tttgggagcg ggcttttttt tttttttt                    48

<210> SEQ ID NO 161
<211> LENGTH: 31
<212> TYPE: DNA
<213> ORGANISM: artificial sequence
<220> FEATURE:
<223> OTHER INFORMATION: synthetic

<400> SEQUENCE: 161
ggttgaggca ggtcagtttt tttttttttt t                                     31

<210> SEQ ID NO 162
<211> LENGTH: 42
<212> TYPE: DNA
<213> ORGANISM: artificial sequence
<220> FEATURE:
<223> OTHER INFORMATION: synthetic

<400> SEQUENCE: 162
tttttttttt tttttgatta agactcctta tccaaaagga at                         42

<210> SEQ ID NO 163
<211> LENGTH: 32
<212> TYPE: DNA
<213> ORGANISM: artificial sequence
<220> FEATURE:
<223> OTHER INFORMATION: synthetic

<400> SEQUENCE: 163
tttttttttt tttttcttc gctattacaa tt                                     32

<210> SEQ ID NO 164
<211> LENGTH: 48
<212> TYPE: DNA
<213> ORGANISM: artificial sequence
<220> FEATURE:

<223> OTHER INFORMATION: synthetic

<400> SEQUENCE: 164
tttttttttt ttttcttgc gggagaagcg cattttttt ttttttttt         48

<210> SEQ ID NO 165
<211> LENGTH: 50
<212> TYPE: DNA
<213> ORGANISM: artificial sequence
<220> FEATURE:
<223> OTHER INFORMATION: synthetic

<400> SEQUENCE: 165
tttttttttt ttttgggaat tagagaaaca atgaattttt tttttttttt        50

<210> SEQ ID NO 166
<211> LENGTH: 38
<212> TYPE: DNA
<213> ORGANISM: artificial sequence
<220> FEATURE:
<223> OTHER INFORMATION: synthetic

<400> SEQUENCE: 166
tcagactgac agaatcaagt tgttttttt tttttttt                     38

<210> SEQ ID NO 167
<211> LENGTH: 41
<212> TYPE: DNA
<213> ORGANISM: artificial sequence
<220> FEATURE:
<223> OTHER INFORMATION: synthetic

<400> SEQUENCE: 167
tttttttttt ttttggtcg aggtgccgta aagcagcacg t                 41

<210> SEQ ID NO 168
<211> LENGTH: 48
<212> TYPE: DNA
<213> ORGANISM: artificial sequence
<220> FEATURE:
<223> OTHER INFORMATION: synthetic

<400> SEQUENCE: 168
tttttttttt tttttttaa tcatttacca gactttttt tttttttt           48

<210> SEQ ID NO 169
<211> LENGTH: 50
<212> TYPE: DNA
<213> ORGANISM: artificial sequence
<220> FEATURE:
<223> OTHER INFORMATION: synthetic

<400> SEQUENCE: 169
tttttttttt tttcattctg gccaaattcg acaactcttt tttttttttt        50

<210> SEQ ID NO 170
<211> LENGTH: 27
<212> TYPE: DNA
<213> ORGANISM: artificial sequence
<220> FEATURE:
<223> OTHER INFORMATION: synthetic

<400> SEQUENCE: 170
tttttttttt ttttaccgg atattca                                 27

<210> SEQ ID NO 171
<211> LENGTH: 48
<212> TYPE: DNA
<213> ORGANISM: artificial sequence
<220> FEATURE:
<223> OTHER INFORMATION: synthetic

<400> SEQUENCE: 171
tttttttttt tttttagac gggaaactgg catttttttt tttttttt        48

<210> SEQ ID NO 172
<211> LENGTH: 41
<212> TYPE: DNA
<213> ORGANISM: artificial sequence
<220> FEATURE:
<223> OTHER INFORMATION: synthetic

<400> SEQUENCE: 172
tttttttttt tttttcagca agcggtccac gctgcccaaa t              41

<210> SEQ ID NO 173
<211> LENGTH: 27
<212> TYPE: DNA
<213> ORGANISM: artificial sequence
<220> FEATURE:
<223> OTHER INFORMATION: synthetic

<400> SEQUENCE: 173
ctgagagagt tgttttttttt tttttt                              27

<210> SEQ ID NO 174
<211> LENGTH: 31
<212> TYPE: DNA
<213> ORGANISM: artificial sequence
<220> FEATURE:
<223> OTHER INFORMATION: synthetic

<400> SEQUENCE: 174
caatgacaac aaccattttt tttttttttt t                         31

<210> SEQ ID NO 175
<211> LENGTH: 36
<212> TYPE: DNA
<213> ORGANISM: artificial sequence
<220> FEATURE:
<223> OTHER INFORMATION: synthetic

<400> SEQUENCE: 175
tttttttttt tttttgaga gatctacaag gagagg                     36

<210> SEQ ID NO 176
<211> LENGTH: 31
<212> TYPE: DNA
<213> ORGANISM: artificial sequence
<220> FEATURE:
<223> OTHER INFORMATION: synthetic

<400> SEQUENCE: 176
tcaccagtac aaactatttt tttttttttt t                         31

<210> SEQ ID NO 177
<211> LENGTH: 50
<212> TYPE: DNA
<213> ORGANISM: artificial sequence
<220> FEATURE:
<223> OTHER INFORMATION: synthetic

<400> SEQUENCE: 177
tttttttttt tttggcaatt catcaaatta ttcatttttt tttttttttt        50

<210> SEQ ID NO 178
<211> LENGTH: 40
<212> TYPE: DNA
<213> ORGANISM: artificial sequence
<220> FEATURE:
<223> OTHER INFORMATION: synthetic

<400> SEQUENCE: 178
taaagttacc gcactcatcg agaactttt tttttttttt        40

<210> SEQ ID NO 179
<211> LENGTH: 31
<212> TYPE: DNA
<213> ORGANISM: artificial sequence
<220> FEATURE:
<223> OTHER INFORMATION: synthetic

<400> SEQUENCE: 179
tttttttttt tttttcaccc tcagaaccgc c        31

<210> SEQ ID NO 180
<211> LENGTH: 50
<212> TYPE: DNA
<213> ORGANISM: artificial sequence
<220> FEATURE:
<223> OTHER INFORMATION: synthetic

<400> SEQUENCE: 180
tttttttttt tttaggttta acgtcaatat atgtgagttt tttttttttt        50

<210> SEQ ID NO 181
<211> LENGTH: 27
<212> TYPE: DNA
<213> ORGANISM: artificial sequence
<220> FEATURE:
<223> OTHER INFORMATION: synthetic

<400> SEQUENCE: 181
ccacacaaca tacgttttt tttttttt        27

<210> SEQ ID NO 182
<211> LENGTH: 48
<212> TYPE: DNA
<213> ORGANISM: artificial sequence
<220> FEATURE:
<223> OTHER INFORMATION: synthetic

<400> SEQUENCE: 182
tttttttttt ttttgctag ggcgagtaaa agattttttt ttttttt        48

<210> SEQ ID NO 183
<211> LENGTH: 42
<212> TYPE: DNA
<213> ORGANISM: artificial sequence
<220> FEATURE:
<223> OTHER INFORMATION: synthetic

<400> SEQUENCE: 183
tttttttttt tttttagttg attcccaatt ctgcgaacct ca        42

<210> SEQ ID NO 184
<211> LENGTH: 40

```
<212> TYPE: DNA
<213> ORGANISM: artificial sequence
<220> FEATURE:
<223> OTHER INFORMATION: synthetic

<400> SEQUENCE: 184
ttatttagag cctaatttgc cagtttttttt tttttttttt                    40

<210> SEQ ID NO 185
<211> LENGTH: 24
<212> TYPE: DNA
<213> ORGANISM: artificial sequence
<220> FEATURE:
<223> OTHER INFORMATION: synthetic

<400> SEQUENCE: 185
tttttttttt tttttacggc ggat                                      24

<210> SEQ ID NO 186
<211> LENGTH: 48
<212> TYPE: DNA
<213> ORGANISM: artificial sequence
<220> FEATURE:
<223> OTHER INFORMATION: synthetic

<400> SEQUENCE: 186
tttttttttt tttttatatg cgttaagtcc tgatttttt tttttttt             48

<210> SEQ ID NO 187
<211> LENGTH: 31
<212> TYPE: DNA
<213> ORGANISM: artificial sequence
<220> FEATURE:
<223> OTHER INFORMATION: synthetic

<400> SEQUENCE: 187
tttttttttt tttttacgat tggccttgat a                              31

<210> SEQ ID NO 188
<211> LENGTH: 31
<212> TYPE: DNA
<213> ORGANISM: artificial sequence
<220> FEATURE:
<223> OTHER INFORMATION: synthetic

<400> SEQUENCE: 188
tttttttttt tttttcaacg cctgtagcat t                              31

<210> SEQ ID NO 189
<211> LENGTH: 48
<212> TYPE: DNA
<213> ORGANISM: artificial sequence
<220> FEATURE:
<223> OTHER INFORMATION: synthetic

<400> SEQUENCE: 189
tttttttttt tttttggctt tgagccggaa cgatttttt tttttttt             48

<210> SEQ ID NO 190
<211> LENGTH: 28
<212> TYPE: DNA
<213> ORGANISM: artificial sequence
<220> FEATURE:
<223> OTHER INFORMATION: synthetic

<400> SEQUENCE: 190
```

```
tttttttttt tttttaagca agccgttt                                              28
```

<210> SEQ ID NO 191
<211> LENGTH: 50
<212> TYPE: DNA
<213> ORGANISM: artificial sequence
<220> FEATURE:
<223> OTHER INFORMATION: synthetic

<400> SEQUENCE: 191

```
tttttttttt tttatgtgta ggtaagtacc ccggttgttt tttttttttt                      50
```

<210> SEQ ID NO 192
<211> LENGTH: 34
<212> TYPE: DNA
<213> ORGANISM: artificial sequence
<220> FEATURE:
<223> OTHER INFORMATION: synthetic

<400> SEQUENCE: 192

```
atcgtcataa atattcattt tttttttttt tttt                                       34
```

<210> SEQ ID NO 193
<211> LENGTH: 28
<212> TYPE: DNA
<213> ORGANISM: artificial sequence
<220> FEATURE:
<223> OTHER INFORMATION: synthetic

<400> SEQUENCE: 193

```
tttttttttt tttttgttaa tttcatct                                              28
```

<210> SEQ ID NO 194
<211> LENGTH: 50
<212> TYPE: DNA
<213> ORGANISM: artificial sequence
<220> FEATURE:
<223> OTHER INFORMATION: synthetic

<400> SEQUENCE: 194

```
tttttttttt tttgtattaa atcctgcgta gattttcttt tttttttttt                      50
```

<210> SEQ ID NO 195
<211> LENGTH: 39
<212> TYPE: DNA
<213> ORGANISM: artificial sequence
<220> FEATURE:
<223> OTHER INFORMATION: synthetic

<400> SEQUENCE: 195

```
gccatataag agcaagccag cccgacttga gccatggtt                                  39
```

<210> SEQ ID NO 196
<211> LENGTH: 50
<212> TYPE: DNA
<213> ORGANISM: artificial sequence
<220> FEATURE:
<223> OTHER INFORMATION: synthetic

<400> SEQUENCE: 196

```
gtagctagta ccaaaaacat tcataaagct aaatcggttt tttttttttt                      50
```

<210> SEQ ID NO 197
<211> LENGTH: 27
<212> TYPE: DNA
<213> ORGANISM: artificial sequence

```
<220> FEATURE:
<223> OTHER INFORMATION: synthetic

<400> SEQUENCE: 197
ataacgtgct tttttttttt tttttt                                              27

<210> SEQ ID NO 198
<211> LENGTH: 48
<212> TYPE: DNA
<213> ORGANISM: artificial sequence
<220> FEATURE:
<223> OTHER INFORMATION: synthetic

<400> SEQUENCE: 198
tttttttttt ttttaaaat accgaacgaa ccaccagtga gaattaac                       48

<210> SEQ ID NO 199
<211> LENGTH: 27
<212> TYPE: DNA
<213> ORGANISM: artificial sequence
<220> FEATURE:
<223> OTHER INFORMATION: synthetic

<400> SEQUENCE: 199
tttttttttt ttttacaaa ataaaca                                              27

<210> SEQ ID NO 200
<211> LENGTH: 48
<212> TYPE: DNA
<213> ORGANISM: artificial sequence
<220> FEATURE:
<223> OTHER INFORMATION: synthetic

<400> SEQUENCE: 200
tttttttttt ttttacaag aaaaacctcc cgattttttt tttttttt                       48

<210> SEQ ID NO 201
<211> LENGTH: 48
<212> TYPE: DNA
<213> ORGANISM: artificial sequence
<220> FEATURE:
<223> OTHER INFORMATION: synthetic

<400> SEQUENCE: 201
tttttttttt ttttgacga taaaaagatt aagtttttt tttttttt                        48

<210> SEQ ID NO 202
<211> LENGTH: 50
<212> TYPE: DNA
<213> ORGANISM: artificial sequence
<220> FEATURE:
<223> OTHER INFORMATION: synthetic

<400> SEQUENCE: 202
tttttttttt tttcaattac ctgagtatca aaatcatttt tttttttttt                    50

<210> SEQ ID NO 203
<211> LENGTH: 34
<212> TYPE: DNA
<213> ORGANISM: artificial sequence
<220> FEATURE:
<223> OTHER INFORMATION: synthetic

<400> SEQUENCE: 203
ggtacggcca gtgccaagct tttttttttt tttt                                     34
```

<210> SEQ ID NO 204
<211> LENGTH: 50
<212> TYPE: DNA
<213> ORGANISM: artificial sequence
<220> FEATURE:
<223> OTHER INFORMATION: synthetic

<400> SEQUENCE: 204
tttttttttt ttttgaataa ccttgaaata tattttattt tttttttttt            50

<210> SEQ ID NO 205
<211> LENGTH: 27
<212> TYPE: DNA
<213> ORGANISM: artificial sequence
<220> FEATURE:
<223> OTHER INFORMATION: synthetic

<400> SEQUENCE: 205
cactaaaaca cttttttttt tttttt                                      27

<210> SEQ ID NO 206
<211> LENGTH: 48
<212> TYPE: DNA
<213> ORGANISM: artificial sequence
<220> FEATURE:
<223> OTHER INFORMATION: synthetic

<400> SEQUENCE: 206
tttttttttt tttttaacc aatatgggaa caattttttt tttttttt               48

<210> SEQ ID NO 207
<211> LENGTH: 34
<212> TYPE: DNA
<213> ORGANISM: artificial sequence
<220> FEATURE:
<223> OTHER INFORMATION: synthetic

<400> SEQUENCE: 207
tacgtcacaa tcaatagaat tttttttttt tttt                             34

<210> SEQ ID NO 208
<211> LENGTH: 34
<212> TYPE: DNA
<213> ORGANISM: artificial sequence
<220> FEATURE:
<223> OTHER INFORMATION: synthetic

<400> SEQUENCE: 208
tttttttttt ttttagaaa gattcatcag ttga                              34

<210> SEQ ID NO 209
<211> LENGTH: 50
<212> TYPE: DNA
<213> ORGANISM: artificial sequence
<220> FEATURE:
<223> OTHER INFORMATION: synthetic

<400> SEQUENCE: 209
tttttttttt tttgtggcat caattaatgc ctgagtattt tttttttttt            50

<210> SEQ ID NO 210
<211> LENGTH: 48
<212> TYPE: DNA
<213> ORGANISM: artificial sequence
<220> FEATURE:
<223> OTHER INFORMATION: synthetic

<400> SEQUENCE: 210
tttttttttt tttttttgca tgcctgcatt aattttttt tttttttt                                48

<210> SEQ ID NO 211
<211> LENGTH: 41
<212> TYPE: DNA
<213> ORGANISM: artificial sequence
<220> FEATURE:
<223> OTHER INFORMATION: synthetic

<400> SEQUENCE: 211
ccagcgaaag agtaatcttg acaagatttt tttttttttt t                                     41

<210> SEQ ID NO 212
<211> LENGTH: 34
<212> TYPE: DNA
<213> ORGANISM: artificial sequence
<220> FEATURE:
<223> OTHER INFORMATION: synthetic

<400> SEQUENCE: 212
tttttttttt tttttgaatc cccctcaaat gctt                                             34

<210> SEQ ID NO 213
<211> LENGTH: 31
<212> TYPE: DNA
<213> ORGANISM: artificial sequence
<220> FEATURE:
<223> OTHER INFORMATION: synthetic

<400> SEQUENCE: 213
agaggctgag actccttttt tttttttttt t                                                31

<210> SEQ ID NO 214
<211> LENGTH: 41
<212> TYPE: DNA
<213> ORGANISM: artificial sequence
<220> FEATURE:
<223> OTHER INFORMATION: synthetic

<400> SEQUENCE: 214
acaaacacag agatacatcg ccattatttt tttttttttt t                                     41

<210> SEQ ID NO 215
<211> LENGTH: 31
<212> TYPE: DNA
<213> ORGANISM: artificial sequence
<220> FEATURE:
<223> OTHER INFORMATION: synthetic

<400> SEQUENCE: 215
tttttttttt tttttcaaga gaaggattag g                                                31

<210> SEQ ID NO 216
<211> LENGTH: 50
<212> TYPE: DNA
<213> ORGANISM: artificial sequence
<220> FEATURE:
<223> OTHER INFORMATION: synthetic

<400> SEQUENCE: 216
tttttttttt tttgaattga ggaagttatc agatgatttt tttttttttt                            50

<210> SEQ ID NO 217

```
<211> LENGTH: 27
<212> TYPE: DNA
<213> ORGANISM: artificial sequence
<220> FEATURE:
<223> OTHER INFORMATION: synthetic

<400> SEQUENCE: 217
cagaacaata ttttttttt tttttt                                          27

<210> SEQ ID NO 218
<211> LENGTH: 39
<212> TYPE: DNA
<213> ORGANISM: artificial sequence
<220> FEATURE:
<223> OTHER INFORMATION: synthetic

<400> SEQUENCE: 218
tttttttttt tttagccgga agcataaagt gtcctggcc                           39

<210> SEQ ID NO 219
<211> LENGTH: 50
<212> TYPE: DNA
<213> ORGANISM: artificial sequence
<220> FEATURE:
<223> OTHER INFORMATION: synthetic

<400> SEQUENCE: 219
tgaccgtttc tccgggaacg caaatcagct catttttttt tttttttttt               50

<210> SEQ ID NO 220
<211> LENGTH: 31
<212> TYPE: DNA
<213> ORGANISM: artificial sequence
<220> FEATURE:
<223> OTHER INFORMATION: synthetic

<400> SEQUENCE: 220
tttttttttt tttttggtaa taagttttaa c                                   31

<210> SEQ ID NO 221
<211> LENGTH: 50
<212> TYPE: DNA
<213> ORGANISM: artificial sequence
<220> FEATURE:
<223> OTHER INFORMATION: synthetic

<400> SEQUENCE: 221
tttttttttt ttttgtctgt ccataataaa agggattttt tttttttttt               50

<210> SEQ ID NO 222
<211> LENGTH: 41
<212> TYPE: DNA
<213> ORGANISM: artificial sequence
<220> FEATURE:
<223> OTHER INFORMATION: synthetic

<400> SEQUENCE: 222
tttttttttt tttttcctcg ttagaatcag agcgtaatat c                        41

<210> SEQ ID NO 223
<211> LENGTH: 34
<212> TYPE: DNA
<213> ORGANISM: artificial sequence
<220> FEATURE:
<223> OTHER INFORMATION: synthetic

<400> SEQUENCE: 223
```

```
aattgctcct tttgataagt ttttttttttt tttt                              34
```

<210> SEQ ID NO 224
<211> LENGTH: 48
<212> TYPE: DNA
<213> ORGANISM: artificial sequence
<220> FEATURE:
<223> OTHER INFORMATION: synthetic

<400> SEQUENCE: 224

```
catcggacag ccctgctaaa caactttcaa cagtttttt tttttttt                 48
```

<210> SEQ ID NO 225
<211> LENGTH: 38
<212> TYPE: DNA
<213> ORGANISM: artificial sequence
<220> FEATURE:
<223> OTHER INFORMATION: synthetic

<400> SEQUENCE: 225

```
tttttttttt tttttaaccg cctccctcag accagagc                           38
```

<210> SEQ ID NO 226
<211> LENGTH: 40
<212> TYPE: DNA
<213> ORGANISM: artificial sequence
<220> FEATURE:
<223> OTHER INFORMATION: synthetic

<400> SEQUENCE: 226

```
tctgacagag gcattttcga gccagttttt tttttttttt                         40
```

<210> SEQ ID NO 227
<211> LENGTH: 41
<212> TYPE: DNA
<213> ORGANISM: artificial sequence
<220> FEATURE:
<223> OTHER INFORMATION: synthetic

<400> SEQUENCE: 227

```
tttttttttt ttttttttca gcggagttcc atgtcataag g                       41
```

<210> SEQ ID NO 228
<211> LENGTH: 31
<212> TYPE: DNA
<213> ORGANISM: artificial sequence
<220> FEATURE:
<223> OTHER INFORMATION: synthetic

<400> SEQUENCE: 228

```
tttttttttt tttttcgccc acgcataacc g                                  31
```

<210> SEQ ID NO 229
<211> LENGTH: 48
<212> TYPE: DNA
<213> ORGANISM: artificial sequence
<220> FEATURE:
<223> OTHER INFORMATION: synthetic

<400> SEQUENCE: 229

```
aattacttag gactaaatag caacggctac agatttttt tttttttt                 48
```

<210> SEQ ID NO 230
<211> LENGTH: 27
<212> TYPE: DNA

```
<213> ORGANISM: artificial sequence
<220> FEATURE:
<223> OTHER INFORMATION: synthetic

<400> SEQUENCE: 230
caagtttttt ggtttttttt ttttttt                                        27

<210> SEQ ID NO 231
<211> LENGTH: 48
<212> TYPE: DNA
<213> ORGANISM: artificial sequence
<220> FEATURE:
<223> OTHER INFORMATION: synthetic

<400> SEQUENCE: 231
tttttttttt tttttccttt agcgcaccac cggttttttt tttttttt                 48

<210> SEQ ID NO 232
<211> LENGTH: 48
<212> TYPE: DNA
<213> ORGANISM: artificial sequence
<220> FEATURE:
<223> OTHER INFORMATION: synthetic

<400> SEQUENCE: 232
tttttttttt tttttgaatc ggccgagtgt tgttttttt tttttttt                  48

<210> SEQ ID NO 233
<211> LENGTH: 25
<212> TYPE: DNA
<213> ORGANISM: artificial sequence
<220> FEATURE:
<223> OTHER INFORMATION: synthetic

<400> SEQUENCE: 233
tttttttttt tttcatcttt gaccc                                          25

<210> SEQ ID NO 234
<211> LENGTH: 50
<212> TYPE: DNA
<213> ORGANISM: artificial sequence
<220> FEATURE:
<223> OTHER INFORMATION: synthetic

<400> SEQUENCE: 234
tttttttttt tttataatca gaaaatcggt gcgggccttt tttttttttt               50

<210> SEQ ID NO 235
<211> LENGTH: 31
<212> TYPE: DNA
<213> ORGANISM: artificial sequence
<220> FEATURE:
<223> OTHER INFORMATION: synthetic

<400> SEQUENCE: 235
gatacaggag tgtactttt tttttttttt t                                    31

<210> SEQ ID NO 236
<211> LENGTH: 48
<212> TYPE: DNA
<213> ORGANISM: artificial sequence
<220> FEATURE:
<223> OTHER INFORMATION: synthetic

<400> SEQUENCE: 236
tttttttttt tttttggcgc agacaatttc aacttttttt tttttttt                 48
```

<210> SEQ ID NO 237
<211> LENGTH: 31
<212> TYPE: DNA
<213> ORGANISM: artificial sequence
<220> FEATURE:
<223> OTHER INFORMATION: synthetic

<400> SEQUENCE: 237
ggaggtttag taccgctttt tttttttttt t                            31

<210> SEQ ID NO 238
<211> LENGTH: 50
<212> TYPE: DNA
<213> ORGANISM: artificial sequence
<220> FEATURE:
<223> OTHER INFORMATION: synthetic

<400> SEQUENCE: 238
tttttttttt tttaccgcca gccataacag ttgaaagttt tttttttttt        50

<210> SEQ ID NO 239
<211> LENGTH: 27
<212> TYPE: DNA
<213> ORGANISM: artificial sequence
<220> FEATURE:
<223> OTHER INFORMATION: synthetic

<400> SEQUENCE: 239
tttttttttt tttttatagc aatagct                                 27

<210> SEQ ID NO 240
<211> LENGTH: 48
<212> TYPE: DNA
<213> ORGANISM: artificial sequence
<220> FEATURE:
<223> OTHER INFORMATION: synthetic

<400> SEQUENCE: 240
aataagtttt gcaagcccaa tagggataa gtatcggatg actatact            48

<210> SEQ ID NO 241
<211> LENGTH: 45
<212> TYPE: DNA
<213> ORGANISM: artificial sequence
<220> FEATURE:
<223> OTHER INFORMATION: synthetic

<400> SEQUENCE: 241
acatagctta catttaacaa taataacgtt gtgctactcc agttc              45

<210> SEQ ID NO 242
<211> LENGTH: 38
<212> TYPE: DNA
<213> ORGANISM: artificial sequence
<220> FEATURE:
<223> OTHER INFORMATION: synthetic

<400> SEQUENCE: 242
cctttttgaa tggcgtcagt attgtgctac tccagttc                     38

<210> SEQ ID NO 243
<211> LENGTH: 38
<212> TYPE: DNA
<213> ORGANISM: artificial sequence
<220> FEATURE:

<223> OTHER INFORMATION: synthetic

<400> SEQUENCE: 243
cgtaaccaat tcatcaacat tttgtgctac tccagttc					38

<210> SEQ ID NO 244
<211> LENGTH: 42
<212> TYPE: DNA
<213> ORGANISM: artificial sequence
<220> FEATURE:
<223> OTHER INFORMATION: synthetic

<400> SEQUENCE: 244
caccaaccga tattcattac cattattgtg ctactccagt tc					42

<210> SEQ ID NO 245
<211> LENGTH: 38
<212> TYPE: DNA
<213> ORGANISM: artificial sequence
<220> FEATURE:
<223> OTHER INFORMATION: synthetic

<400> SEQUENCE: 245
ccaccctcat tttcttgata tttgtgctac tccagttc					38

<210> SEQ ID NO 246
<211> LENGTH: 38
<212> TYPE: DNA
<213> ORGANISM: artificial sequence
<220> FEATURE:
<223> OTHER INFORMATION: synthetic

<400> SEQUENCE: 246
aactttgaaa gaggagaaac attgtgctac tccagttc					38

<210> SEQ ID NO 247
<211> LENGTH: 38
<212> TYPE: DNA
<213> ORGANISM: artificial sequence
<220> FEATURE:
<223> OTHER INFORMATION: synthetic

<400> SEQUENCE: 247
caaggcgcgc cattgccgga attgtgctac tccagttc					38

<210> SEQ ID NO 248
<211> LENGTH: 38
<212> TYPE: DNA
<213> ORGANISM: artificial sequence
<220> FEATURE:
<223> OTHER INFORMATION: synthetic

<400> SEQUENCE: 248
catagccccc ttaagtcacc attgtgctac tccagttc					38

<210> SEQ ID NO 249
<211> LENGTH: 45
<212> TYPE: DNA
<213> ORGANISM: artificial sequence
<220> FEATURE:
<223> OTHER INFORMATION: synthetic

<400> SEQUENCE: 249
tttccctgaa ttacctttttt tacctttttt gtgctactcc agttc					45

```
<210> SEQ ID NO 250
<211> LENGTH: 38
<212> TYPE: DNA
<213> ORGANISM: artificial sequence
<220> FEATURE:
<223> OTHER INFORMATION: synthetic

<400> SEQUENCE: 250
aacggtgtac agactgaata attgtgctac tccagttc                              38

<210> SEQ ID NO 251
<211> LENGTH: 45
<212> TYPE: DNA
<213> ORGANISM: artificial sequence
<220> FEATURE:
<223> OTHER INFORMATION: synthetic

<400> SEQUENCE: 251
gattcgcggg ttagaaccta ccatttgtt gtgctactcc agttc                       45

<210> SEQ ID NO 252
<211> LENGTH: 33
<212> TYPE: DNA
<213> ORGANISM: artificial sequence
<220> FEATURE:
<223> OTHER INFORMATION: synthetic

<400> SEQUENCE: 252
agagtaggat ttcgccaaca tgttttaaaa acc                                   33

<210> SEQ ID NO 253
<211> LENGTH: 33
<212> TYPE: DNA
<213> ORGANISM: artificial sequence
<220> FEATURE:
<223> OTHER INFORMATION: synthetic

<400> SEQUENCE: 253
acggtgacct gtttagctga atataatgcc aac                                   33

<210> SEQ ID NO 254
<211> LENGTH: 33
<212> TYPE: DNA
<213> ORGANISM: artificial sequence
<220> FEATURE:
<223> OTHER INFORMATION: synthetic

<400> SEQUENCE: 254
cgtagcaatt tagttctaaa gtacggtgtt tta                                   33

<210> SEQ ID NO 255
<211> LENGTH: 43
<212> TYPE: DNA
<213> ORGANISM: artificial sequence
<220> FEATURE:
<223> OTHER INFORMATION: synthetic

<400> SEQUENCE: 255
gcttaatgcg ttaaatgtaa atgctgatct tgaaatgagc gtt                        43

<210> SEQ ID NO 256
<211> LENGTH: 43
<212> TYPE: DNA
<213> ORGANISM: artificial sequence
<220> FEATURE:
<223> OTHER INFORMATION: synthetic
```

<400> SEQUENCE: 256
aagccaacgg aatctaggtt gggttatata gattaagcaa ctg    43

<210> SEQ ID NO 257
<211> LENGTH: 43
<212> TYPE: DNA
<213> ORGANISM: artificial sequence
<220> FEATURE:
<223> OTHER INFORMATION: synthetic

<400> SEQUENCE: 257
tttaacaacc gacccaatcg caagacaaaa ttaatctcac tgc    43

<210> SEQ ID NO 258
<211> LENGTH: 43
<212> TYPE: DNA
<213> ORGANISM: artificial sequence
<220> FEATURE:
<223> OTHER INFORMATION: synthetic

<400> SEQUENCE: 258
tttaggccta aattgagaaa acttttttcct tctgttccta gat    43

<210> SEQ ID NO 259
<211> LENGTH: 33
<212> TYPE: DNA
<213> ORGANISM: artificial sequence
<220> FEATURE:
<223> OTHER INFORMATION: synthetic

<400> SEQUENCE: 259
ggtttttaaa acatgttggc gaaatcctac tct    33

<210> SEQ ID NO 260
<211> LENGTH: 33
<212> TYPE: DNA
<213> ORGANISM: artificial sequence
<220> FEATURE:
<223> OTHER INFORMATION: synthetic

<400> SEQUENCE: 260
gttggcatta tattcagcta aacaggtcac cgt    33

<210> SEQ ID NO 261
<211> LENGTH: 33
<212> TYPE: DNA
<213> ORGANISM: artificial sequence
<220> FEATURE:
<223> OTHER INFORMATION: synthetic

<400> SEQUENCE: 261
taaaacaccg tactttagaa ctaaattgct acg    33

<210> SEQ ID NO 262
<211> LENGTH: 43
<212> TYPE: DNA
<213> ORGANISM: artificial sequence
<220> FEATURE:
<223> OTHER INFORMATION: synthetic

<400> SEQUENCE: 262
aacgctcatt tcaagatcag catttacatt taacgcatta agc    43

<210> SEQ ID NO 263
<211> LENGTH: 43

<210> SEQ ID NO 263
<211> LENGTH: 43
<212> TYPE: DNA
<213> ORGANISM: artificial sequence
<220> FEATURE:
<223> OTHER INFORMATION: synthetic

<400> SEQUENCE: 263
cagttgctta atctatataa cccaacctag attccgttgg ctt            43

<210> SEQ ID NO 264
<211> LENGTH: 43
<212> TYPE: DNA
<213> ORGANISM: artificial sequence
<220> FEATURE:
<223> OTHER INFORMATION: synthetic

<400> SEQUENCE: 264
gcagtgagat taattttgtc ttgcgattgg gtcggttgtt aaa            43

<210> SEQ ID NO 265
<211> LENGTH: 43
<212> TYPE: DNA
<213> ORGANISM: artificial sequence
<220> FEATURE:
<223> OTHER INFORMATION: synthetic

<400> SEQUENCE: 265
atctaggaac agaaggaaaa agttttctca atttaggcct aaa            43

<210> SEQ ID NO 266
<211> LENGTH: 63
<212> TYPE: DNA
<213> ORGANISM: artificial sequence
<220> FEATURE:
<223> OTHER INFORMATION: synthetic

<400> SEQUENCE: 266
tggggcgcga gctgaaaagt actcagggca ctgcaagcaa ttgtggtccc aatgggctga    60
gta                                                                 63

<210> SEQ ID NO 267
<211> LENGTH: 79
<212> TYPE: DNA
<213> ORGANISM: artificial sequence
<220> FEATURE:
<223> OTHER INFORMATION: synthetic

<400> SEQUENCE: 267
tgatgagcgt ggatgatact cagcccattg ggtttttttt tttttttttt tttttttttt    60
aggtcatttt tgcggatgg                                                79

<210> SEQ ID NO 268
<211> LENGTH: 67
<212> TYPE: DNA
<213> ORGANISM: artificial sequence
<220> FEATURE:
<223> OTHER INFORMATION: synthetic

<400> SEQUENCE: 268
atacaaaaag cctgtttagt atctactcag ggcactgcaa gcaattgtgg tcccaatggg    60
ctgagta                                                             67

<210> SEQ ID NO 269
<211> LENGTH: 63
<212> TYPE: DNA

```
<213> ORGANISM: artificial sequence
<220> FEATURE:
<223> OTHER INFORMATION: synthetic

<400> SEQUENCE: 269
tactcagccc attgggtttt tttttttttt tttttttttt tttaggtct gagagactac     60 ctt                                                                  63

<210> SEQ ID NO 270
<211> LENGTH: 63
<212> TYPE: DNA
<213> ORGANISM: artificial sequence
<220> FEATURE:
<223> OTHER INFORMATION: synthetic

<400> SEQUENCE: 270
tggggcgcga gctgaaaaga taccagtcta ttcaattggg cccgtccgta tggtgggtgt     60
gct                                                                  63

<210> SEQ ID NO 271
<211> LENGTH: 63
<212> TYPE: DNA
<213> ORGANISM: artificial sequence
<220> FEATURE:
<223> OTHER INFORMATION: synthetic

<400> SEQUENCE: 271
agcacaccca ccatactttt tttttttttt tttttttttt ttttaggtca tttttgcgga     60
tgg                                                                  63

<210> SEQ ID NO 272
<211> LENGTH: 67
<212> TYPE: DNA
<213> ORGANISM: artificial sequence
<220> FEATURE:
<223> OTHER INFORMATION: synthetic

<400> SEQUENCE: 272
atacaaaaag cctgtttagt atcataccag tctattcaat tgggcccgtc cgtatggtgg     60
gtgtgct                                                              67

<210> SEQ ID NO 273
<211> LENGTH: 79
<212> TYPE: DNA
<213> ORGANISM: artificial sequence
<220> FEATURE:
<223> OTHER INFORMATION: synthetic

<400> SEQUENCE: 273
tgatgagcat ggcatcagca cacccaccat acttttttt tttttttttt tttttttttt     60
aggtctgaga gactacctt                                                 79

<210> SEQ ID NO 274
<211> LENGTH: 63
<212> TYPE: DNA
<213> ORGANISM: artificial sequence
<220> FEATURE:
<223> OTHER INFORMATION: synthetic

<400> SEQUENCE: 274
tggggcgcga gctgaaaagt actcagggca ctgcaagcaa ttgtggtccc aatgggctga     60
gta                                                                  63
```

```
<210> SEQ ID NO 275
<211> LENGTH: 71
<212> TYPE: DNA
<213> ORGANISM: artificial sequence
<220> FEATURE:
<223> OTHER INFORMATION: synthetic

<400> SEQUENCE: 275
acctagtgta ctcagcccat tgggtttttt tttttttttt tttttttttt ttaggtcatt      60
tttgcggatg g                                                          71

<210> SEQ ID NO 276
<211> LENGTH: 67
<212> TYPE: DNA
<213> ORGANISM: artificial sequence
<220> FEATURE:
<223> OTHER INFORMATION: synthetic

<400> SEQUENCE: 276
atacaaaaag cctgtttagt atcataccag tctattcaat tgggcccgtc cgtatggtgg      60
gtgtgct                                                               67

<210> SEQ ID NO 277
<211> LENGTH: 71
<212> TYPE: DNA
<213> ORGANISM: artificial sequence
<220> FEATURE:
<223> OTHER INFORMATION: synthetic

<400> SEQUENCE: 277
tacggagtag cacacccacc atacttttt tttttttttt tttttttttt ttaggtctga       60
gagactacct t                                                          71

<210> SEQ ID NO 278
<211> LENGTH: 48
<212> TYPE: DNA
<213> ORGANISM: artificial sequence
<220> FEATURE:
<223> OTHER INFORMATION: synthetic

<400> SEQUENCE: 278
aagtatggtg ggtgtgctga tgccattttt tagtatagtc atccgata                  48

<210> SEQ ID NO 279
<211> LENGTH: 48
<212> TYPE: DNA
<213> ORGANISM: artificial sequence
<220> FEATURE:
<223> OTHER INFORMATION: synthetic

<400> SEQUENCE: 279
aacccaatgg gctgagtatc atccactttt tagtatagtc atccgata                  48

<210> SEQ ID NO 280
<211> LENGTH: 48
<212> TYPE: DNA
<213> ORGANISM: artificial sequence
<220> FEATURE:
<223> OTHER INFORMATION: synthetic

<400> SEQUENCE: 280
aagtatggtg ggtgtgctac tccgtatttt tagtatagtc atccgata                  48
```

```
<210> SEQ ID NO 281
<211> LENGTH: 52
<212> TYPE: DNA
<213> ORGANISM: artificial sequence
<220> FEATURE:
<223> OTHER INFORMATION: synthetic

<400> SEQUENCE: 281
cccaatgggc tgagtatcat ccacgctcat catttttgaa ctggagtagc ac          52

<210> SEQ ID NO 282
<211> LENGTH: 52
<212> TYPE: DNA
<213> ORGANISM: artificial sequence
<220> FEATURE:
<223> OTHER INFORMATION: synthetic

<400> SEQUENCE: 282
gtatggtggg tgtgctgatg ccatgctcat catttttgaa ctggagtagc ac          52

<210> SEQ ID NO 283
<211> LENGTH: 15
<212> TYPE: DNA
<213> ORGANISM: artificial sequence
<220> FEATURE:
<223> OTHER INFORMATION: synthetic

<400> SEQUENCE: 283
gaactggagt agcac                                                   15
```

SYSTEMS COMPRISING NON-IMMUNOGENIC AND NUCLEASE RESISTANT NUCLEIC ACID ORIGAMI DEVICES FOR MOLECULAR COMPUTATION

FIELD OF THE INVENTION

The present invention relates in general to systems of molecular origami devices and their uses for molecular computing, quorum sensing and programmable drug delivery.

BACKGROUND OF THE INVENTION

Inspired by communication mechanisms occurring in biological systems, molecular communication (MC) is a novel interdisciplinary paradigm in which the research areas of biotechnology, communication technology and nanotechnology converge [Hiyama, S. et al., 2005]. The rapid advances in these fields have brought about the miniaturization of mobile machines and robots down to nanometer dimensions. At this scale, a bio-inspired nanorobot (nanobot in short) is the most basic functional unit, consisting of nanoscale components, that is capable of performing specific tasks such as computing, data storing, sensing or actuation [Llatser, I. et al., 2012]. Such tasks can be executed through the capacity of receiving inputs and generating outputs, which in a molecular communication context requires transceiver capabilities, as nanobots receive information by reacting to specific molecules and broadcast information by releasing other molecules, according to predefined parameters.

To date, different MC systems have been proposed depending on the way message molecules propagate from transmitters to receivers [Pierobon, M. et al., 2010]. These systems have been categorized into three classifications: walkway-based, diffusion based and flow-based MC. For each category, several efforts have been undertaken to design systems and laboratory condition feasibility has been investigated [Hiyama, S. et al., 2010]. For walkway-based MC systems, a walkway-motor-interaction transport model has been proposed [Hiyama, S. et al., 2009]. In such systems, signal molecules are propagated over protein filaments (i.e. microtubules) via molecular motors [Hiyama, S. et al., 2007; Hiyama, S. et al., 2008 (a); Hiyama, S. et al., 2008 (b); Enomoto, A. et al., 2006]. Diffusion-based MC is achieved by encapsulating information molecules into vesicles that are emitted into a medium [Moritani, Y. et al., 2006; Moritani, Y. et al., 2007] where they subsequently propagate via diffusion or unpredicted turbulence of the medium. This approach also includes systems utilizing diffusion through gap-junctions between cells [Nakano, T. et al., 2005; Walsh, F. et al., 2010] and long range systems that are envisioned to make use of platforms such as hormones, pheromones, pollen or spores [Parcerisa Gine, L. et al., 2009]. There have also been accounts of a new group of longer range, actively propelled systems utilizing flagellated bacteria [Gregori, M. et al., 2011; Gregorim M. et al., 2010] and catalytic nanomotor [Gregori, M. et al., 2010] systems in which information is encoded in DNA plasmids and transmitted via bacteria or synthetic nanomotors. In flow based MC systems, signal molecules are released into a fluid medium where they are guided to their destination via currents or drifts. Such systems offer some of the most biologically realistic scenarios; i.e. as nanomachines can be deployed in flows which introduce a drift for the motion of signal molecules, such as in hormonal communication through the blood stream. Interestingly, even though vesicle and long range hormones, pheromones, pollen or spores systems might be applicable in flow guided MC systems, no research on physical systems employing such propagation systems has been published.

The fundamental challenge is to devise a biological nanobot platform that can combine the extraordinary characteristics of nano-transceivers with application-orientated functionality. Ultimately such a system will provide the blue print for a scalable single network system that can interconnect large numbers of nanobots to perform complex tasks.

General efforts in MC research have mainly focused on bio-inspired propagation systems and theoretical qualification thereof, whilst research on actual transceivers has been fairly limited. To date, two transceiver engineering approaches have been proposed; the construction of simplified artificial cell-like structures made of biological materials or adaptation of existing biological cells [Suda, T. et al., 2008]. In comparison, the DNA-origami platform, disclosed in WO 2012/061719 and Douglas et al. (2012), herein incorporated by reference as if fully described herein, sanctions a novel non-cell like approach to construct autonomous, logic-guided nanobots, that can be programmed to transport molecular payloads to targets.

SUMMARY OF INVENTION

The present application is based on the copending PCT application titled "Non-Immunogenic and Nuclease Resistant Nucleic Acid Origami Devices And Compositions Thereof" of the same applicant, filed on Apr. 13, 2013, and claims priority from U.S. Provisional Patent Application No. 61/813,412 filed Apr. 18, 2013, of which some of the present inventors are co-inventors, herein incorporated by reference as if fully described herein.

In one aspect, the present invention relates to a system acting as a logic gate, said system comprising at least one effector device, at least one regulator device, at least one input and at least one output, wherein each one of said at least one effector device and at least one regulator device each is a nucleic acid origami device comprising a scaffold strand and a plurality of staple strands, and independently has the structure A, B or C, wherein in the structure A: (i) one of the staple strands comprises either (a) an aptamer domain capable of binding to a binding partner comprising one of said at least one input; (b) an oligonucleotide capable of binding a DNA binding protein, said DNA binding protein comprising another of said at least one input; or (c) an oligonucleotide attached to a nano-antenna capable of receiving an electromagnetic field comprising still another of said at least one input, or one of the staple strands comprises an aptamer domain of (a) and another of the staple strands comprises an oligonucleotide of (c); (ii) another of the staple strands comprises a latch domain hybridized or bound to said aptamer domain of (a) or oligonucleotide of (b) or (c), the latch domain sequence being selected such that the aptamer domain of (a) is capable of binding to the binding partner such that the binding partner displaces the latch domain, or the latch domain is capable of hybridizing with an external oligonucleotide selected such that it displaces the aptamer domain; said latch domain is linked to a binding partner that is selected such that it has a first configuration under a first condition and a different second configuration under a second condition, and the aptamer of (a) or the oligonucleotide of (b) is capable of binding to the binding partner having the first configuration but incapable of binding to the binding partner having the second configuration such that the latch domain is displaced from the aptamer of (a) or the oligonucleotide of (b) when the binding partner transitions from the first to the second configuration; or the nano-antenna of (c), upon receipt of said electromagnetic field, undergoes inductive coupling and subsequent heating thereby displacing the latch domain from the oligonucleotide of (c); and (iii) the aptamer domain of (a) or the oligonucleotide of (b) or (c), and the latch domain, when hybridized or bound to one another, hold the device in a closed configuration; and the device transitions to an open configuration when said aptamer domain or oligonucleotide, and the latch domain, are not hybridized or bound to one another, in the structure B: (i) one of the staple strands comprises a first aptamer domain capable of binding to a first binding partner comprising one of said at least one input; (ii) another of the staple strands comprises a second aptamer domain capable of binding to a second binding partner comprising another one of said at least one input; (iii) still another of the staple strands comprises a first latch domain hybridized to the first aptamer domain, the first latch domain sequence being selected such that the first aptamer domain is capable of binding to the first binding partner such that the first binding partner displaces the first latch domain, or the first latch domain is capable of hybridizing with an external oligonucleotide selected such that it displaces the aptamer domain; (iv) yet another of the staple strands comprises a second latch domain hybridized to the second aptamer domain, the second latch domain sequence being selected such that the second aptamer domain is capable of binding to the second binding partner such that the second binding partner displaces the second latch domain or the second latch domain is capable of hybridizing with an external oligonucleotide selected such that it displaces the aptamer domain; and (v) said nucleic acid origami device is in a closed configuration when the first aptamer domain is hybridized to the first latch domain and/or the second aptamer domain is hybridized to the second latch domain; and the device transitions to an open configuration when the first aptamer domain is not hybridized to the first latch domain and the second aptamer domain is not hybridized to the second latch domain, in the structure C: (i) two of the staple strands each comprises a latch domain linked to an oligonucleotide capable of hybridizing with an external oligonucleotide, said external oligonucleotides are positioned on another one of said nucleic acid origami devices; and; (ii) said nucleic acid origami device is in an open configuration when each one of the oligonucleotides capable of hybridizing with an external oligonucleotide is not hybridized to said external oligonucleotide; and the device transitions to a closed configuration when both of said oligonucleotides capable of hybridizing with an external oligonucleotide are hybridized to said external oligonucleotides, wherein each one of said at least one effector nucleic acid origami device and at least one regulator nucleic acid origami device is either alkylated, acylated or hydroxylated, or interacts with a compound capable of non-covalently binding to the major- or minor-groove of a double stranded nucleic acid, and therefore is resistant to nucleases, and/or each one of said at least one effector nucleic acid origami device and at least one regulator nucleic acid origami device lacks TLR9 recognition elements or the TLR9 recognition elements of said nucleic acid origami device are masked or modified and therefore said nucleic acid origami device is non-immunogenic.

In certain embodiments, the system of the present invention comprises one effector device having one or more handle domains each bound to a payload, at least one regulator device, at least one input and one output, wherein said output has a first output state when said effector device is in the closed configuration and a second output state when said effector device is in the open configuration. More particularly, the first output state corresponds to a logical off state and the second output state corresponds to a logical on state. Specific logical gates based on such a system are (i) a logical NAND gate, comprising two inputs and being in a logical on state if both inputs are present; (ii) a logical NOT gate, comprising one input and being in a logical on state if the input is absent; (iii) a logical implicit OR gate, comprising two inputs and being in a logical on state if at least one of the two inputs is present; and (iv) a logical exclusive OR (XOR) gate, comprising two inputs and being in a logical on state if only one of the two inputs is present, i.e., if the first of said two inputs is present and the second of said two inputs is absent, or the second of said two inputs is present and the first of said two inputs is absent.

In certain embodiments, the system of the present invention comprises two effector devices each having one or more handle domains each bound to a payload, at least one regulator device, at least one input and two outputs, wherein the first of said two outputs has a first output state when the first of said two effector devices is in the closed configuration and a second output state when the first of said two effector devices is in the open configuration; and the second of said two outputs has a first output state when the second of said two effector devices is in the closed configuration and a second output state when the second of said two effector devices is in the open configuration. In a system having this configuration, each one of said first output states corresponds to a logical off state and each one of said second output states corresponds to a logical on state. Specific logical gates based on such a system are (i) a logical controlled NOT gate, comprising two inputs and two outputs, wherein the first output acts as a XOR gate and is in a logical on state if only one of the two inputs is present, and the second output is sensitive to the presence of the first of said two inputs only and it is thus in a logical on state if either only the first of said two inputs or both inputs are present.

According to the present invention, whenever the system, i.e., the logic gate, of the invention is in a logical on state, irrespectively to the specific configuration of that system, the effector device comprised in the system is in an open configuration and each one of the payloads is positioned on an outer surface of said effector device.

In another aspect, the present invention relates to a system exhibiting quorum sensing comprising a plurality of effector nucleic acid origami devices each having the structure A, B or C as defined above in connection with the system acting as a logic gate or, alternatively, a plurality of a member each selected from a liposome, a particle or an artificial cell; at least one input; and at least one output, wherein said plurality of effector nucleic acid origami devices or members aggregates at a predetermined concentration, and wherein: each one of the effector nucleic acid origami devices comprises said handle domain bound to a first oligonucleotide capable of hybridizing with said aptamer domain of another of said effector nucleic acid origami devices and positioned on the outer surface of the device when the device is in the closed configuration; or each one of the members comprises on an outer surface thereof (a) a staple strand comprising a handle domain bound to a first oligonucleotide; and (b) a further staple strand comprising a second oligonucleotide selected such that it is capable of hybridizing to a first oligonucleotide of another of said plurality of members, each one of said effector nucleic acid origami devices or members having on open and a closed configuration and is initially in the closed configuration.

In a further aspect, the present invention provides a pharmaceutical composition comprising a system acting as a logic gate or a system exhibiting quorum sensing as defined above, and a pharmaceutically acceptable carrier.

DETAILED DESCRIPTION OF THE INVENTION

Computers capable of controlling molecules in a living organism could lead to a paradigm shift in how therapeutics are designed and used, had a proper interface been designed. The challenge of designing a computer-molecule interface is avoided when the computer itself is built from molecules, with computations driven by molecular forces [Adamatzky, A. et al., 2002]. DNA is a natural substrate for such a task, and DNA computing has been successfully demonstrated in a diverse set of purely mathematical-computational settings [Adleman, L. M. et al., 1994; Braich, R. S. et al., 2002; Yeh, C. W. et al., 2006; Chen, J. H. et al., 1991; Seeman, N. C., 1982; Winfree, E. et al., 1998; Rothemund, P. W., 2006; Adar, R. et al., 2004; Chang, W. L. et al., 2004; Qian, L. et al., 2011; Yin, Z. et al., 2002]. As a biomolecule, DNA also provides a natural conduit to affect genes, proteins and whole cells, although literature in this field is scarce. Benenson, Shapiro and colleagues have described elegant nucleic acid based computers, which generate logical outputs upon recognizing defined gene expression patterns [Xie, Z. et al., 2011; Rinaudo, K. et al., 2007; Benenson, Y. et al., 2004; Benenson, Y. et al., 2001]. Recently, we have used DNA origami [Rothemund, P. W., 2006; Dietz, H. et al., 2009; Douglas, S. M. et al., 2009] to fabricate an autonomous, logic guided nanorobot capable of delivering therapeutic payloads to the surface of target cells (WO 2012/061719).

The current work aims at setting interactions or collisions between these bio-responsive nanorobots to produce computations of higher complexity for controlling molecules. Collision-based computing is driven by the interactions between discrete mobile objects such as billiard balls, particles or solitons in nonlinear media [Adamatzky, A., 2002]. The DNA nanorobots disclosed herein provide a fit platform for universal collision-based computing if collisions can be designed to logically determine the state of the nanorobot carrying the effector payload.

Figure 4A:
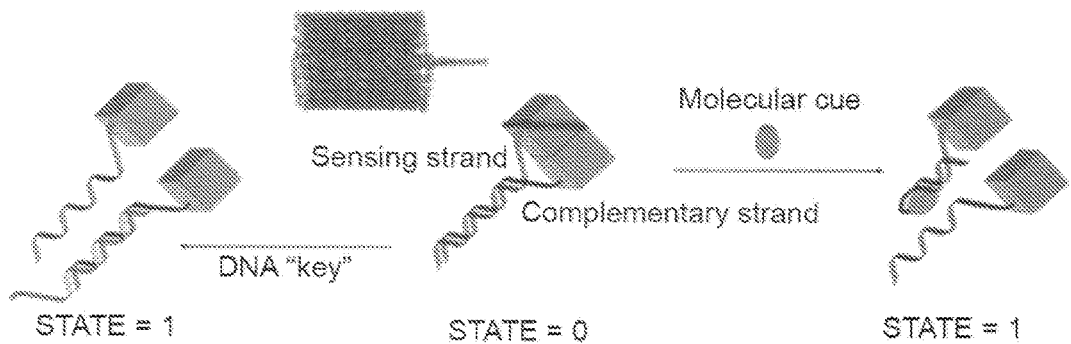
FIGS. 4A-F show gates mechanism for collision-based computing. (A) The nanorobot gate consists of two "arms", each comprised of a sensing strand hybridized to a complementary strand. Opening of the gate can be achieved by two modes: by a molecular cue (e.g. a protein, nucleic acid fragment, small molecule etc.) binding to the sensing strand (right), or by a DNA key presented by an adjacent nanorobot, hybridizing to the complementary strand and displacing the sensing strand by toehold-mediated strand migration. The DNA key can be presented by an adjacent nanorobot only when the latter is in state 1; nanorobots in state 0 cannot present any payload; (B) AND emulated by E architecture. The solitary E nanorobot turns to state 1 when it encounters both molecular cues k1 (in this case—platelet-derived growth factor (PDGF)) and k2 (in this case—vascular endothelial growth factor (VEGF)), which are received by its sensing arms (k1* and k2*, respectively). Binding of only one of the cues is not sufficient for complete nanorobot opening. Therefore, the output generated by E is AND; (C) OR emulated by EP1P2 architecture. Here P1 and P2 are added to E (here only P1 is shown for clarity). P1 and P2 require only one of the molecular cues k1 or k2, respectively, to turn to state 1. Once in state 1, either P1 or P2 can collide with E and present it with the DNA key necessary for opening of the reciprocal gate. For instance, if only k1 is present, P1 would turn to state 1 (by sensing k1 through k1*) and present to E the DNA key necessary to open gate k2*. Therefore, collisions between E and P1 (or P2) lead to a complex EP1 or EP2 in which E is at state 1, emulating an OR output; (D) XOR emulated by EP1P2N architecture. Here N is added to EP1P2 (here only P1 is shown for clarity). Similar to E, N requires both cues k1 and k2 to open, but unlike E, the DNA keys presented by P1 and P2 do not open N (since the complementary strands of N are different than those of E). The payload presented by N is DNA strands which clasp both ends of E, preventing it from opening (or promoting closure of E when it is already open). Therefore, when either k1 or k2 are present, E is at state 1 (owing to P1 and P2), but when both k1 and k2 are present, it is pushed to state 0 by N. This emulates XOR output; (E) NAND emulated by $E_{open}N$ architecture. Here, $E_{open}$ (nanorobots which lack sensing arms and are therefore constantly in state 1) are mixed with N. Only when both k1 and k2 are present, N turns to state 1 and induce closure of $E_{open}$. This emulates a NAND output; and (F) NAND-constructed inverter by $E_{open}N×$architecture. Here, N has only one cue required for turning to state 1. When the cue k1 is present, N closes E, emulating an inverter based on the NAND gate shown above.

The state of a single nanorobot can be either closed (0) or open (1) controlled by the nanorobot gate [Douglas, S. M. et al., 2012], equivalent to an AND gate. Each of the two "arms" in the gate (one for each input) consists of a sensing strand (e.g. an aptamer to a specific cue) and a complementary strand; when these hybridize, they hold the nanorobot at state 0. To enable state-determining collisions between an "effector" nanorobot and a "regulator" nanorobot, the gate system was re-designed as follows. The gate typically opens only in response to the chosen cue, which displaces the complementary strand from the sensing stand. However, in the current design, the gate opens also in response to an external DNA "key", which hybridizes with the complementary strand, displacing the sensing strand by toehold-mediated migration [Zhang, D. Y. et al., 2011; Zhang, D. Y. et al., 2009] (FIG. 4A). This external, cue-independent key to the effector nanorobot gate, is loaded as cargo into a regulator nanorobot, such that when the latter is at state 1, a collision between the two will subsequently alter the former's state from 0 to 1. This assigns a "positive regulator" (P) phenotype to the nanorobot holding the external key. To design a "negative regulator" (N) phenotype as well, the regulator nanorobot is loaded with DNA strands that clasp two juxtaposed sides of the effector (E) nanorobot, thereby forcing it to close or preventing it from becoming open. Once E, P and N nanorobots have been designed and fabricated, various architectures can be achieved by mixing the proper types at defined stoichiometries in the presence or absence of their cognate cues.

Figure 4B:
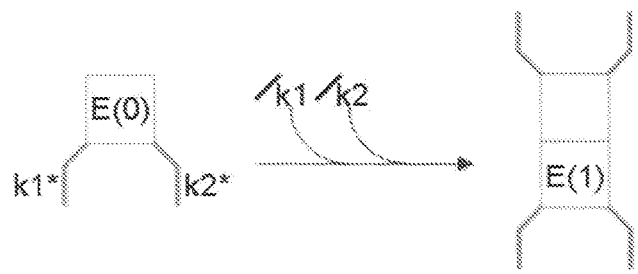
Figure 4C:
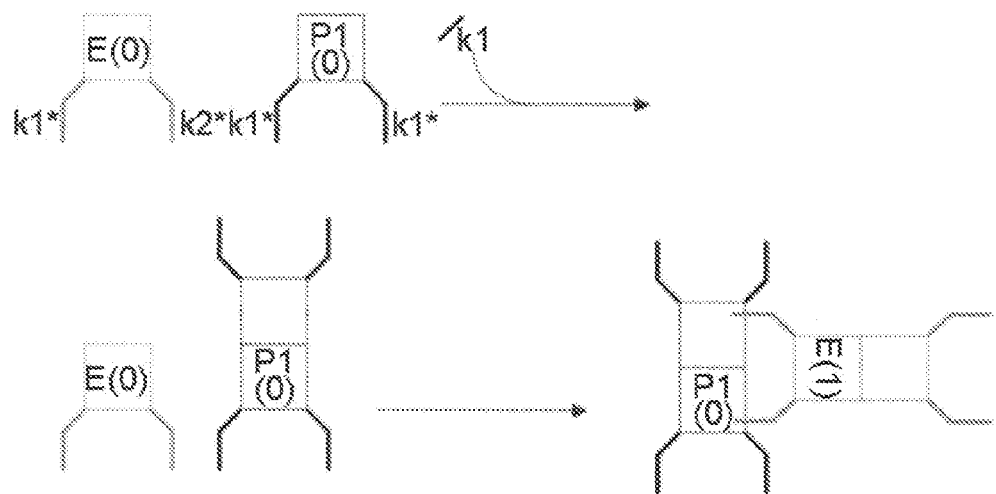

Consider type E nanorobots carrying a payload and controlled by a gate, which opens if and only if both proteins X and Y are present. An architecture consisting only of E nanorobots (termed E architecture) would emulate a logical AND gate as previously described [Douglas, S. M. et al., 2012] (FIG. 4B). Now consider two additional nanorobot types, P1 (opens in response to X and carries the key to the Y arm of E) and P2 (opens in response to Y and carries the key to the X arm of E). Adding P1 and P2 to E (EP1P2 architecture) ensures the latter opens in response to X alone (by P1), Y alone (by P2), or XY (by itself), emulating a logical OR gate (FIG. 4C).

We now add type N nanorobots to the system described thus far (EP1P2N architecture), N being activated if and only if both X and Y are present. Here, in contrast to EP1P2, the presence of both X and Y activates N, which simultaneously negates or prevents the activation of E. These outputs are identical to the ones generated by the logical XOR gate (FIG. 1D). It is important to remember that in architectures EP1P2 and EP1P2N, E at its final state is always in complex with P1, P2 or N.

Architectures based on more than one effector nanorobot (like the EFP1P2N mentioned above) enable to relay output bits to additional therapeutic molecules, forming the basis for more complex gates, reversible logic and binary decoders. To demonstrate such architecture, a controlled NOT (CNOT) gate was designed, consisting of E, P1, P2 and N as described above, and in addition a second effector nanorobot, F, not negated by N, and a positive regulator nanorobot P3 that responds only to X and keys only F. Thus, one input bit is XORed by E and the second output bit is mapped unchanged by F.

Of particular importance is the emulation of functionally complete gates, such as NAND and NOR, which can be cascaded to build any other gate. NAND architecture can be based on two nanorobot types: Eopen, which is similar to E but lacks gate strands, hence it is constitutively open regardless of the inputs X and Y; and N, which opens in response to XY and negates Eopen as a result. This architecture therefore produces 0 in response to XY, and 1 otherwise.

We have recently proposed an actuating DNA device, to which the drug is tethered, logically switching the drug between two states—unavailable ("off") and available ("on"), without actually releasing it [Douglas, S. M. et al., 2012]. By constructing various types of DNA logic gates based on aptamer recognition, strand displacement etc., such devices could be programmed to respond to diverse stimuli in many defined ways. Still, even the design described thus far does not take advantage of the more elaborate modes of control provided by multi-agent systems exhibiting collective behaviors.

The present invention is based, inter alia, on the finding disclosed in Example 2, that the utilization of a great number of different nucleic acid origami devices, some acting as effector devices because they carry a payload, such as fluorescent molecule, biotin or avidin, and some acting as regulator devices because in their active state they are capable of interacting with the effector devices by way of their oligonucleotide payload and either turning them on or off, in specific predetermined architectures, can act as any important logical gate. For example, it has been found in accordance with the present invention that certain combinations of effector and regulator nucleic acid origami devices exhibit logical AND, OR, XOR, NAND, NOT and CNOT behavior. These different gates can be combined to form any logical circuit required in order to present one or more payloads, such as a drug or combination of different drugs, under specific circumstances that may be defined in terms of the presence of specific ligands or enzymes, or certain environmental determinants such as pH. Since the nucleic acid origami devices can circle between an open and a closed configuration, and since the payload may be bound to the device via a linker and presented when the device is in the open configuration without being released, not only the delivery of a drug may be controlled but also the withdrawal of the drug.

Thus, in one aspect, the present invention relates to a system acting as a logic gate, said system comprising at least one effector device, at least one regulator device, at least one input and at least one output, wherein each one of said at least one effector device and at least one regulator device each is a nucleic acid origami device comprising a scaffold strand and a plurality of staple strands, and independently has the structure A, B or C, wherein in the structure A (this structure has one key: either an aptamer, a nano-antenna or a "ligand-sensing molecule"-type key): (i) one of the staple strands comprises either (a) an aptamer domain capable of binding to a binding partner comprising one of said at least one input; (b) an oligonucleotide capable of binding a DNA binding protein, said DNA binding protein comprising another of said at least one input; or (c) an oligonucleotide attached to a nano-antenna capable of receiving an electromagnetic field comprising still another of said at least one input, or one of the staple strands comprises an aptamer domain of (a) and another of the staple strands comprises an oligonucleotide of (c); (ii) another of the staple strands comprises a latch domain hybridized or bound to said aptamer domain of (a) or oligonucleotide of (b) or (c), the latch domain sequence being selected such that the aptamer domain of (a) is capable of binding to the binding partner such that the binding partner displaces the latch domain, or the latch domain is capable of hybridizing with an external oligonucleotide selected such that it displaces the aptamer domain; said latch domain is linked to a binding partner that is selected such that it has a first configuration under a first condition (comprising one of said at least one inputs) and a different second configuration under a different second condition (comprising another of said at least one inputs), and the aptamer of (a) or the oligonucleotide of (b) is capable of binding to the binding partner having the first configuration but incapable of binding to the binding partner having the second configuration such that the latch domain is displaced from the aptamer of (a) or the oligonucleotide of (b) when the binding partner transitions from the first to the second configuration; or the nano-antenna of (c), upon receipt of said electromagnetic field, undergoes inductive coupling and subsequent heating thereby displacing the latch domain from the oligonucleotide of (c); and (iii) the aptamer domain of (a) or the oligonucleotide of (b) or (c), and the latch domain, when hybridized or bound to one another, hold the device in a closed configuration; and the device transitions to an open configuration when said aptamer domain or oligonucleotide, and the latch domain, are not hybridized or bound to one another, in the structure B (this structure has two different aptamer keys): (i) one of the staple strands comprises a first aptamer domain capable of binding to a first binding partner comprising one of said at least one input; (ii) another of the staple strands comprises a second aptamer domain capable of binding to a second binding partner comprising another one of said at least one input; (iii) still another of the staple strands comprises a first latch domain hybridized to the first aptamer domain, the first latch domain sequence being selected such that the first aptamer domain is capable of binding to the first binding partner such that the first binding partner displaces the first latch domain, or the first latch domain is capable of hybridizing with an external oligonucleotide selected such that it displaces the aptamer domain; (iv) yet another of the staple strands comprises a second latch domain hybridized to the second aptamer domain, the second latch domain sequence being selected such that the second aptamer domain is capable of binding to the second binding partner such that the second binding partner displaces the second latch domain, or the second latch domain is capable of hybridizing with an external oligonucleotide selected such that it displaces the aptamer domain; and (v) said nucleic acid origami device is in a closed configuration when the first aptamer domain is hybridized to the first latch domain and/or the second aptamer domain is hybridized to the second latch domain; and the device transitions to an open configuration when the first aptamer domain is not hybridized to the first latch domain and the second aptamer domain is not hybridized to the second latch domain, in the structure C (this structure is initially open and is closed by external oligonucleotides on another nanobot): (i) two of the staple strands each comprises a latch domain linked to an oligonucleotide capable of hybridizing with an external oligonucleotide, said external oligonucleotides are positioned on another one of said nucleic acid origami devices; and (ii) said nucleic acid origami device is in an open configuration when each one of the oligonucleotides capable of hybridizing with an external oligonucleotide is not hybridized to said external oligonucleotide; and the device transitions to a closed configuration when both of said oligonucleotides capable of hybridizing with an external oligonucleotide are hybridized to said external oligonucleotides, wherein each one of said at least one effector nucleic acid origami device and at least one regulator nucleic acid origami device is either alkylated, acylated or hydroxylated, or interacts with a compound capable of non-covalently binding to the major- or minor-groove of a double stranded nucleic acid, and therefore is resistant to nucleases, and/or each one of said at least one effector nucleic acid origami device and at least one regulator nucleic acid origami device lacks TLR9 recognition elements or the TLR9 recognition elements of said nucleic acid origami device are masked or modified and therefore said nucleic acid origami device is non-immunogenic.

The terms "nucleic acid origami device", "nanorobot", "nanobot", and simply "device", used herein interchangeably in connection with the effector devices and regulator devices composing the logic gate of the present invention refer to a nucleic acid, e.g., a DNA, origami device as defined above, in any one of the configurations described below.

The term "scaffold strand" as used herein refers to a long nucleic acid, e.g., DNA, strand, for example about 7250 bases long, that may be folded into a particular shape using a plurality of rationally designed "staple" DNA strands. However, there is no principal limit to the length of scaffold strand; it all depends on the size of device you want to build, so the scaffold strand could have any length between 15 and $10^{13}$ bases. The sequences of the staple strands are designed such that they hybridize to particular portions of the scaffold strands and, in doing so, force the scaffold strands into a particular shape. Methods useful in the making of DNA origami structures can be found, e.g., in Rothemund, P. W., Nature 440:297-302 (2006); Douglas et al., Nature 459:414-418 (2009); Dietz et al., Science 325:725-730 (2009); and US Patent Publication Nos. 2007/0117109, 2008/0287668, 20100069621 and 2010/0216978, each of which is incorporated by reference in its entirety. Staple design can be facilitated using, e.g., CADnano software, available at http://www.cadnano.org.

The term "latch domain" as used herein refers to a nucleic acid domain capable of hybridizing to an opposing aptamer domain or other nucleic acid (e.g., attached to a nano-antenna) and thereby holds the nucleic acid origami device in a closed configuration.

The term "aptamer domain" as used herein refers to a nucleic acid molecule selected such that it is capable of specifically binding a target molecule, much like an antibody is capable of specifically binding an antigen. Aptamers can be designed to target essentially any antigen of interest using methods known in the art. For example, methods of designing aptamers specific for a target of interest can be found in U.S. Pat. Nos. 5,582,981, 5,756,291, 5,840,867 and 7,745,607, and in Tang et al., Anal. Chem. 79:4900-4907 (2007), each of which are incorporated by reference in their entirety.

A non-limiting example of a "oligonucleotide capable of binding a DNA binding protein" is an isolated response element originally found within a gene promoter. A specific example is the glucose responsive regulatory element.

The terms "hybridized" or "hybridizing" as used herein refer to the binding of two strands of nucleic acid molecules to each other, and are meant to include that the two strands are capable of hybridizing to each other, or that the two strands are complementary to each other, wherein the complementarity of the two strands may vary in order to calibrate the affinity between the two strands. For example, each one of the two strands may have a sequence of base pairs that is 100, 99, 98, 96, 94, 92, 90, 85, 80, 75, 70, 65 or 60% complementary to the sequence of the other strand.

The aptamer domain is capable of binding to a binding partner such that the binding partner displaces the latch domain. In the case the binding partner is a ligand such as a target antigen that binds to the aptamer by inducing a structural change in the aptamer domain enabling it to bind to the ligand, the ligand binds to the aptamer domain at a higher affinity than the latch domain causing the aptamer to lose its linear configuration that enables it to hybridize with the latch domain, and therefore releases the latch domain. In case the binding partner is a nucleic acid molecule, the nucleic acid molecule may have a higher degree of complementarity with the aptamer domain than has the latch domain and therefore displaces the latch domain. Conceptually, the nucleic acid molecule could be complementary to the latch domain and bind to it, thus displacing the aptamer domain. In both cases, the displacement would lead to the transitions of the device from a closed to an open configuration. In all embodiments wherein it is defined that the binding partner binds to the aptamer domain such that the binding partner displaces the latch domain, it should be understood that, in the case of the binding partner being an oligonucleotide, the binding partner may alternatively bind to the latch domain such that oligonucleotide displaces the latch domain.

The term "external oligonucleotide" as used herein refers to an oligonucleotide that is not comprised within a particular device being defined, but is found e.g. on a neighboring identical or different device.

The term "nuclease" as used herein refers to an enzyme capable of cleaving the phosphodiester bonds between the nucleotide subunits of nucleic acids. Nucleases are usually further divided into endonucleases and exonucleases, although some of the enzymes may fall in both categories. Well known nucleases are deoxyribonuclease and ribonuclease.

The term "resistant to nucleases" as used herein refers to nucleic acid molecules that have been modified so that they are more stable in the presence of nucleases than unmodified molecules.

The term "TLR9 recognition element" as used herein refers to elements on a nucleic acid molecule, e.g., a nucleic acid molecule, that are recognized by Toll Like Receptor (TLR) 9 present in the cytoplasm of antigen presenting cells. TLR9 is expressed by numerous cells of the immune system such as dendritic cells, B lymphocytes, monocytes and natural killer (NK) cells. TLR9 is expressed intracellularly, within the endosomal compartments and functions to alert the immune system of viral and bacterial infections by binding to DNA rich in CpG motifs. TLR9 signals leads to activation of the cells initiating pro-inflammatory reactions that result in the production of cytokines such as type-I interferon and IL-12.

The terms "CpG motif" and "CpG island" are used interchangeably herein and refer to short single-stranded synthetic nucleic acid molecules that contain a cytidine triphosphate deoxynucleotide ("C") followed by a guanidine triphosphate deoxynucleotide ("G"). The "p" refers to the phosphodiester link between consecutive nucleotides, although some DNA nucleic acids have a modified phosphorothioate (PS) backbone instead.

The term "masked nucleic acid origami device" refers to a device that is linked to a molecule capable of covering domains otherwise accessible to the environment, such as CpG islands and thereby making these domains inaccessible to the environment.

The term "non-immunogenic" as used herein refers to a molecule that does not induce a response against it by the immune system in a mammal, or induces a weaker response than would have been induced by the same molecule that differs only in that it has TLR9 recognition elements that have not been masked or modified.

Examples of non-covalent binding are binding involving ionic bonds, electrostatic interactions, hydrophobic interactions, hydrogen bonds or van der Waals forces.

In one embodiment, in at least one of the nucleic acid origami devices composing the logic gate of the present invention and having the structure A: (i) one of the staple strands comprises a first aptamer domain and another of the staple strands comprises a second aptamer domain wherein both aptamer domains are capable of binding to identical binding partners; (ii) still another of the staple strands comprises a first latch domain hybridized to the first aptamer domain and selected such that the first aptamer domain is capable of binding to the binding partner such that the binding partner displaces the first latch domain; (iii) yet another of the staple strands comprises a second latch domain hybridized to the second aptamer domain and selected such that the second aptamer domain is capable of binding to the binding partner such that the binding partner displaces the second latch domain; and (iv) said nucleic acid origami device is in a closed configuration when the first aptamer domain is hybridized to the first latch domain and/or the second aptamer domain is hybridized to the second latch domain; and the device transitions to an open configuration when the first aptamer domain is not hybridized to the first latch domain and the second aptamer domain is not hybridized to the second latch domain.

In other embodiments, each one of the nucleic acid origami devices composing the logic gate of the present invention is non-immunogenic, resistant to nucleases, or both non-immunogenic and resistant to nucleases.

In certain embodiments, the nucleic acid of each one of the nucleic acid origami devices composing the logic gate of the present invention is DNA.

In certain embodiments, the TLR9 recognition elements are CpG islands, and the nucleic acid origami devices may be methylated, preferably at CpG dinucleotides.

The term "methylated" refers to a nucleic acid molecule to which a methyl group has been added, specifically to the cytosine or adenine nucleotide.

In certain embodiments, the nucleic acid origami devices composing the logic gate of the present invention are each methylated at the carbon atom in position 5 of cytosine residues; at the amino group linked to the carbon atom in position 4 of cytosine residues; or at the amino group linked to the carbon atom in position 6 of adenine residues, for example, the nucleic acid origami device may be methylated at the carbon atom in position 5 of cytosine residues in CpG dinucleotides.

In certain embodiments, the nucleic acid origami devices composing the logic gate of the present invention are each modified at either cytosine or guanine residues in CpG dinucleotides. For example, the cytosine or guanine residue may be modified by covalently linking it via a linker to a macromolecule having a functional group, wherein said macromolecule is selected from a polymer such as poly(ethylene)glycol, polystyrene, poly(vinyl)chloride, pectin, polygalacturonic acid, polygalacturonic acid and poly(lactic-co-glycolic acid) (PLGA), a peptide, a lipid or a polysaccharide. The functional group may be, but is not limited to, an amino, mercapto, and carboxyl group.

In certain embodiments, the compound capable of non-covalently binding to the major- or minor-groove of a double stranded nucleic acid is selected from netropsin, distamycin, an oligoamide, a sugar-oligoamide conjugate or a bis-amidine. In a particular embodiment, the compound is netropsin, and the netropsin is further covalently linked through two of its terminal amino groups, optionally via a linker, to the double stranded nucleic acid, as shown, e.g., in FIGS. 8 and 9 of copending US provisional application titled "Non-Immunogenic and Nuclease Resistant Nucleic Acid Origami Devices And Compositions Thereof", filed on Apr. 18, 2013, of which some of the present inventors are co-inventors.

In certain embodiments, one or more further staple strands in at least one of the nucleic acid origami devices composing the logic gate of the present invention each comprises a handle domain bound to a payload, more specifically, to a payload moiety, optionally via a linker, wherein at least one of the payload(s) is one of said at least one output, and optionally, at least one of the payload(s) is one of said at least one input or emulates one of said at least one input.

In one embodiment, the linker comprises an oligonucleotide having a sequence complementary to the sequence of the handle domain and optionally comprising a further domain comprising a recognition site for enzymatic cleavage, and the payload is bound to the handle domain through the hybridization of the oligonucleotide to the handle domain. This further domain may comprise a peptide linker comprising a protease recognition site for cleavage by a protease, such as a matrix metalloproteinase. Alternatively, the linker may comprise a protein capable of binding a small molecule such as, but not limited to, a cyclooxygenase protein capable of binding paracetamol, a sodium channel subunit capable of binding tetrodotoxin and an anti-digoixin antibody capable of binding digoxin.

The term "protease recognition site" refers to an amino acid sequence recognized by an endo peptidase, such as but not limited to: Trypsin—cuts after Arg or Lys, unless followed by Pro; Chymotrypsin—cuts after Phe, Trp, or Tyr, unless followed by Pro; Elastase—cuts after Ala, Gly, Ser, or Val, unless followed by Pro; Thermolysin—cuts before Ile, Met, Phe, Trp, Tyr, or Val, unless preceded by Pro; Pepsin—cuts before Leu, Phe, Trp or Tyr, unless preceded by Pro; and Endopeptidase V8 (also known as Glu-C)—cuts after Glu.

In certain embodiments, the payload each independently is a drug, such as insulin, an antibody or a fragment thereof, a cell surface receptor ligand or a biologically active fragment thereof, a small molecule, a nucleic acid, such as an oligonucleotide, a nuclease, an aptamer, a lipid, a glycan, a protein a glycoprotein, a glycolipid, a nanoparticle, a fluorophore, a radioactive compound, a nano-antenna, or a liposome. The payload being an oligonucleotide may function as an "external oligonucleotide" for another device.

The terms "payload" and "payload moiety" are used herein interchangeably and refer both to the free payload and to said payload when covalently linked directly to the handle domain or to the linker while maintaining its biological activity.

In certain embodiments, the nano-antenna of a nucleic acid origami device included within the logic gate of the present invention, e.g., a nucleic acid origami device having the structure A, or being used as a payload when linked to the handle domain, optionally via a linker, each independently comprises a metal quantum dot, a metal nanoparticle, or a metal nanocrystal, wherein said metal is preferably Au.

In other embodiments, the plurality of staple strands are selected such that at least one of the payloads is positioned on an inner surface of a nucleic acid origami device when the device is in the closed configuration; and the transition to the open configuration causes said payload to be positioned on an outer surface of the nucleic acid origami device.

The term "inner surface" with respect to the nucleic acid origami device of the present invention in any one of the configurations defined herein, refers to any surface area of the device that is sterically precluded from interacting with members in the immediate environment surrounding the nucleic acid origami device, such as the surface of a cell, while an "outer surface" is any surface area of the device that is not sterically precluded from interacting with members in the immediate environment surrounding the nucleic acid origami device, such as the surface of a cell.

In still other embodiments, the staple strands in at least one of the nucleic acid origami devices composing the logic gate of the present invention comprises a handle domain positioned on an outer surface of the device when the device is in the closed configuration, and in this case, the handle domain is bound to a payload preferably selected from an oligonucleotide or a liposome. In certain embodiments, the handle domain positioned on the outer surface of the device when the device is in the closed configuration becomes positioned on an inner surface of the device when the device is in the open configuration.

The shape of each one of the devices composing the logic gate of the present invention may be chosen according to the purpose of the device, and is easily obtained by defining the shape in a specialized computer program well known in the art of DNA origami, such as CADnano software, available at http://www.cadnano.org.

In certain embodiments, the plurality of staple strands composing at least one of the nucleic acid origami devices are selected such that the nucleic acid origami device is substantially barrel-shaped and in other embodiments the plurality of staple strands are selected such that the nucleic acid origami device has a substantially hexagonal tube shape. The plurality of staple strands composing at least one of the nucleic acid origami devices may be selected such that the nucleic acid origami device comprises an open end and they may be selected such that the nucleic acid origami device comprises two open ends.

In certain embodiments: (i) in at least one of the nucleic acid origami devices composing the logic gate of the present invention and having the structure A or B, the plurality of staple strands are selected such that the nucleic acid origami device comprises a first domain and a second domain, wherein the first domain comprises said aptamer domain(s) of (a) each capable of binding to a binding partner; or said oligonucleotide(s) of (b), each capable of binding a DNA binding protein; or said oligonucleotide(s) of (c), each attached to a nano-antenna; and the second domain comprises said latch domain(s), wherein a first end of the first domain is attached to a first end of the second domain by at least one single-stranded nucleic acid hinge and the second end of the first domain is attached to the second end of the second domain by the hybridization or binding of each one of said aptamer domains or said oligonucleotides to said latch domains, respectively; or (ii) in at least one of the nucleic acid origami devices composing the logic gate of the present invention and having the structure C, the plurality of staple strands are selected such that the nucleic acid origami device comprises a first domain and a second domain, wherein each one of said first and second domains comprises one of said latch domains linked to an oligonucleotide capable of hybridizing with an external oligonucleotide, wherein a first end of the first domain is attached to a first end of the second domain by at least one single-stranded nucleic acid hinge and the second end of the first domain is not attached to the second end of the second domain.

In particular such embodiments: (i) the plurality of staple strands in at least one of the nucleic acid origami devices having the structure A or B are selected such that the second end of the first domain becomes unattached to the second end of the second domain if each one of said aptamer domains is contacted by its respective binding partner and/or if each one of said nano-antennas receives an electromagnetic field and undergoes inductive coupling and subsequent heating; or (ii) the plurality of staple strands in at least one of the nucleic acid origami device having the structure C are selected such that the second end of the first domain becomes attached to the second end of the second domain if each one of said latch domains is hybridized to a different one of said external oligonucleotides.

In certain embodiments, the binding partner each independently is an antigen selected from a tumor associated antigen; a cell-membrane receptor; a secreted or membrane bound growth factor; a hormone; a cytokine; a ligand; a chemokine; a bacterial, a viral or parasitic antigen; a lipid; an oligonucleotide; a sugar, an enzyme or a DNA binding protein; or it may be a "damage cue" or "damage indicator", examples of which are an obligatory intracellular molecule such as ATP, ribosome fragments, rRNA, nuclear pore components, histones, etc. for discerning cell damage in a non-discriminatory way; or microRNA, or certain isoforms or analogs of the above mentioned cues, such as glycosylation or phosphorylation variants, differentially present in a specific type of cell, a normal cell or a tumor cell.

The system of the present invention may comprise a glucose-sensing nano-device that exhibits insulin on its surface at high glucose concentration. For this purpose, as explained above, the nano-devise may comprise a binding partner that is selected such that it has a first configuration under a first condition and a different second configuration under a different second condition, and the aptamer of (a) or the oligonucleotide of (b) is capable of binding to the binding partner having the first configuration but incapable of binding to the binding partner having the second configuration such that the latch domain is displaced from the aptamer of (a) or the oligonucleotide of (b) when the binding partner transitions from the first to the second configuration, thereby opening the device and exposing the insulin. In particular, this binding partner may be an enzyme, for example a glucokinase (see Example 6).

Thus, in certain embodiments, the enzyme is a glucokinase and the aptamer domain of (a) is capable of binding to the glucokinase having the first configuration but is incapable of binding to the glucokinase having the second configuration; or the DNA binding protein is a glucose response factor and said oligonucleotide of (b) is a glucose responsive regulatory element capable of binding to the glucose response factor having the first configuration but incapable of binding to the glucose response factor having the second configuration. The glucokinase may be a mammalian glucokinase, such as but not limited to human, mouse or rat beta cell glucokinase.

In certain embodiments, the first condition (or input) is a glucose concentration in the range of 0-4.5 mM and the second condition (or input) is a glucose concentration above 4.5 mM, for example in the range of 5-10 mM.

The system of the present invention may be used to specifically kill target cells while sparing non-target cells, e.g. normal healthy cells. This is achieved by administering, by means of one or more effector nanorobots, a toxin that preferentially kills the target cells, and by stopping the action of the nanorobots when it senses, as a system also comprising one or more regulatory nanorobots, a distress or damage cue released from normal healthy cells that are also damaged in the process. The nanorobot make-up of the system depends on the logic gate required to control the effector nanorobots, for example logic gates disclosed herein or combinations thereof.

In certain embodiments, the system of the present invention comprises one effector device having one or more handle domains each bound to a payload, at least one regulator device, at least one input and one output, wherein said output has a first output state when said effector device is in the closed configuration and a second output state when said effector device is in the open configuration. In particular such embodiments, the first output state corresponds to a logical off state and the second output state corresponds to a logical on state.

In certain more particular such embodiment, the system of the present invention is a logical NAND gate, comprising two inputs and being in a logical on state if both inputs are present. In a specific embodiment, the system of the invention comprises one effector device and one regulator device, wherein (i) said effector device has the structure C and is initially in an open configuration; and (ii) said regulator device is a negative regulator device having the structure B and comprising two handle domains each bound to a nucleic acid molecule acting as a signal molecule capable of hybridizing to a different one of said latch domains of said effector device, said negative regulator device is initially in a closed configuration wherein said signal molecules are positioned on an inner surface of the negative regulator device and, when both inputs are present, transitions to an open configuration wherein said signal molecules are positioned on an outer surface of the negative regulator device, wherein the gate is in a logical on state when each one of said two signal molecules hybridizes to a different one of said latch domains of said effector device thereby promoting closure of the effector device or preventing transition of the effector device to an open configuration.

In certain more particular such embodiment, the system of the present invention is a logical NOT gate, comprising one input and being in a logical on state if the input is absent. In a specific embodiment, the system of the invention comprises one effector device and one regulator device, wherein (i) said effector device has the structure C and is initially in an open configuration; and (ii) said regulator device is a negative regulator device having the structure A and comprising two handle domains each bound to a nucleic acid molecule acting as a signal molecule capable of hybridizing to a different one of said latch domains of said effector device, said negative regulator device is initially in a closed configuration wherein said signal molecules are positioned on an inner surface of the negative regulator device and, when the input is present, transitions to an open configuration wherein said signal molecules are positioned on an outer surface of the negative regulator device, wherein the gate is in a logical on state when each one of said two signal molecules hybridizes to a different one of said latch domains of said effector device thereby promoting closure of the effector device or preventing transition of the effector device to an open configuration.

In certain more particular such embodiment, the system of the present invention is a logical OR gate, comprising two inputs and being in a logical on state if at least one of the two inputs is present. In a specific embodiment, the system of the invention comprises one effector device and two regulator devices, wherein (i) said effector device has the structure B, is initially in a closed configuration and, when both inputs are present, transitions to an open configuration; (ii) the first of said two regulator devices is a first positive regulator device having the structure A and comprises one handle domain bound to a nucleic acid molecule acting as a signal molecule capable of emulating the second of said two inputs by hybridizing to the aptamer domain of said effector device that is capable of binding to the second of said two inputs, said first positive regulator device is initially in a closed configuration wherein said signal molecule is positioned on an inner surface of said first positive regulator device and, when the first of said two inputs is present, transitions to an open configuration wherein said signal molecule is positioned on an outer surface of the positive regulator device; and (iii) the second of said two regulator devices is a second positive regulator device having the structure A and comprises one handle domain bound to a nucleic acid molecule acting as a signal molecule capable of emulating the first of said two inputs by hybridizing to the aptamer domain of said effector device that is capable of binding to the first of said two inputs, said second positive regulator device is initially in a closed configuration wherein said signal molecule is positioned on an inner surface of said second positive regulator device and, when the second of said two inputs is present, transitions to an open configuration wherein said signal molecule is positioned on an outer surface of the positive regulator device, wherein the gate is in a logical on state when the first of said two inputs binds to the aptamer domain of the effector device capable of binding to the first of said two inputs and the second of said two inputs binds to the aptamer domain of the effector device capable of binding to the second of said two inputs, such that said inputs displace the latch domains initially hybridized to said aptamer domains, respectively;

the first of said two inputs binds to the aptamer domain of said effector device capable of binding to the first of said two inputs and the signal molecule of the first positive regulator device hybridizes to the aptamer domain of said effector device capable of binding to the second of said two inputs, such that the first input and the signal molecule of the first positive regulator device displace the latch domains initially hybridized to said aptamer domains, respectively; or the second of said two inputs binds to the aptamer domain of said effector device capable of binding to the second of said two inputs and the signal molecule of the second positive regulator device hybridizes to the aptamer domain of said effector device capable of binding to the first of said two inputs, such that the second input and the signal molecule of the second positive regulator device displace the latch domains initially hybridized to said aptamer domains, respectively. The reference to an 'input that is present' is meant to represent for example the presence of an antigen that is capable of opening a nano-device by binding to an aptamer or the presence of a ligand, such as glucose at a certain concentration, that is capable of binding to a concentration-sensitive binding partner, such as a glucokinase, which upon binding of glucose alters its configuration thereby opening the nano-device.

In certain more particular such embodiment, the system of the present invention is an exclusive OR (XOR) gate, comprising two inputs and being in a logical on state if only one of the two inputs is present, i.e., if the first of said two inputs is present and the second of said two inputs is absent, or the second of said two inputs is present and the first of said two inputs is absent. In a specific embodiment, the system of the invention comprises one effector device and three regulator devices, wherein (i) said effector device has the structure B, is initially in a closed configuration and, when both inputs are present, transitions to an open configuration; (ii) the first of said three regulator devices is a first positive regulator device having the structure A and comprises one handle domain bound to a nucleic acid molecule acting as a signal molecule capable of emulating the second of said two inputs by hybridizing to the aptamer domain of said effector device that is capable of binding to the second of said two inputs, said first positive regulator device is initially in a closed configuration wherein said signal molecule is positioned on an inner surface of said first positive regulator device and, when the first of said two inputs is present, transitions to an open configuration wherein said signal molecule is positioned on an outer surface of the positive regulator device; (iii) the second of said three regulator devices is a second positive regulator device having the structure A and comprises one handle domain bound to a nucleic acid molecule acting as a signal molecule capable of emulating the first of said two inputs by hybridizing to the aptamer domain of said effector device that is capable of binding to the first of said two inputs, said second positive regulator device is initially in a closed configuration wherein said signal molecule is positioned on an inner surface of said second positive regulator device and, when the second of said two inputs is present, transitions to an open configuration wherein said signal molecule is positioned on an outer surface of the positive regulator device; and (iv) the third of said three regulator devices is a negative regulator device having the structure B and comprising two handle domains each bound to a nucleic acid molecule acting as a signal molecule capable of hybridizing to a different one of said latch domains of said effector device, said negative regulator device is initially in a closed configuration wherein said signal molecules are positioned on an inner surface of the negative regulator device and, when both inputs are present, transitions to an open configuration wherein said signal molecules are positioned on an outer surface of the negative regulator device, wherein the gate is in a logical on state when: the first of said two inputs binds to the aptamer domain of said effector device capable of binding to the first of said two inputs and the signal molecule of the first positive regulator device hybridizes to the aptamer domain of said effector device capable of binding to the second of said two inputs, such that the first input and the signal molecule of the first positive regulator device displace the latch domains initially hybridized to said aptamer domains, respectively; or the second of said two inputs binds to the aptamer domain of said effector device capable of binding to the second of said two inputs and the signal molecule of the second positive regulator device hybridizes to the aptamer domain of said effector device capable of binding to the first of said two inputs, such that the second input and the signal molecule of the second positive regulator device displace the latch domains initially hybridized to said aptamer domains, respectively, and wherein both inputs are present, the first of said two inputs binds to the aptamer domain of the effector device capable of binding to the first of said two inputs and the second of said two inputs binds to the aptamer domain of the effector device capable of binding to the second of said two inputs, such that said inputs displace the latch domains initially hybridized to said aptamer domains, respectively, and each one of said two signal molecules of the negative regulator device hybridizes to a different one of said latch domains of said effector device thereby promoting closure of the effector device or preventing transition of the effector device to an open configuration.

In other embodiments, the system of the present invention comprises two effector devices each having one or more handle domains each bound to a payload, at least one regulator device, at least one input and two outputs, wherein the first of said two outputs has a first output state when the first of said two effector devices is in the closed configuration and a second output state when the first of said two effector devices is in the open configuration; and the second of said two outputs has a first output state when the second of said two effector devices is in the closed configuration and a second output state when the second of said two effector devices is in the open configuration. In particular such embodiments, each one of the first output states corresponds to a logical off state and each one of the second output states corresponds to a logical on state.

In certain more particular such embodiment, the system of the present invention is a logical controlled NOT gate, comprising two inputs and two outputs, wherein the first output is in a logical on state if only one of the two inputs is present and the second output is sensitive to the presence of the first of said two inputs only and it is thus in a logical on state if either only the first of said two inputs or both inputs are present.

In a specific embodiment, the system of the invention comprises two effector devices and four regulator devices, wherein (i) the first of said two effector devices has the structure B, is initially in a closed configuration and, when both inputs are present, transitions to an open configuration; (ii) the first of said three regulator devices is a first positive regulator device having the structure A and comprises one handle domain bound to a nucleic acid molecule acting as a signal molecule capable of emulating the second of said two inputs by hybridizing to the aptamer domain of said effector device that is capable of binding to the second of said two inputs, said first positive regulator device is initially in a closed configuration wherein said signal molecule is positioned on an inner surface of said first positive regulator device and, when the first of said two inputs is present, transitions to an open configuration wherein said signal molecule is positioned on an outer surface of the positive regulator device; (iii) the second of said three regulator devices is a second positive regulator device having the structure A and comprises one handle domain bound to a nucleic acid molecule acting as a signal molecule capable of emulating the first of said two inputs by hybridizing to the aptamer domain of said effector device that is capable of binding to the first of said two inputs, said second positive regulator device is initially in a closed configuration wherein said signal molecule is positioned on an inner surface of said second positive regulator device and, when the second of said two inputs is present, transitions to an open configuration wherein said signal molecule is positioned on an outer surface of the positive regulator device; (iv) the third of said three regulator devices is a negative regulator device having the structure B and comprising two handle domains each bound to a nucleic acid molecule acting as a signal molecule capable of hybridizing to a different one of said latch domains of said effector device, said negative regulator device is initially in a closed configuration wherein said signal molecules are positioned on an inner surface of the negative regulator device and, when both inputs are present, transitions to an open configuration wherein said signal molecules are positioned on an outer surface of the negative regulator device; and (v) the second of said two effector devices has the structure A, is initially in a closed configuration and, when the first of said two inputs is present, transitions to an open configuration, wherein the first of said two outputs of the gate is in a logical on state when: the first of said two inputs binds to the aptamer domain of said first of said two effector devices capable of binding to the first of said two inputs and the signal molecule of the first positive regulator device hybridizes to the aptamer domain of said first of said two effector devices capable of binding to the second of said two inputs, such that the first input and the signal molecule of the first positive regulator device displace the latch domains initially hybridized to said aptamer domains, respectively; or the second of said two inputs binds to the aptamer domain of said first of said two effector devices capable of binding to the second of said two inputs and the signal molecule of the second positive regulator device hybridizes to the aptamer domain of said first of said two effector devices capable of binding to the first of said two inputs, such that the second input and the signal molecule of the second positive regulator device displace the latch domains initially hybridized to said aptamer domains, respectively, and wherein both inputs are present, the first of said two inputs binds to the aptamer domain of the first of said two effector devices capable of binding to the first of said two inputs and the second of said two inputs binds to the aptamer domain of the first of said two effector devices capable of binding to the second of said two inputs, such that said inputs displace the latch domains initially hybridized to said aptamer domains, respectively, and each one of said two signal molecules of the negative regulator device hybridizes to a different one of said latch domains of said first of said two effector devices thereby promoting closure of the effector device or preventing transition of the first of said two effector devices to an open configuration; and wherein the second of said two outputs of the gate is in a logical on state if only the first of said two inputs is present, when the first of said two inputs binds to each one of the aptamer domains of the second of said two effector devices capable of binding to the first of said two inputs such that each signal molecule displaces a different one of said latch domains.

In certain embodiments of the various logic gates of the present invention, i.e., NAND, NOT, OR, XOR, and controlled NOT gates, when said effector device(s) is in an open configuration, each one of the payload is positioned on an outer surface of the effector device(s).

In this work we focused on artificial quorum sensing (QS) [Bassler, B. L. et al., 2006] as a bio-inspired collective behavior. QS is a phenomenon where microorganisms communicate and coordinate their behavior by the accumulation of signaling molecules. QS enables bacteria to regulate phenotypes such as biofilm formation [Davies, D. G. et al., 1998], bioluminescence [Engebrecht, J. et al., 1984], sporulation [Grossman, A. D. et al., 1995] and virulence factor secretion [Miller, M. B. et al., 2002; Hentzer, M. et al., 2003], by population density. Although group behaviors were not initially thought to exist in bacteria, they are now known to occur in many species and likely appeared early in evolution [Lerat, E. et al., 2004]. Population density-dependent group behaviors are also common in animals [Bowler, D. E. et al., 2005; Hauzy, C. et al., 2007; Kim, S. Y. et al., 2009; Karels, T. J. et al., 2000], and are mediated by neural-hormonal-behavioral circuits [Nephew, B. C. et al., 2003].

Collective behavior is a powerful paradigm in computing and robotics, and QS was demonstrated as a strategy to achieve this goal. Interestingly, QS has been proposed as a mechanism to coordinate behaviors of nanorobot swarms. Particularly, nanorobots exhibiting collective behaviors could have an enormous impact on medicine. However, this technology has not been implemented in reality as yet. Here we demonstrate a preliminary design towards this goal, which is based on the DNA nanorobot described above.

QS is based on a signal generated by each individual nanorobot, which builds up in the environment proportionally to the nanorobot population density. Subsequently, each nanorobot has to be able to detect this signal and respond to it by a concentration-dependent mechanism. The DNA nanorobot is activated in response to protein molecules termed "keys" through an aptamer-based gate [Douglas, S. M. et al., 2012] in a concentration-dependent manner, making these proteins good candidates for use as QS signals.

It has been found in accordance with the present invention that nucleic acid origami devices carrying quorum sensing molecules may aggregate in a concentration dependent manner both in vivo and in vitro as shown in Example 2. In this Example it is also shown that nanorobots can be made to aggregate by contacting one or more oligonucleotides presented on the outer surface of each individual nanorobot that is complementary to one or more other oligonucleotide also presented on the outer surface of each individual nanorobot. Furthermore, Example 3 below shows that the delivery of a drug may be controlled so that the drug is presented to the cells only when the nucleic acid origami devices carrying the drug have accumulated to a high concentration. In this way, the target cells do not experience low levels of the drug that may enable them to develop resistance, as is often the case when the drug is given systemically, but are challenged with a high level of the drug that is likely to kill all cells in a short time span.

Thus, in another aspect, the present invention relates to a system exhibiting quorum sensing comprising a plurality of effector nucleic acid origami devices each having the structure A, B or C as defined above in connection with the system acting as a logic gate or, alternatively, a plurality of a member each selected from a liposome, a particle or an artificial cell; at least one input; and at least one output, wherein said plurality of effector nucleic acid origami devices or members aggregates at a predetermined concentration, and wherein: (i) each one of the effector nucleic acid origami devices comprises said handle domain bound to a first oligonucleotide capable of hybridizing with said aptamer domain of another of said effector nucleic acid origami devices and positioned on the outer surface of the device when the device is in the closed configuration; or (ii) each one of the members comprises on an outer surface thereof (a) a staple strand comprising a handle domain bound to a first oligonucleotide; and (b) a further staple strand comprising a second oligonucleotide selected such that it is capable of hybridizing to a first oligonucleotide of another of said plurality of members, each one of said effector nucleic acid origami devices or members having on open and a closed configuration and is initially in the closed configuration.

In certain embodiments, upon aggregation of said plurality of effector nucleic acid origami devices, said first oligonucleotide of each one of said effector nucleic acid origami devices binds to said aptamer domain of another of said effector nucleic acid origami devices such that the first oligonucleotide, acting as the first of said at least one input, displaces the latch domain of said another of said effector nucleic acid origami devices, thereby promoting transition of said another of said effector nucleic acid origami devices to an open configuration.

In certain embodiments, each one of said effector nucleic acid origami devices or each one of said members comprises yet a further staple strand comprising an aptamer capable of binding to a binding partner acting as another of said at least one input, in particular wherein said binding partner is a target antigen. In this way, the effector nucleic acid origami devices are likely to aggregate and be activated at the desired target.

In other embodiments, each one of said effector nucleic acid origami devices or, in particular, each one of said members, further comprises a handle domain bound to a quorum sensing molecule, optionally via a linker, said quorum sensing molecule acting as a further one of said at least one input.

In particular embodiments, said linker comprises a third oligonucleotide having a sequence complementary to the sequence of the handle domain and optionally a further domain comprising a recognition site for enzymatic cleavage, and the quorum sensing molecule is bound to the handle domain through the hybridization of the third oligonucleotide to the handle domain. This further domain may comprise a peptide linker comprising a protease recognition site for cleavage by a protease, such as a matrix metalloproteinase.

In some embodiments, each one of said effector nucleic acid origami devices or members comprises still a further staple strand positioned on its outer surface, said further staple strand comprising a fourth oligonucleotide selected such that it is capable of hybridizing to said handle domain of another of said effector nucleic acid origami devices or members, such that the fourth oligonucleotide displaces the third oligonucleotide of said another of said effector nucleic acid origami devices or members, linked to the quorum sensing molecule, thereby releasing said quorum sensing molecule linked to said third oligonucleotide. In this way, the concentration of the released quorum sensing molecule represents the concentration of the effector nucleic acid origami devices or members present.

In certain embodiments, the released quorum sensing molecule is capable of causing transition of one of said effector nucleic acid origami devices or members from its closed configuration to its open configuration. In particular, the quorum sensing molecule is selected from a channel activating agent and a membrane permeable compound such as a peptide.

A non-liming example of how a peptide may function as a quorum sensing molecule is liposomes that can be triggered by an external signal such as a small peptide, that is capable of diffusing into the liposome and trigger a biosynthetic machinery. Moreover, we have demonstrated DNA arms decorated with a positively-charged peptide (we used GRKKRRQRRRPQ; SEQ ID NO: 2) on the end, which can by themselves penetrate into the liposome and trigger its machinery. The process is as follows: 1) DNA arms on separate liposomes interact based on liposome density; 2) arm interaction displaces a DNA strand containing a positive peptide as in above; 3) the displaced arm with peptide penetrates into the liposome and activates its internal machinery. Since this process initiates with strand displacement (step 2), which occurs only upon a certain density of liposomes (step 1), it represents quorum sensing.

In certain embodiments the quorum sensing peptide is capable of penetrating membranes and in particular embodiments has the sequence KPLGMWSRC SEQ ID NO: 3) or GRKKRRQRRRPQ.

The concentration at which the effector nucleic acid origami devices or members of the quorum sensing system aggregate can be calibrated by adjusting the affinities between the interacting oligonucleotides or quorum sensing molecules attached to the devices and members.

In certain embodiments, said further nucleic acid molecule is capable of hybridizing to said handle domain of another of said plurality of at least one effector device or to said handle domain of another of said plurality of said member if the binding affinity of said handle domain to said further nucleic acid molecule is higher than the binding affinity of said handle domain to said nucleic acid molecule linked to the quorum sensing molecule.

In particular embodiments, the association constant of said binding affinity of said handle domain to said further nucleic acid molecule is selected by adjusting the degree of complementarity of said further nucleic acid molecule with said handle domain; and the association constant of said binding affinity of said handle domain to said nucleic acid molecule linked to the quorum sensing molecule is selected by adjusting the degree of complementarity of said nucleic acid molecule linked to the quorum sensing molecule with said handle domain.

In further embodiments, each one of said association constants of said binding affinity of said handle domain to said further nucleic acid molecule and to said nucleic acid molecule linked to the quorum sensing molecule is selected such that the binding affinity of said handle domain to said further nucleic acid molecule is higher than the binding affinity of said handle domain to said nucleic acid molecule linked to the quorum sensing molecule at a predetermined concentration of said further nucleic acid molecule.

In a further aspect, the present invention provides a pharmaceutical composition comprising a system acting as a logic gate or a system exhibiting quorum sensing in any one of the configurations defined above, and a pharmaceutically acceptable carrier.

Pharmaceutical compositions for use in accordance with the present invention may be formulated in conventional manner using one or more physiologically acceptable carriers or excipients. The carrier(s) must be "acceptable" in the sense of being compatible with the other ingredients of the composition and not deleterious to the recipient thereof.

The following exemplification of carriers, modes of administration, dosage forms, etc., are listed as known possibilities from which the carriers, modes of administration, dosage forms, etc., may be selected for use with the present invention. Those of ordinary skill in the art will understand, however, that any given formulation and mode of administration selected should first be tested to determine that it achieves the desired results.

Methods of administration include, but are not limited to, parenteral, e.g., intravenous, intraperitoneal, intramuscular, subcutaneous, mucosal (e.g., oral, intranasal, buccal, vaginal, rectal, intraocular), intrathecal, topical and intradermal routes. Administration can be systemic or local. In certain embodiments, the pharmaceutical composition is adapted for intra-brain administration.

The term "carrier" refers to a diluent, adjuvant, excipient, or vehicle with which the active agent is administered. The carriers in the pharmaceutical composition may comprise a binder, such as microcrystalline cellulose, polyvinylpyrrolidone (polyvidone or povidone), gum tragacanth, gelatin, starch, lactose or lactose monohydrate; a disintegrating agent, such as alginic acid, maize starch and the like; a lubricant or surfactant, such as magnesium stearate, or sodium lauryl sulphate; and a glidant, such as colloidal silicon dioxide.

The compositions may be formulated for parenteral administration by injection, e.g., by bolus injection or continuous infusion. Formulations for injection may be presented in unit dosage form, e.g., in ampoules or in multidose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen free water, before use.

For administration by inhalation, for example for nasal administration, the compositions for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of, e.g., gelatin, for use in an inhaler or insufflator may be formulated containing a powder mix of the compound and a suitable powder base such as lactose or starch.

In certain embodiments the pharmaceutical composition is formulated for administration by any known method as described above.

The invention will now be illustrated by the following non-limiting examples.

EXAMPLES

Material and Methods
DNA Scaffold.

A 7249 bp circular single-strand DNA molecule was used in the following examples (M13mp18 DNA; New England Biolabs; NEB #N4040; SEQ ID NO: 4.

Staples.

Purchased from Integrated DNA Technologies SEQ ID NOs: 5-282. All sequences are in the 5' to 3' direction. The oligonucleotides were reconstituted in ultrapure, DNase/RNase-free water to 100 μM concentration and stored at −20° C.

Robot Preparation.

Robots were initially produced by mixing M13mp18 ssDNA as scaffold strand (final concentration of 20 nM) and staple strands (final concentrations of 200 nM of each strand). Buffer and salts of solution included 5 mM Tris, 1 mM EDTA (pH 8.0 at 20° C.) and 10 mM $MgCl_2$. The mixture was subjected to a thermal-annealing ramp for folding. Initially the following program was used: 80° C. to 60° C. at 2 min/° C., 60° C. to 20° C. at 150 min/° C.

Purification of Folded Robots:

After folding, excess staples were removed by centrifugal filtration using Amicon Ultra-0.5 mL 100K centrifugal filters (Millipore). Folding buffer was added to reach a total volume of 500 μL, after which samples were centrifuged at 12,000 g for 10 min. this was repeated three times. DNA concentration was measured by spectrophotometer (Thermo Sci. NanoDrop 2000c).

Gel Purification of Folded Samples.

Figure 1A:
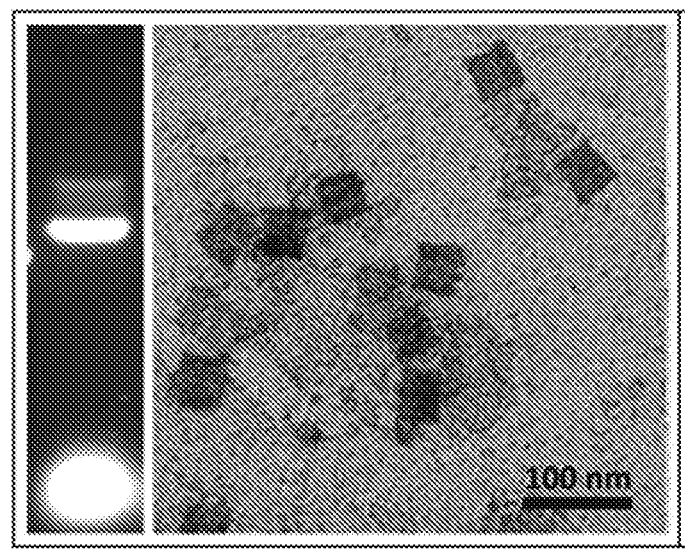
FIGS. 1A-B visualizes nanorobots by agarose-gel (left panels) and transmission electron microscopy (TEM) micrographs (right panels) of nanorobots obtained at different folding durations. Both samples of A and B were folded at 20 nM scaffold concentration, 200 nM staples concentration, 1×Tris/Acetic acid/EDTA (TAE) buffer, 10 mM $MgCl_2$. After folding, excess staples were removed using micron Ultra-0.5 mL 100K centrifugal filters (Millipore). (A) Folding duration is 80-60° C. at 2 min/° C. and 60-10° C. at 150 min/° C. (B) Folding duration is 80-60° C. at 5 min/° C., 60-10° C. at 75 min/° C.
Figure 1B:
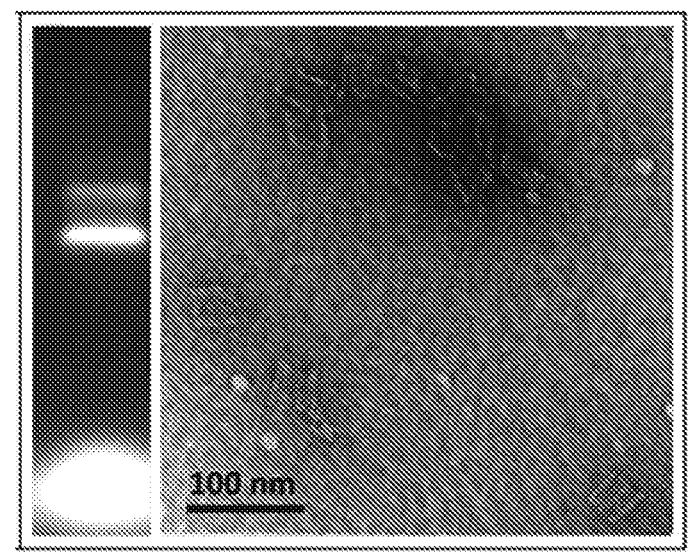

Leading monomer bands were visualized on a UV table and excised from a 1.5%-2% agarose gel (running buffer is 0.5×TBE supplemented with 10 mM $MgCl_2$), frozen at −20° C. for 5 min, chopped to small pieces and centrifuged at 13,000 g for 3 min inside a Quantum Prep Freeze N' Squeeze DNA Gel Extraction spin column (Bio-Rad). Recovered solution was measured for DNA concentration by spectrophotometer (Thermo Sci. NanoDrop 2000c) and prepared for imaging by transmission electron microscopy (TEM) (FIGS. 1A-B).

TEM Negative-Stain.

Figure 2:
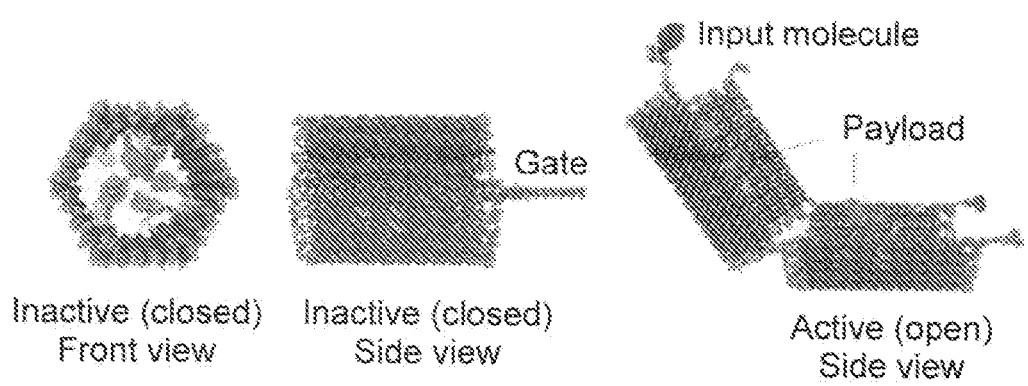
FIG. 2 depicts a 3D representation of a nanorobot in its inactive state (left panel in front view and middle panel in side view) and in its active open state (right panel).

Briefly, 5 μL of 0.5 M NaOH were added to a pre-made frozen aliquot of 100 μL 2% uranyl formate solution (Polysciences, 24762) followed by rigorous vortexing for 3 minutes, after which solution was centrifuged at 18,000 g for 5 minutes and precipitate was removed. Robot samples at 1-5 nM concentration were loaded onto a TEM Grid (Science Services, EFCF400-Cu-50) immediately after glow-discharge treatment (Emitech K100X), followed by two consecutive washes with 0.1% uranyl formate solution. During the third wash the grid was incubated with uranyl formate solution for 30 seconds. Samples were visualized using a TEM microscope (JEM-1400, JEOL) an hour to one week after negative staining. The robots were folded during 80-60° C. at 2 min/° C. and 60-10° C. at 150 min/° C. or during 80-60° C. at 5 min/° C., 60-10° C. at 75 min/° C. (Not shown). A graphic depiction of the nanorobots used in the examples is shown in FIG. 2.

Payload Preparation.

Antibodies were digested using a commercial kit (Thermo) with immobilized ficin in mouse IgG digestion buffer with 25 mM cysteine by shaking at a 37° C. water bath for 4 hours. Antibody Fab' fragments were purified by centrifugal filtration (Amicon, 10K MWCO Millipore) and evaluated by spectrophotometer (Thermo Sci. NanoDrop 2000c). Fab' fragments were buffer-exchanged into 0.05 M sodium borate buffer, pH 8.5, and incubated with DyLight Amine-Reactive Dye (Thermo) for 1 hour at room temperature on a rotary shaker. Excess dye was thoroughly removed using Amicon 10K MWCO (Millipore). Fab' fragments were incubated for 1 minute with 5'-amine-modified linker oligonucleotide (5AmMC6/GAACTGGAGTAGCAC (SEQ ID NO: 283, Integrated DNA Technologies) at a molar ratio of 1 to 10, in a 0.1 M MES-buffered saline, pH 4.7 (Pierce #28390). EDC (Thermo, #22980) was added at a molar ratio of 5000 to 1 Fab' fragment and incubated at room temperature for 1 hour on a rotary shaker. Afterwards, Tris was added to a final concentration of 10 mM and solution was filtered via Amicon column 30K MWCO (Millipore).

Loading of Robot.

Oligonucleotide-Fab' concentration was evaluated via absorption at 260 and 280 nm. Loading was performed for 2 hours on a rotary shaker at room temperature in folding buffer (10 mM $MgCl_2$ in 1×TAE) at a 2-fold molar excess of payloads to loading sites. Finally, loaded robots were cleaned by centrifugal filtration with a 100K MWCO Amicon column (Millipore) as described above Example 1. Robot Interaction Design Cue-driven collisions between robots were based on toehold-mediated strand displacement reactions. The basic design enabling collisions between DNA strands extending from E, P, and N robots was based on a 3-level interaction: the first level is the interaction of the cue itself (e.g. PDGF or VEGF in this study) with the sensing strands of the gates of all robots (E, P, and N). Alternatively, the E gates can also interact with either P or N as described in FIGS. 3A-C.

Interaction Between E and P.

Figure 3A:
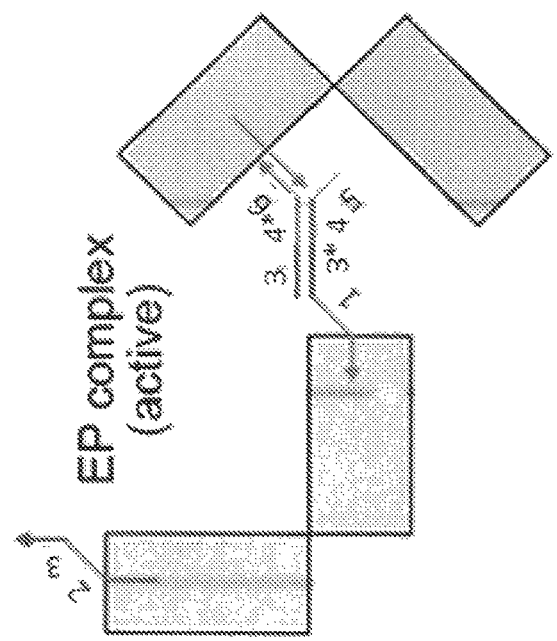
FIGS. 3A-C depict the basic design enabling collisions between DNA strands extending from E (effector), P (positive regulator), and N (negative regulator) robots. (A) Interaction between E and P robots; (B) Interaction between E and N robots; (C) Structural basis for differential keying of E and F (a second effector) robots.
Figure 3A:
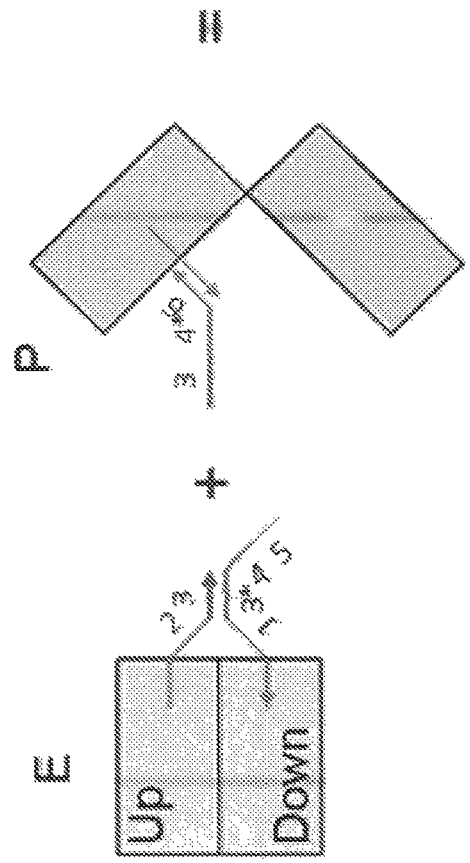

Robots are depicted in FIG. 3A from a side view schematically as rectangles revolving around a vertical axis. The E gate complementary strand contains four regions (from 5' to 3'): 5 (toehold for collision with N), 4 (toehold for collision with P), 3* (partially complements with the aptamer), and 1 (anchors the gate to the robot chassis). The sensing strand contains two regions (from 5' to 3'): 2 (anchors the gate to the robot chassis) and 3 (the aptamer). The key loaded into P contains 3 regions (from 5' to 3'): 3 (portion of the sensing strand which only appear identical in this scheme), 4* (hybridizes with toehold 4), and 6 (loading sequence to robot).

Interaction Between E and N.

Figure 3B:
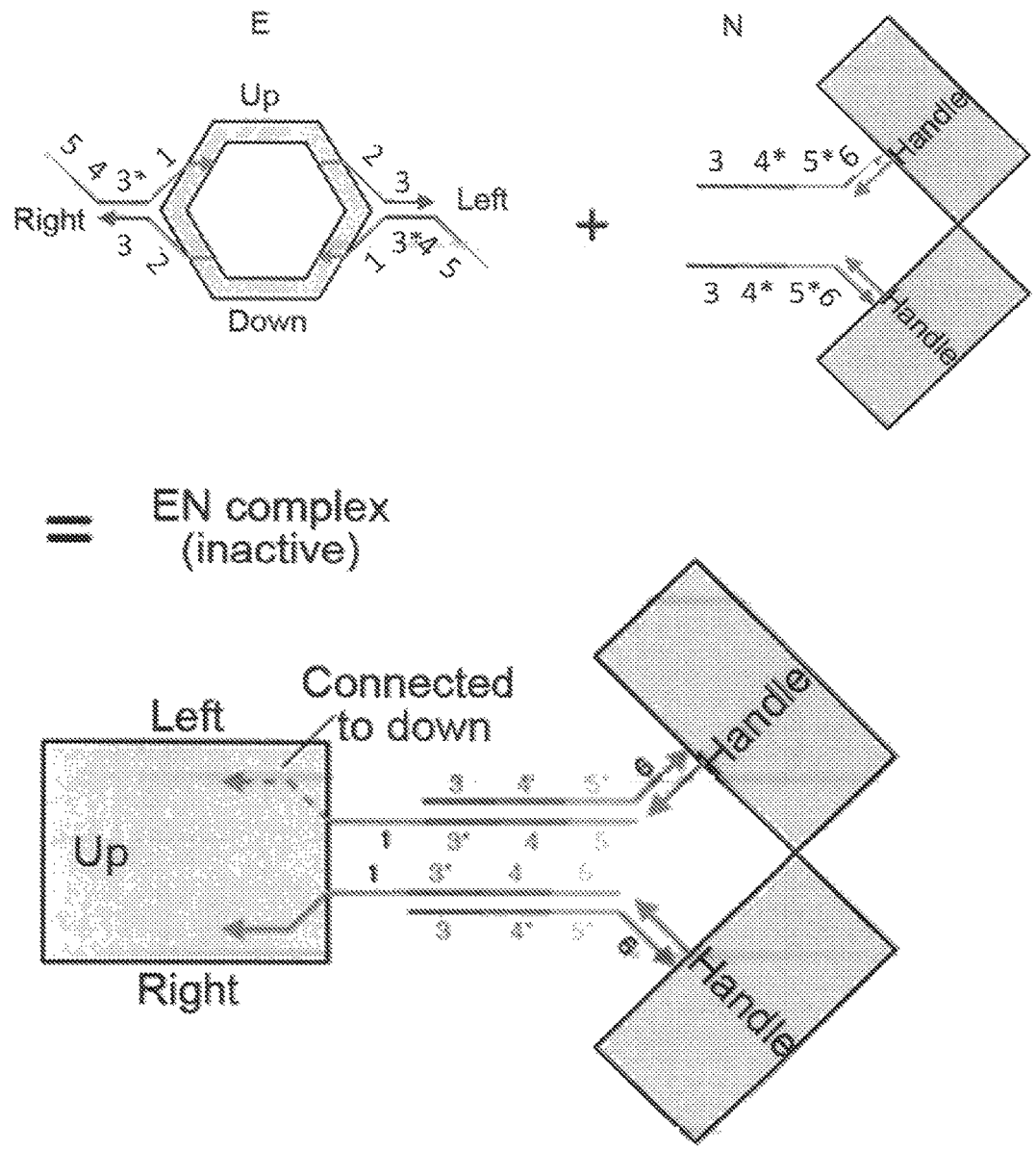

E robots are shown in FIG. 3B first from a front view with the virtual sides stated for proper orientation. The arms (clasps) extending from N include 4 regions (from 5' to 3'): 3 (portion of the sensing strand which only appear identical in this scheme), 4* (hybridizes with toehold 4), 5* (hybridizes with toehold 5), and 6. Multiple arms extending from N clasp the two gates of E. Since these are located on opposite sides of the robot (up and down), the result is inability of E to open properly.

Structural Basis for Differential Keying of E and F Robots.

Figure 3C:
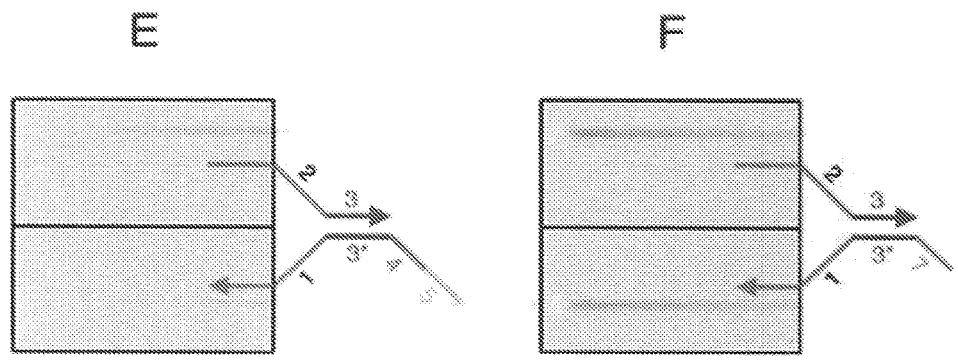

E and F consist of different regions dictating collisions with P and N. P1 and P2 robots key E by interacting with region 4 on the E gate (FIG. 3C). N robots close E by interacting with region 5. Since F robots contain neither region 4 nor 5, robots P1, P2 and N cannot interact with it. However, P3 keys F by interacting with region 7, which is also why it cannot key E.

It is important to note that the N gate complementary strands lack regions 5 and 4, so the N clasp arms cannot hybridize with them and inactivate N itself.

Based on this basic design, collision-mediating sequences were chosen and the resulting systems EP, EN and EPN were modeled and prototyped in visual DSD (vDSD; Lakin et al. (2011) Microsoft Research 27: 3211-3213). The sequences were then altered as necessary to achieve the desired performance and kinetics.

Simulated Kinetics of the EP Complex.

E and P robots in varying stoichiometries—from 0.1 to 10—were simulated in vDSD (not shown), and it was found that the fastest reaction occurs when P is at a molar excess of 5 over E, consistent with the ex-vivo prototyping.

Example 2. A Nanorobotic Collision-Based Computer Controlling Therapeutic Molecules in a Living Animal A scheme showing the nanorobot used in these studies is shown in FIG. 2 and FIG. 4A. The insect *Blaberus discoidalis* was chosen as model animal for various reasons, including simplicity, previous experience with closely related models, and availability of reliable custom made reagents [Bulmer, M. S. et al., 2009]. Importantly, the hemolymph of *B. discoidalis* expresses negligible nuclease activity and contains large amounts of free DNA as reported for other Dictyoptera [Garbutt, J. S. et al., 2012], and its salt/metal composition well supports DNA origami structures. Thus, the DNA origami nanorobots can survive for relatively long periods in the insect hemolymph. Resident DNA fragments are used here as endogenous biological cues. Stability in hemolymph was confirmed by quantitative PCR (not shown), and DNA cues were defined by sequencing (not shown).

Figure 5A:
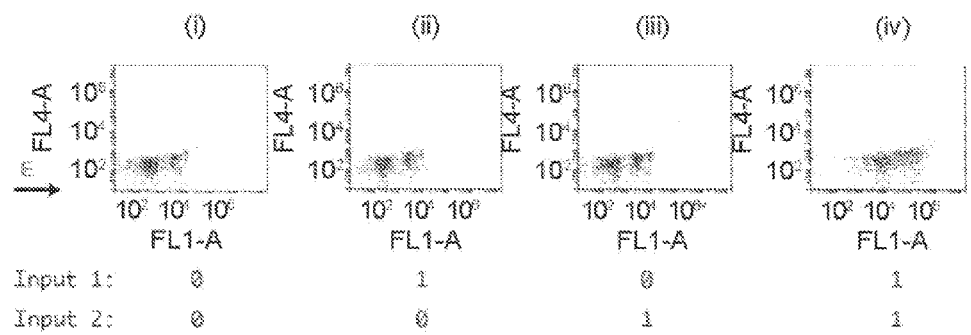
FIGS. 5A-F depict Fluorescence Assisted Cell Sorting (FACS) analysis of fluorescently labeled nanorobots tested in vitro, in which each panel shows the response of the nanorobots to the presence or absence of either one of the two cues: (i) no cue, (ii) cue 1 present, cue 2 absent, (iii) cue 1 absent, cue 2 present, (iv) both cues present. (A) E architecture providing an AND gate; (B) EP1 architecture providing an OR gate; (C) EP1P2N architecture providing a XOR gate; and (D, E) EopenN architectures providing a NAND gate (D) and a NOT gate (E).

The system was first examined on isolated insect hemocytes ex-vivo, with fluorescent anti-insect antibodies loaded as the effector payload, and synthetic DNA fragments taken from the sequencing data as cues. A typical nanorobot mixture contained 0.1 pmol of the effector nanorobot, and 0.1 pmol or more of each regulator nanorobot, as described below. E architecture exhibited AND gate behavior as previously observed with protein cues (FIG. 4B and FIG. 5A). For clarity, the truth table for the AND gate is shown below (k represents "key"):

| Truth table for AND gate | | |
|---|---|---|
| k1 | k2 | E |
| 0 | 0 | 0 |
| 1 | 0 | 0 |
| 0 | 1 | 0 |
| 1 | 1 | 1 |

Figure 5B:
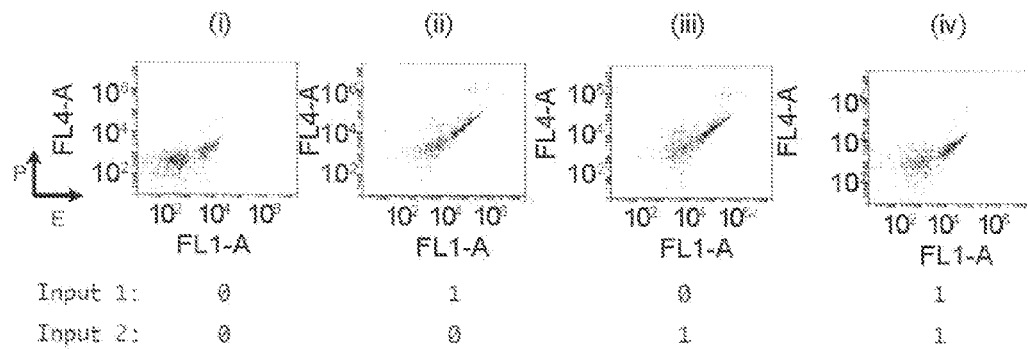

EP1P2 architecture exhibited partial to good activity at a 1:1:1 stoichiometry, and good activity at 1:>2:>2, which correlated well with an OR gate behavior. Binding of the target cells by an EP1 or EP2 nanorobot complex instead of just by solitary E nanorobots was shown by loading P1 and P2 with a reporter payload emitting at a wavelength different from that of the effector payload (FIG. 4C and FIG. 5B). For clarity, the truth table for the OR gate is shown below:

| Truth table for OR gate | | | | |
|---|---|---|---|---|
| k1 | k2 | P1 | P2 | E |
| 0 | 0 | 0 | 0 | 0 |
| 1 | 0 | 1 | 0 | 1 |
| 0 | 1 | 0 | 1 | 1 |
| 1 | 1 | 1 | 1 | 1 |

The third architecture, EP1P2N, performed similar to EP1P2 (OR) at first. XOR behavior emerged only when N was at a molar excess of ~10 over E (not shown).

| Truth table for XOR gate | | | | | |
|---|---|---|---|---|---|
| k1 | k2 | P1 | P2 | N | E |
| 0 | 0 | 0 | 0 | 0 | 0 |
| 1 | 0 | 1 | 0 | 0 | 1 |
| 0 | 1 | 0 | 1 | 0 | 1 |
| 1 | 1 | 1 | 1 | 1 | 0 |

Figure 4D:
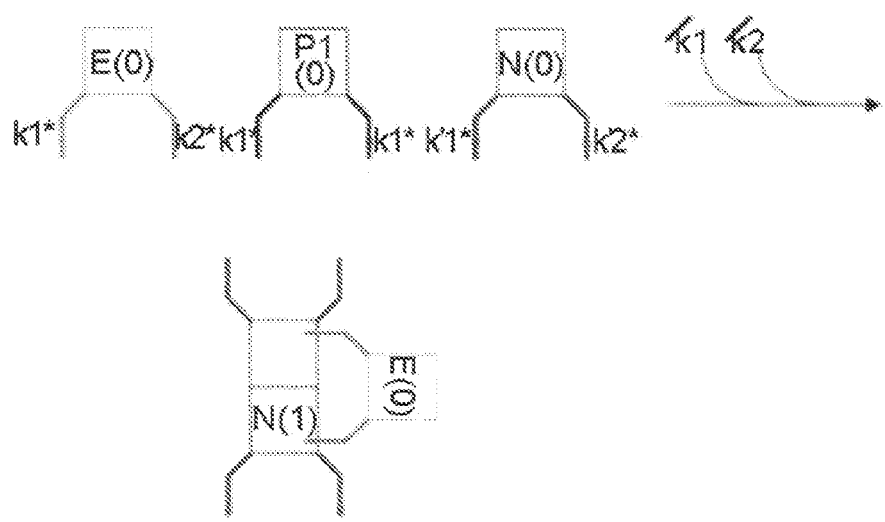
Figure 5C:
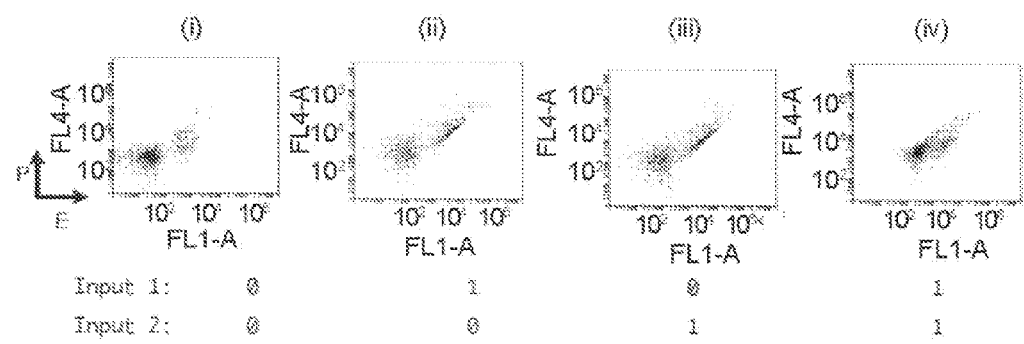

EP1P2N architecture integrates XOR (E output) with AND (N output), thus emulating a 1-bit adder in which the sum bit is relayed to the effector payload by E in the EP1 and EP2 complexes. Hence, it can be programmed to respond to a cue count rather than to the identity of particular cues. The carry bit cannot be relayed by N as both nanorobots in the EN complex (unlike in the EP complexes) directly face each other and sterically prevent each other from binding target cells; however it can be relayed by adding a second effector nanorobot (F), which is not keyed by P1 and P2 and not negated by N. Thus, X or Y alone activate E, while XY activate only F (E is negated by N) (FIG. 4D and FIG. 5C). For clarity, the truth table for the XOR gate is shown above.

Figure 4E:
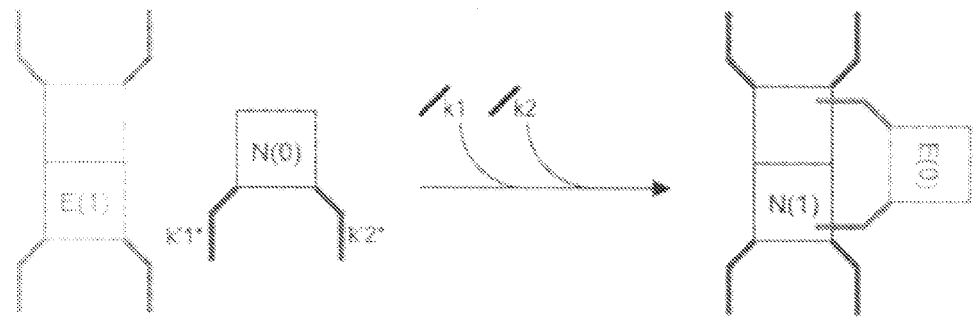
Figure 5D:
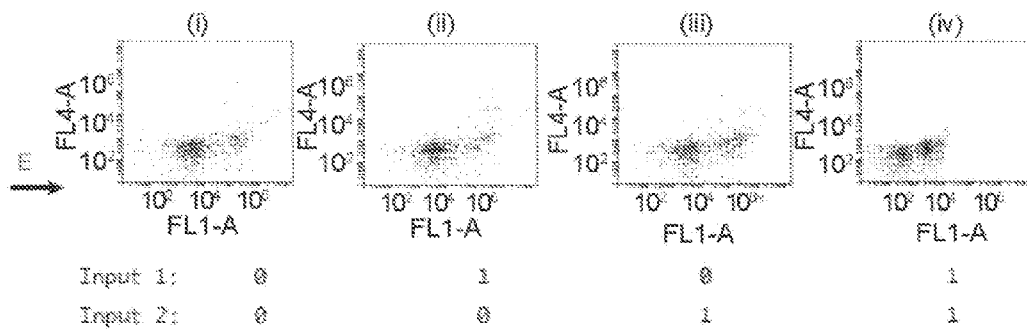

Of particular importance is the emulation of functionally complete gates, such as NAND and NOR, which can be cascaded to build any other gate. NAND architecture can be based on two nanorobot types: Eopen, which is similar to E but lacks gate strands, hence it is constitutively open regardless of the inputs X and Y; and N, which opens in response to XY and negates Eopen as a result. This architecture therefore produces 0 in response to XY, and 1 otherwise (FIG. 4E), and performed well at a 1:5 stoichiometry of EopenN (FIG. 5D). For clarity, the truth table for the NAND gate is shown below:

Truth table for NAND gate

| k1 | k2 | N | E |
|----|----|----|----|
| 0 | 0 | 0 | 1 |
| 1 | 0 | 0 | 1 |
| 0 | 1 | 0 | 1 |
| 1 | 1 | 1 | 0 |

Figure 4F:
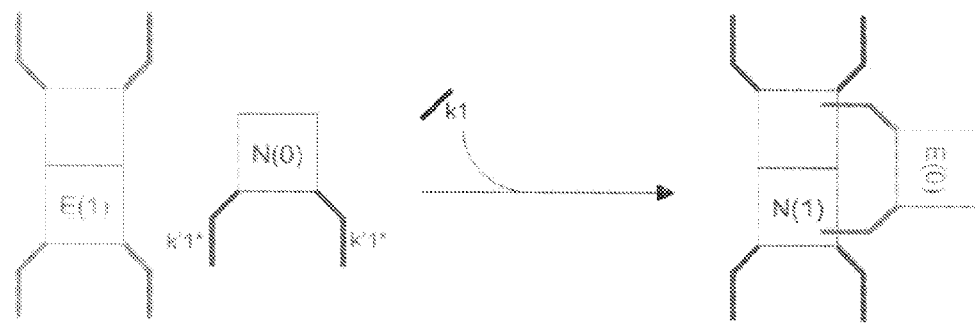
Figure 5E:
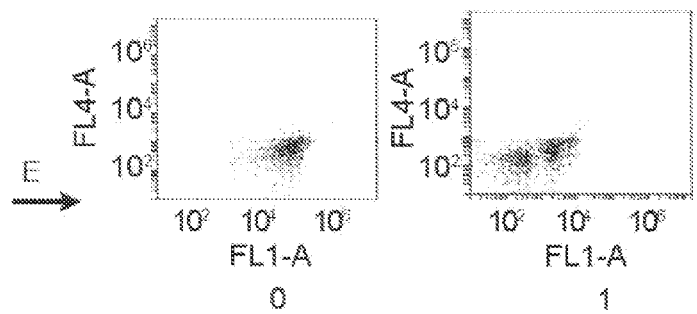

A simple inverter was constructed from this NAND gate (resulting in a NOT gate), by programming N to respond to X only (by placing two identical X arms instead of X and Y arms on the nanorobot), termed NX. EopenNX architecture produces 1 if X is absent (by Eopen) and 0 if X is present (by NX negating Eopen) (FIG. 4F), and performed well on insect cells at a 1:5 stoichiometry (FIG. 5E). The truth table for the NX gate is shown below:

Truth table for NX gate

| k1 | N | E |
|----|---|---|
| 0 | 0 | 1 |
| 1 | 1 | 0 |

Figure 5F:
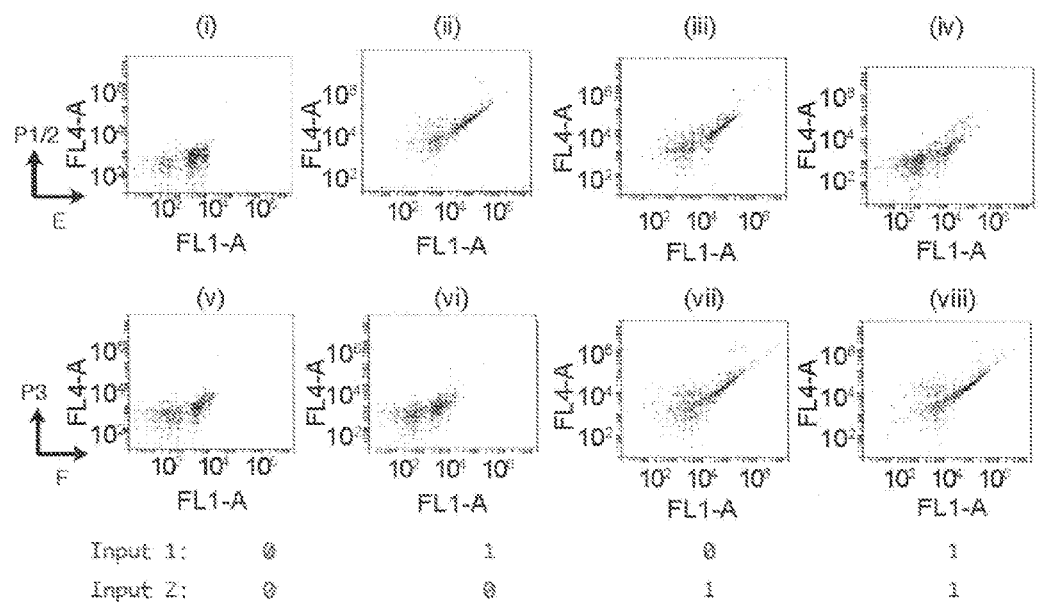
Figure 6A:
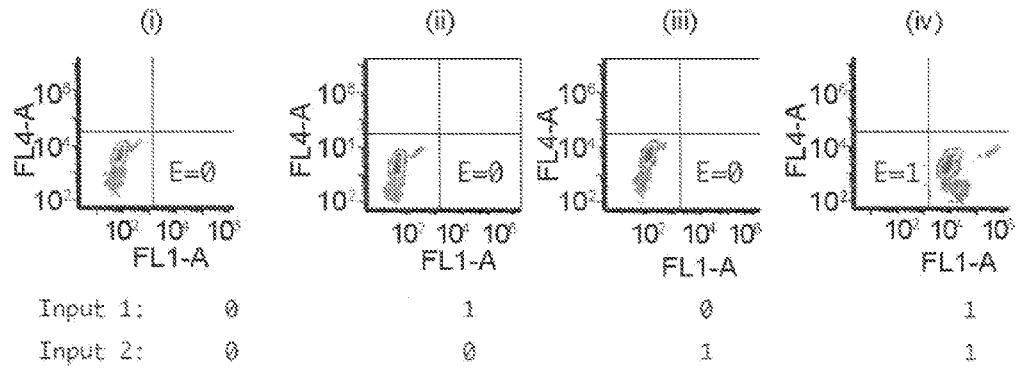
FIGS. 6A-C depict (FACS) analysis of fluorescently labeled nanorobots tested in vivo, in which each panel shows the response of the nanorobots to the presence or absence of either one of the two cues: (i) no cue, (ii) cue 1 present, cue 2 absent, (iii) cue 1 absent, cue 2 present, (iv) both cues present. (A) E architecture providing an AND gate; (B) EP1P2N architecture providing a XOR gate; and (C) EopenN architecture providing a NAND gate.
Figure 6B:
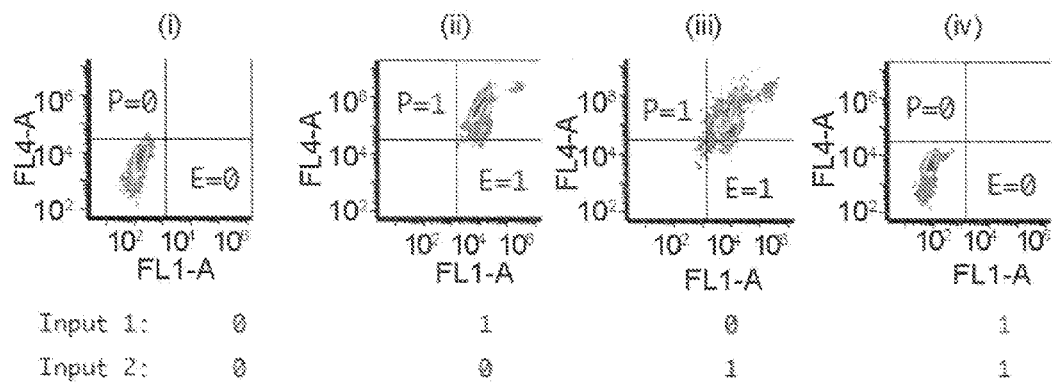
Figure 6C:
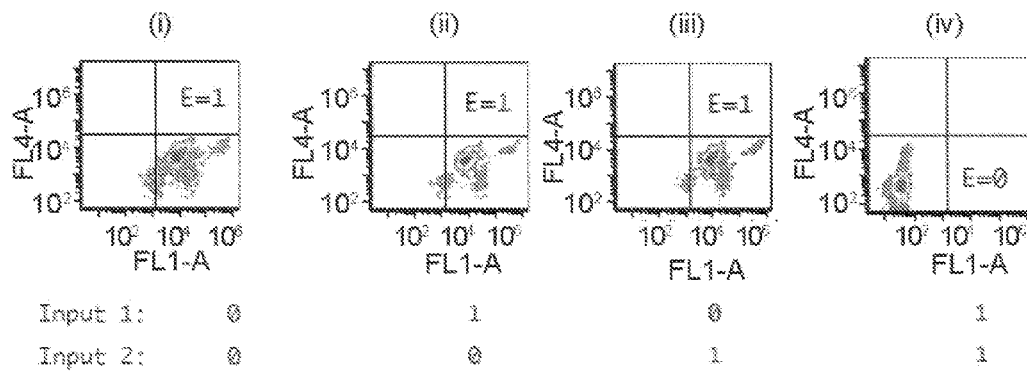
Figure 7:
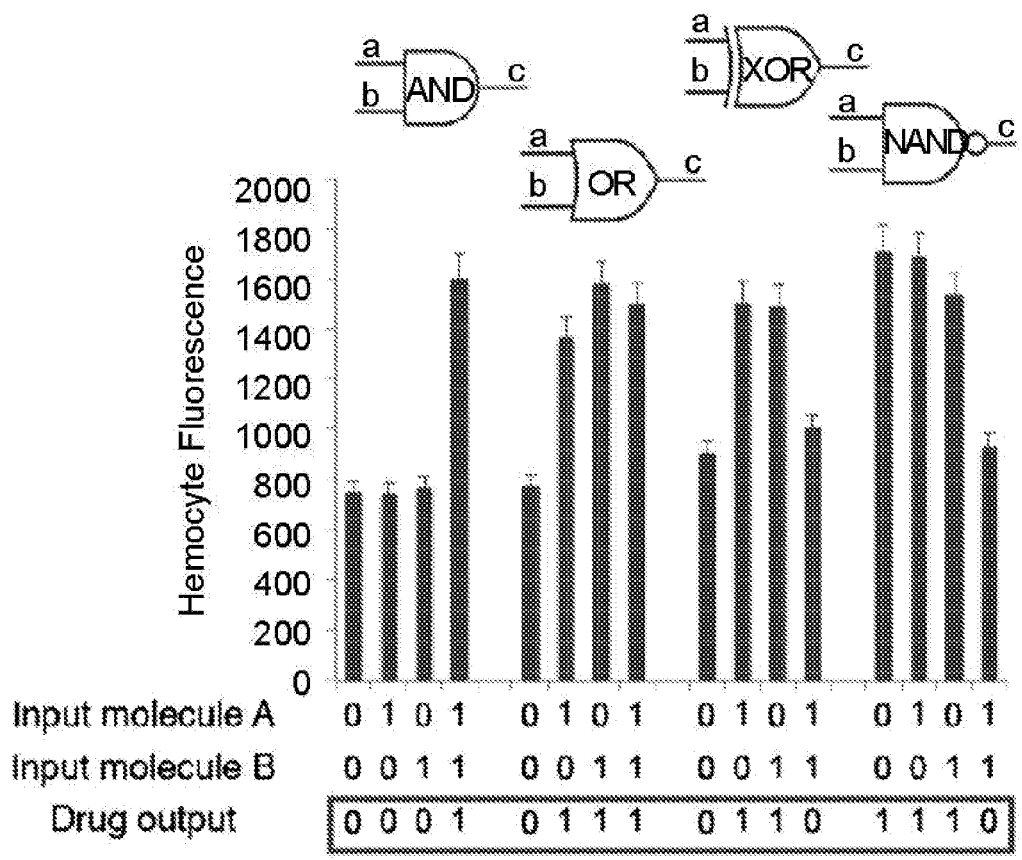
FIG. 7 depicts (FACS) analysis of fluorescently labeled nanorobots responding to two different cues on insect hemocytes in vivo in E architecture providing an AND gate; EP1 architecture providing an OR gate; EP1P2N architecture providing a XOR gate; and EopenN architecture providing a NAND gate.

Architectures based on more than one effector nanorobot (like the EFP1P2N mentioned above) enable to relay output bits to additional therapeutic molecules, forming the basis for more complex gates, reversible logic and binary decoders. To demonstrate such architecture, a controlled NOT (CNOT) gate was designed, consisting of E, P1, P2 and N as described above, and in addition a second effector nanorobot, F, not negated by N, and a positive regulator nanorobot P3 that responds only to X and keys only F. Thus, one input bit is XORed by E and the second output bit is mapped unchanged by F (FIG. 5F). Architectures E (AND; FIG. 6A and FIG. 7), EP1P2 (OR; FIG. 7), EP1P2N (XOR; FIG. 6B and FIG. 7), Eopen:N (NAND; FIG. 6C and FIG. 7), and EFP1P2P3N (CNOT; not shown), prepared at the stoichiometries defined ex-vivo, were examined in living insects and produced good outputs.

A central feature of the collision-based system presented here, as in other forms of unconventional computing, is reversible logic [Liu, D. et al., 2011; Cervera, J. et al., 2010]. This feature enables the original cues to be explicitly inferred from the final states of the nanorobots, consequently revealing important information about the physiological and biochemical condition of the animal. Hence, the system can be used as a diagnostic tool by extracting activated nanorobot complexes and reading their output.

Notably, while aptamer-based gates are very difficult to model in terms of opening kinetics and statistics, toehold-driven displacement gating can be reproducibly designed [Zhang, D. Y. et al., 2011; Zhang, D. Y. et al., 2009] and proved very efficient in this study; however, this obligates the use of nucleic acid cues, ostensibly limiting the application range of our design.

Our findings demonstrate the feasibility of stochastic collision-based computing with diffusing particles in a biological system. The nanorobots, with a ~55,000 cubic nanometer volume and 5 megadalton mass, have a diffusion coefficient in the medium, which is adequate for efficient collisions. However, the findings also emphasize the importance of stoichiometry. Regulators were required at higher quantities than effectors to ensure that effector-regulator collisions result in a high incidence of proper complexes. At a 1:1 ratio, complex formation is plausibly Poisson distributed around ~50% effector-regulator pairs, and ~25% of uncomplexed effectors and regulators. The architectures described here are capable of processing two bits at most. However, the outputs from two "processors" can be cascaded to a third one and increase the processing capacity from 4, 8, 16 bits and so on, with the capacity limited only by the possible number of unique gate-key systems that can be designed.

Figure 8A:
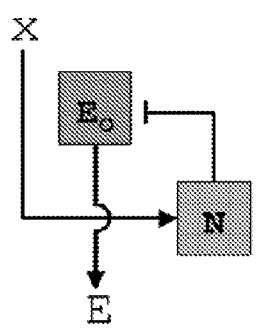
FIGS. 8A-B depict NOT (A) and NAND (B) gates utilized in a multi-type "Asimov system" that shuts down robots doing harm to normal cells.
Figure 8B:
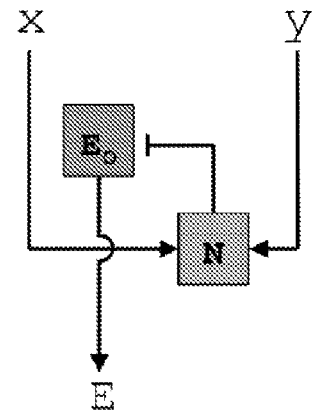

The logical NOT gate explained above can be utilized for a so called Asimov multitype system, in which an effector robot which potentially may harm normal cells is prevented from doing so according to one of the laws of robotics devised by Isaac Asimov which states that "[a] robot may not injure a human being or, through inaction, allow a human being to come to harm". A NOT gate used in an Asimov system may consist of two robot populations: (1) Eo (Eopen) robots—carrying the effector molecule (e.g. drug); and (2) N robots—which close Eo robots in response to damage (i.e. the presence of a damage indicator molecule). Whenever damage indicators leak outside of off-target cells (e.g. a microRNA reflecting damage of normal cells, such as miR-16), N becomes active, and closes E. This interaction requires N to be in a molar excess of ~10 over Eo (FIG. 8A). If one damage indicator is not enough to achieve damaged cell selectivity and discrimination, a multitype Asimov system can also be achieved by a NAND gate. By combining two or more indicators, the identity of the damaged cell can be inferred more precisely (FIG. 8B).

Example 3. DNA Nanorobots Exhibiting Group Behavior

Figure 9:
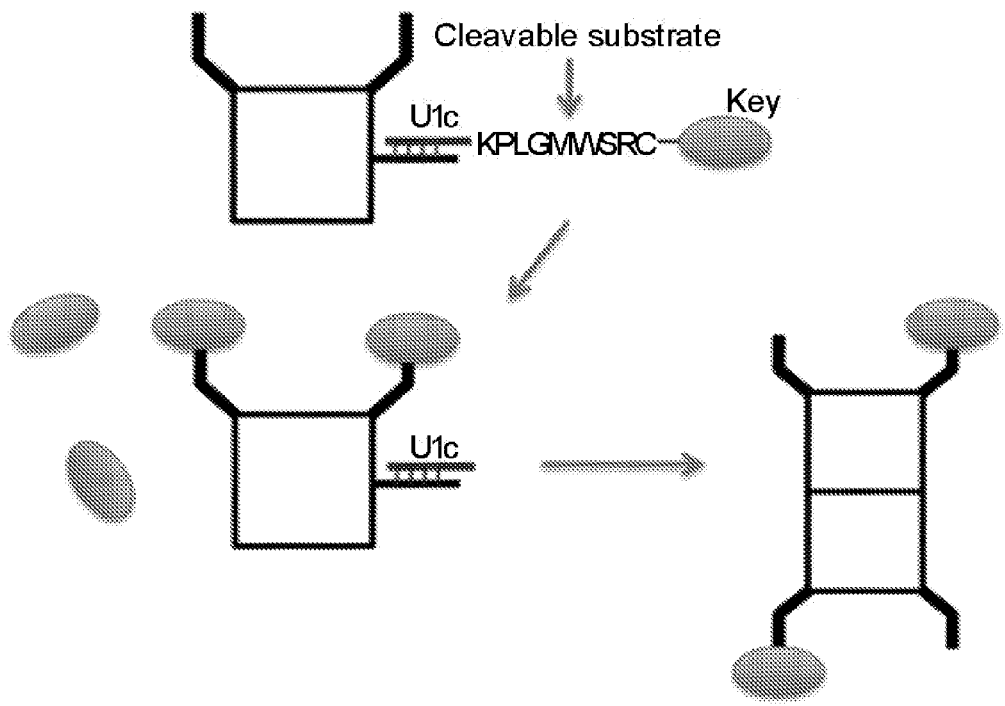
FIG. 9 shows a scheme demonstrating a quorum sensing (QS) signal generator consisting of three components: a selected key, a cleavable tether (substrate); and a DNA tail (U1c) for loading onto a nanorobot loading site (the angled arms coming out from the square representing the nanorobot).
Figure 10:
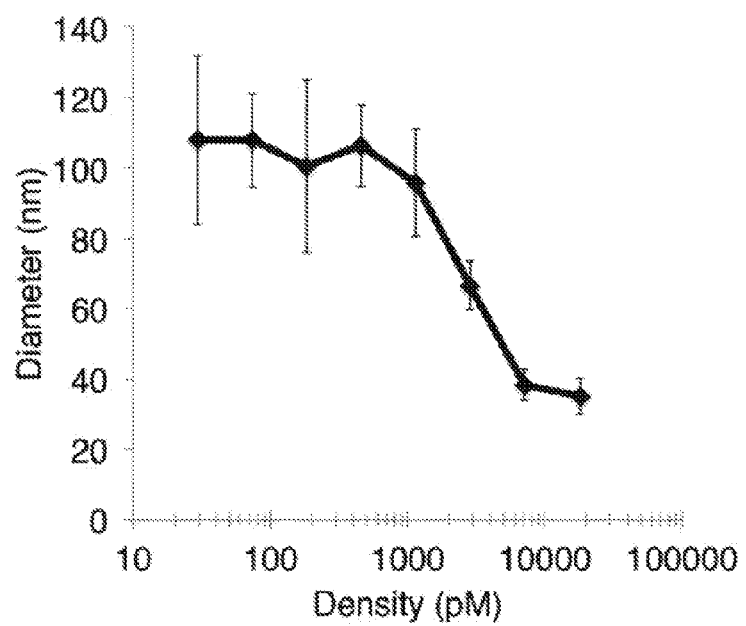
FIG. 10 shows a graph from a dynamic light scattering measurement showing the average diameter of the individual nanorobots as a function of their concentration (density).
Figure 11:
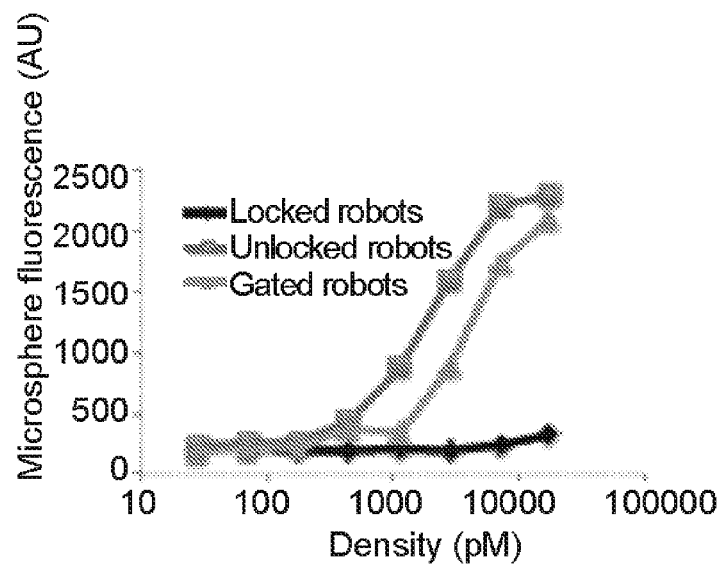
FIG. 11 shows a FACS experiment done as follows: robots tagged fluorescently and loaded with biotin were mixed, in various densities (=concentrations) with avidin-coated microspheres. The results demonstrate that there are two separate affinities: the affinity of biotin to avidin determines fluorescence induced by unlocked robots (squares), while the quorum sensing mechanism determines fluorescence in the gated robots (triangles).

A QS signal generator was constructed by chemically conjugating three components: a selected key, a cleavable tether; and a DNA tail (U1c) for loading onto a nanorobot loading site as previously described [Douglas, S. M. et al., 2012]. The tether is designed to undergo cleavage and generate a diffusing signal in response to certain stimuli. As tethers, we used the peptide tether sequence KPLGMWSRC (SEQ ID NO: 3), which is cleaved by matrix metalloproteinases (MMP) [Park, H. I. et al., 2002]. As key molecule, human platelet-derived growth factor BB (PDGF-BB) was chosen first (FIG. 9). The signal generator U1c-KPLGM-WSRC-PDGF-BB was loaded into the nanorobots, which were then placed in MMP-2-containing buffer at various population densities (from 29 to 18,000 pM nanorobots. Dynamic light scattering demonstrated a density-dependent structural change of the nanorobot indicating switching between states in agreement with previously-described observations[1] (FIG. 10). This observation was repeated using nanorobots loaded with GFP in parallel with the signal generator and mixed with microspheres coated with anti-GFP antibody. Upon addition of MMP-2, the generated signal induced a concentration-dependent activation of the nanorobots and exposure of GFP, subsequently guiding their attachment to the microspheres. Flow cytometric analysis revealed that the behavior of gated nanorobots correlates with the gate's affinity to the QS signal, while unlocked nanorobots showed slightly shifted kinetics correlating with the higher affinity of GFP to its antibody (FIG. 11).

Figure 12:
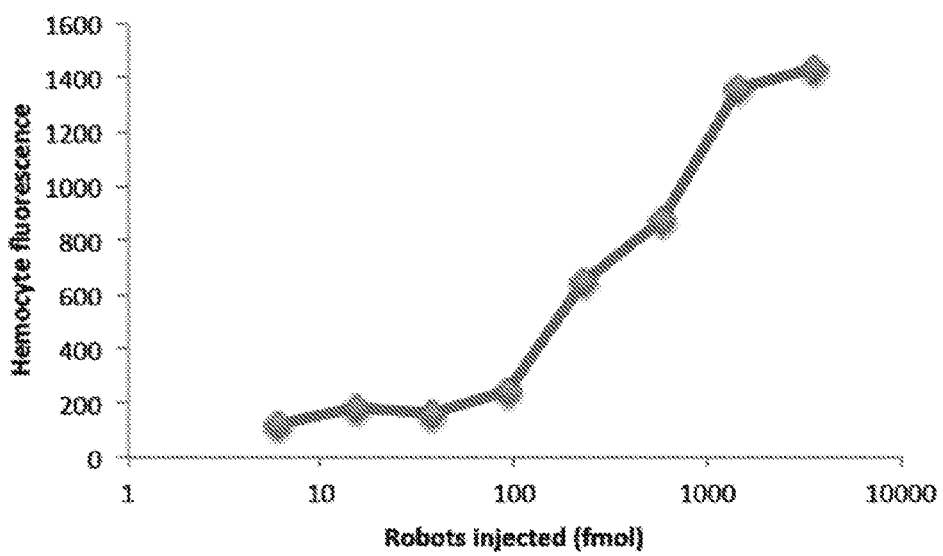
FIG. 12 depicts hemocyte fluorescence resulting from attached fluorescent nanorobots as a function of the amount of nanorobots injected into the insect Blaberus discoidalis. The nanorobots were equipped with a signal generator comprising the tether sequence KIEARC (SEQ ID NO: 1), a substrate of insect prophenol oxidase-activating protease (PAP) and fluorescently labeled anti-insect hemocytes antibody.

This behavior was also examined in a living animal, using the insect *Blaberus discoidalis* as a model organism. Here, a different signal generator was constructed using the tether sequence KIEARC (SEQ ID NO: 1), a substrate of insect prophenol oxidase-activating protease (PAP) [Gupta, S. et al., 2005]. Nanorobots loaded with this generator and with fluorescently labeled anti-insect hemocytes antibody were injected into the hemocoel of adult *B. discoidalis* in increasing quantities. Later, the hemolymph was extracted and hemocytes were analyzed by flow cytometry to reveal the state (open/closed) of the nanorobot population. Our analysis demonstrated a density dependent transition of the nanorobots to an active state in the living insect, relayed to controlling a cell-interacting molecule (FIG. 12).

A potential drawback of the design showed thus far is that the signal generator operates immediately and only once, making it impossible to coordinate a group of nanorobots over a long period. To address this, a continuous signal generator was constructed by storing large amount of QS signal inside small liposomes, which were linked to the nanorobots. The nanorobots were capable of releasing QS signals to the environment over a period of time (not shown).

Figure 13:
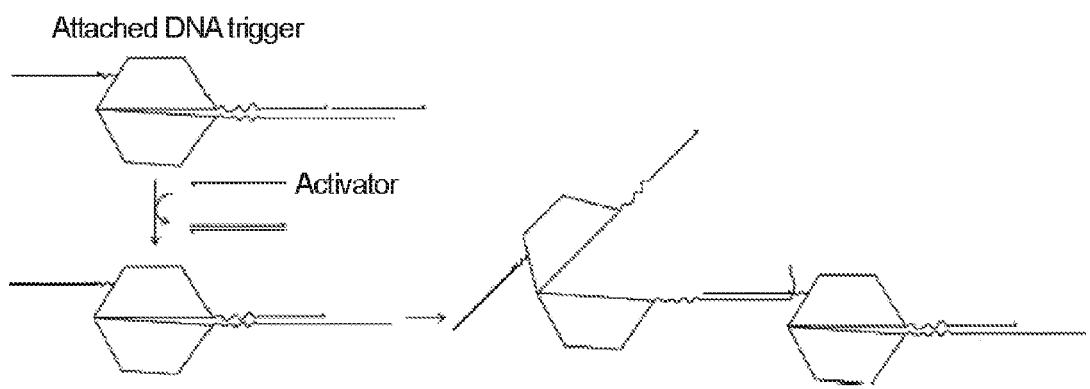
FIG. 13 depicts a scheme showing an example of a nanorobot capable of reversible self-aggregation and activation in a nanorobot concentration-dependent manner.

The nanorobots can be made to aggregate by contacting one or more oligonucleotides presented on the outer surface of each individual nanorobot that is complementary to one or more other oligonucleotide also presented on the outer surface of each individual nanorobot (FIG. 13). The hybridization of each pair of oligonucleotides cause the nanorobots to aggregate. If one of the oligonucleotides is an aptamer initially hybridized to a latch domain, which together keep the nanorobot in a closed configuration, then the hybridization of the other nucleotide to the aptamer will cause the displacement of the latch domain and subsequent opening of the nanorobot. Thus, the interaction between the two oligonucleotides present on the outer surface of the nanorobots may cause both aggregation and opening of the nanorobots. In this way, a drug stowed away inside the nanorobots when in a closed configuration can be released only when the concentration of the nanorobots is high enough to allow aggregation and opening.

Figure 14:
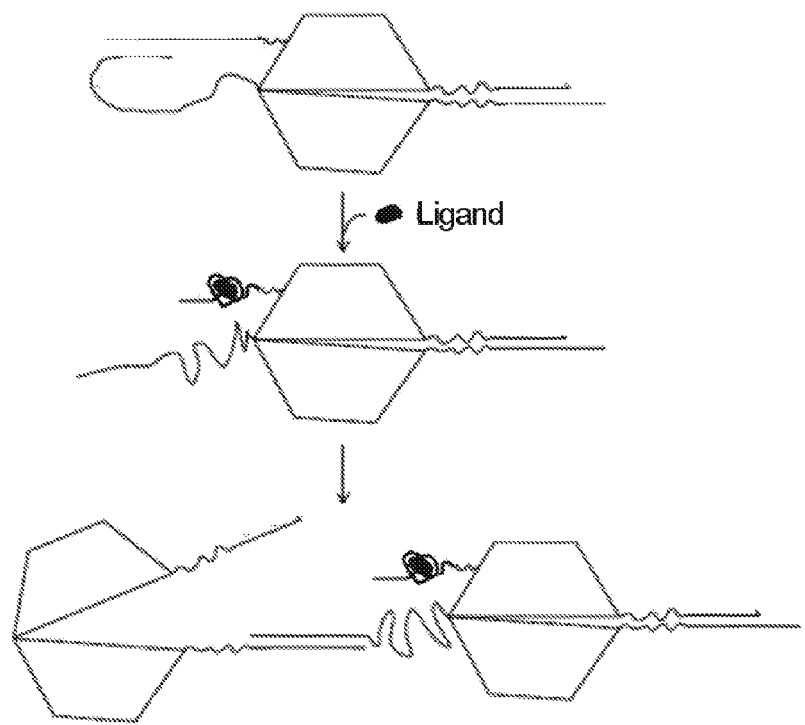
FIG. 14 depicts a scheme showing an example of a nanorobot capable of reversible self-aggregation and activation in a nanorobot concentration-dependent manner that is also dependent on the concentration of a ligand.

The other oligonucleotide mentioned above may be initially kept in an inactive form by binding to a complementary aptamer oligonucleotide. When a ligand binds to the aptamer, the other oligonucleotide is released and free to interact with complementary oligonucleotides on other nanorobots as described above (FIG. 14). The size of an individual nanorobot, as assessed by measuring light scattering, is larger when it is in a closed configuration than when it is in an open configuration. The results (not shown; see FIG. 10 for a similar result) shows that, indeed, the diameter of the individual nanorobots decrease with the increase in nanorobot concentration (density).

Example 4. Controlled Delivery of Drugs by Nanorobots Exhibiting Quorum Sensing

Figure 15:
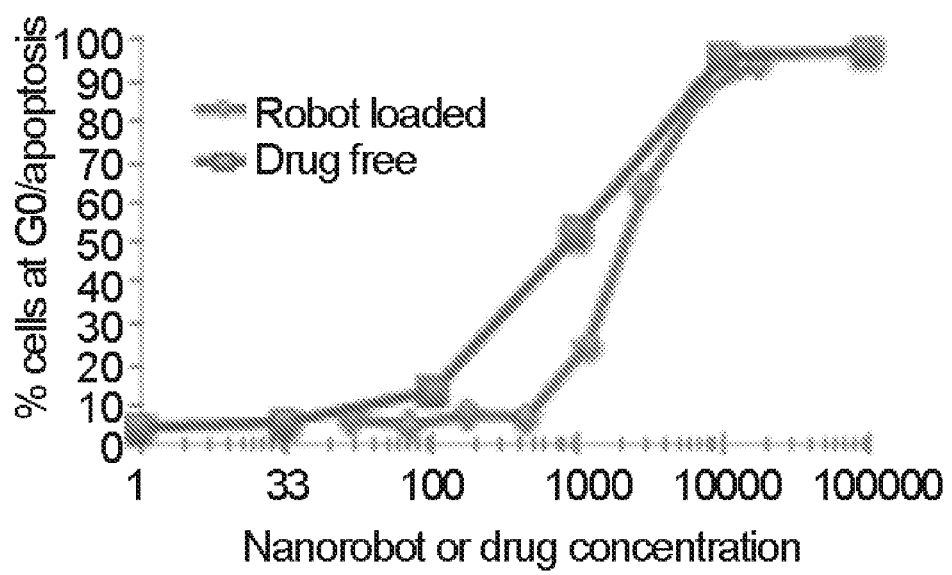
FIG. 15 shows a graph depicting dependency of cell cycle arrest or apoptosis in cancer cells on the concentration of robots loaded with a drug as compared with the free drug. The results demonstrate that the robot-induced effect is different than the drug-induced one and appears at different concentrations. In fact quorum sensing here improved the therapeutic window of the drug because it enabled a higher dose to accumulate without being active until the defined dose was reached.

Robots loaded with a cancer drug were mixed in various concentrations with cancer cells. In a separate sample the free drug was mixed too. The results demonstrate that the robot-induced effect is different than the drug-induced one and appears at different concentrations. In fact, quorum sensing here improved the therapeutic window of the drug because it enabled a higher dose to accumulate without being active until the defined dose was reached (FIG. 15).

REFERENCES

Adamatzky, A., Collision-based computing, 2002, Springer.
Adamatzky, A., de Lacy Costello, B., Collision-free path planning in the Belousov-Zhabotinsky medium assisted by a cellular automaton. *Die Naturwissenschaften*, 2002, 89, 474-478.

Adar, R., Benenson, Y., Linshiz, G., Rosner, A., Tishby, N., Shapiro, E., Stochastic computing with biomolecular automata. *Proceedings of the National Academy of Sciences of the United States of America*, 2004, 101, 9960-9965

Adleman, L. M., Molecular computation of solutions to combinatorial problems. *Science*, 1994, 266, 1021-1024

Bassler, B. L., Losick, R., Bacterially speaking. *Cell*, 2006, 125, 237-246

Benenson, Y., Gil, B., Ben-Dor, U., Adar, R., Shapiro, E., An autonomous molecular computer for logical control of gene expression. *Nature*, 2004, 429, 423-429

Benenson, Y., Paz-Elizur, T., Adar, R., Keinan, E., Livneh, Z., Shapiro, E., Programmable and autonomous computing machine made of biomolecules. *Nature*, 2001, 414, 430-434

Bowler, D. E., Benton, T. G., Causes and consequences of animal dispersal strategies: relating individual behaviour to spatial dynamics. *Biological reviews of the Cambridge Philosophical Society*, 2005, 80, 205-225

Bulmer, M. S., Bachelet, I., Raman, R., Rosengaus, R. B., Sasisekharan, R., Targeting an antimicrobial effector function in insect immunity as a pest control strategy. *Proceedings of the National Academy of Sciences of the United States of America*, 2009, 106, 12652-12657

Braich, R. S., Chelyapov, N., Johnson, C., Rothemund, P. W., Adleman, L., Solution of a 20-variable 3-SAT problem on a DNA computer. *Science*, 2002, 296, 499-502

Cervera, J., Mafe, S., Multivalued and reversible logic gates implemented with metallic nanoparticles and organic ligands. *Chemphyschem: a European journal of chemical physics and physical chemistry*, 2010, 11, 1654-1658

Chang, W. L., Ho, M. S., Guo, M., Molecular solutions for the subset-sum problem on DNA-based supercomputing. *Bio Systems*, 2004, 73, 117-130

Chen, J. H., Seeman, N. C., Synthesis from DNA of a molecule with the connectivity of a cube. *Nature*, 1991, 350, 631-633

Dietz, H., Douglas, S. M., Shih, W. M. Folding DNA into twisted and curved nanoscale shapes. *Science*, 2009, 325, 725-730

Douglas, S. M., Bachelet, I., Church, G. M. A logic-gated nanorobot for targeted transport of molecular payloads. *Science*, 2012, 335, 831-834

Douglas, S. M., Dietz, H., Liedl, T., Hogberg, B., Graf, F., Shih, W. M., Self-assembly of DNA into nanoscale three-dimensional shapes. *Nature*, 2009, 459, 414-418

Engebrecht, J., Silverman, M., Identification of genes and gene products necessary for bacterial bioluminescence. *Proceedings of the National Academy of Sciences of the United States of America*, 1984, 81, 4154-4158

Enomoto, A., Moore, M., Nakano, T., A molecular communication system using a network of cytoskeletal filaments. *Nanotechnology Conference and Trade Show*, 2006, 725-728

Garbutt, J. S., Belles, X., Richards, E. H., Reynolds, S. E. Persistence of double stranded RNA in insect hemolymph as a potential determiner of RNA interference success: Evidence from *Manduca sexta* and *Blattella germanica*. *Journal of insect physiology*, 2012

Gupta, S., Wang, Y., Jiang, H., *Manduca sexta* prophenoloxidase (proPO) activation requires proPO-activating proteinase (PAP) and serine proteinase homologs (SPHs) simultaneously. *Insect biochemistry and molecular biology*, 2005, 35, 241-248

Gregori, M., Llatser, I., Cabellos-Aparicio, A., Alarcon, E., Physical channel characterization for medium-range nanonetworks using flagellated bacteria. *Computer Networks,* 2011, 55, 779-791

Gregori, M., Llatser, I., Cabellos-Aparicio, A., Alarcón, E., Physical channel characterization for medium-range nanonetworks using catalytic nanomotors. *Nano Communication Networks,* 2010, 1, 102-107

Gregorim M., Akyildizm I., A new nanonetwork architecture using flagellated bacteria and catalytic nanomotors. *IEEE Journal on Selected Areas in Communications,* 2010, 28, 612-619

Grossman, A. D., Genetic networks controlling the initiation of sporulation and the development of genetic competence in *Bacillus subtilis. Annual review of genetics,* 1995, 29, 477-508

Hauzy, C., Hulot, F. D., Gins, A., Loreau, M., Intra- and interspecific density-dependent dispersal in an aquatic prey-predator system. *The Journal of animal ecology,* 2007, 76, 552-558

Hentzer, M., Wu, H., Andersen, J. B., Riedel, K., Rasmussen, T. B., Bagge, N., Kumar, N., Schembri, M. A., Song, Z., Kristoffersen, P., Manefield, M., Costerton, J. W., Molin, S., Eberl, L., Steinberg, P., Kjelleberg, S., Høiby, N., Givskov, M., Attenuation of *Pseudomonas aeruginosa* virulence by quorum sensing inhibitors. *The EMBO journal,* 2003, 22, 3803-3815

Hiyama, S., Inoue, T., Shima, T., Moritani, Y., Suda, T., Sutoh, K., Autonomous loading, transport, and unloading of specified cargoes by using DNA hybridization and biological motor-based motility. *Small,* 2008 (a), 4, 410-415

Hiyama, S., Moritani, Y., Molecular communication: Harnessing biochemical materials to engineer biomimetic communication systems. *Nano Communication Networks,* 2010, 1, 20-30

Hiyama, S., Moritani, Y., Suda, T., A biochemically-engineered molecular communication system. *Nano-Net,* 2009, 85-94

Hiyama, S., Moritani, Y., Suda, T., Molecular communication, *Proceedings NSTI Nanotechnology Conference and Trade Show,* 2005, 3, 391-394

Hiyama, S., Moritani, Y., Suda, T., Shima, T., Sutoh, K., An autonomous molecular transport system using DNAs and motor proteins in molecular communication, *Bio-Inspired Models of Network, Information and Computing Systems,* 2007, 135-138

Hiyama, S., Takeuchi, S., Gojo, R., Shima, T., Sutoh, K., Biomolecular motor-based cargo transporters with loading/unloading mechanisms on a micro-patterned DNA array. *IEEE 21st International Conference on Micro Electro Mechanical Systems,* 2008 (b), 144-147

Karels, T. J., Boonstra, R., Concurrent density dependence and independence in populations of arctic ground squirrels. *Nature,* 2000, 408, 460-463

Kim, S. Y., Tones, R., Drummond, H., Simultaneous positive and negative density-dependent dispersal in a colonial bird species. *Ecology,* 2009, 90, 230-239

Lerat, E., Moran, N. A., The evolutionary history of quorum-sensing systems in bacteria. *Molecular biology and evolution,* 2004, 21, 903-913

Liu, D., Chen, W., Sun, K., Deng, K., Zhang, W., Wang, Z., Jiang, X., Resettable, multi-readout logic gates based on controllably reversible aggregation of gold nanoparticles. *Angewandte Chemie International Edition,* 2011, 50, 4103-4107

Llatser, I., Cabellos-Aparicio, A., Alarcon, E., Networking Challenges and Principles in Diffusion-based Molecular Communication, *Wireless Communications, IEEE,* 2012, 19, 36-41

Miller, M. B., Skorupski, K., Lenz, D. H., Taylor, R. K., Bassler, B. L., Parallel quorum sensing systems converge to regulate virulence in *Vibrio cholerae. Cell,* 2002, 110, 303-314

Moritani, Y., Hiyama, S., Nomura, S. M., Akiyoshi, K., Suda, T., A Communication interface using vesicles embedded with channel forming proteins in molecular communication. *Bio-Inspired Models of Network, Information and Computing Systems,* 2007, 147-149

Moritani, Y., Hiyama, S., Suda, T., Molecular communication among nanomachines using vesicles. *Proceedings of 2006 NSTI Nanotechnology Conference,* 2006, 705-708

Nakano, T., Suda, T., Moore, M., Molecular communication for nanomachines using intercellular calcium signaling. *Proceedings of 2005 5th IEEE Conference on Nanotechnology,* 2005

Nephew, B. C., Romero, L. M., Behavioral, physiological, and endocrine responses of starlings to acute increases in density. *Hormones and behavior,* 2003, 44, 222-232

Parcerisa Giné, L., Akyildiz, I. F., Molecular communication options for long range nanonetworks. *Computer Networks,* 2009, 53, 2753-2766

Park, H. I., Turk, B. E., Gerkema, F. E., Cantley, L. C., Sang, Q. X., Peptide substrate specificities and protein cleavage sites of human endometase/matrilysin-2/matrix metalloproteinase-26. *The Journal of biological chemistry,* 2002, 277, 35168-35175

Pierobon, M., Akyildiz, I., A physical end-to-end model for molecular communication in nanonetworks. *IEEE Journal on Selected Areas in Communications,* 2010, 28, 602-611

Qian, L., Winfree, E., Bruck, J., Neural network computation with DNA strand displacement cascades. *Nature,* 2011, 475, 368-372

Rinaudo, K., Bleris, L., Maddamsetti, R., Subramanian, S., Weiss, R., Benenson, Y., A universal RNAi-based logic evaluator that operates in mammalian cells. *Nature biotechnology,* 2007, 25, 795-801

Rothemund, P. W., Folding DNA to create nanoscale shapes and patterns. *Nature,* 2006, 440, 297-302

Seeman, N. C. Nucleic acid junctions and lattices. *Journal of theoretical biology,* 1982, 99, 237-247

Suda, T., Nakano, T., Moore, M., Biologically inspired approaches to networks: The bio-networking architecture and the molecular communication. *Bio-Inspired Computing and Communication. Lecture Notes in Computer Science,* 2008, 5151, 241-254

Walsh, F., et al., Synthetic protocols for nano sensor transmitting platforms using enzyme and DNA based computing. *Nano Communication Networks,* 2010, 1, 50-62

Winfree, E., et al, Design and self-assembly of two-dimensional DNA crystals. *Nature,* 1998, 394, 539-544

Xie, Z., et al., Y. Multi-input RNAi based logic circuit for identification of specific cancer cells. *Science,* 2011, 333, 1307-1311

Yeh, C. W., Chu, C. P., Wu, K. R., Molecular solutions to the binary integer programming problem based on DNA computation. *Bio Systems,* 2006, 83, 56-66

Yin, Z., et al. Chinese Postman Problem based on DNA computing. *Journal of chemical information and computer sciences,* 2002, 42, 222-224

The invention claimed is:

1. A system acting as a logic gate, said system comprising at least one effector device, at least one regulator device, at least one input and at least one output, wherein each one of said at least one effector device and at least one regulator device is a nucleic acid origami device comprising a scaffold strand and a plurality of staple strands, and independently has the structure A, B or C, wherein:

in the structure A:

(i) one of the staple strands comprises either (a) an aptamer domain capable of binding to a binding partner comprising a first of said at least one input; (b) an oligonucleotide capable of binding to a binding partner comprising a DNA binding protein, said DNA binding protein comprising a second of said at least one input; or (c) an oligonucleotide attached to a nano-antenna capable of receiving an electromagnetic field comprising a third of said at least one input, or one of the staple strands comprises an aptamer domain of (a) and another of the staple strands comprises an oligonucleotide of (c);

(ii) another of the staple strands comprises a latch domain hybridized or bound to said aptamer domain of (a) or oligonucleotide of (b) or (c), the sequence of the latch domain being selected such that the aptamer domain of (a) is capable of binding to the binding partner such that the binding partner displaces the latch domain, or the latch domain is capable of hybridizing with an external oligonucleotide selected such that the external oligonucleotide displaces the aptamer domain; said latch domain is linked to a binding partner that is selected such that the binding partner has a first configuration under a first condition and a different second configuration under a different second condition, and the aptamer of (a) or the oligonucleotide of (b) is capable of binding to the binding partner having the first configuration but incapable of binding to the binding partner having the second configuration such that the latch domain is displaced from the aptamer of (a) or the oligonucleotide of (b) when the binding partner transitions from the first to the second configuration; or the nano-antenna of (c), upon receipt of said electromagnetic field, undergoes inductive coupling and subsequent heating thereby displacing the latch domain from the oligonucleotide of (c); and (iii) the aptamer domain of (a) or the oligonucleotide of (b) or (c), and the latch domain, when hybridized or bound to one another, hold the device in a closed configuration; and the device transitions to an open configuration when the aptamer domain of (a) or the oligonucleotide of (b) or (c), and the latch domain, are not hybridized or bound to one another, in the structure B:

(i) one of the staple strands comprises a first aptamer domain capable of binding to a first binding partner comprising one of said at least one input;

(ii) another of the staple strands comprises a second aptamer domain capable of binding to a second binding partner comprising another one of said at least one input;

(iii) still another of the staple strands comprises a first latch domain hybridized to the first aptamer domain, the sequence of the first latch domain being selected such that the first aptamer domain is capable of binding to the first binding partner such that the first binding partner displaces the first latch domain, or the first latch domain is capable of hybridizing with an external oligonucleotide selected such that the external oligonucleotide displaces the aptamer domain;
(iv) yet another of the staple strands comprises a second latch domain hybridized to the second aptamer domain, the sequence of the second latch domain being selected such that the second aptamer domain is capable of binding to the second binding partner such that the second binding partner displaces the second latch domain, or the second latch domain is capable of hybridizing with an external oligonucleotide selected such that the external oligonucleotide displaces the aptamer domain; and
(v) said nucleic acid origami device is in a closed configuration when the first aptamer domain is hybridized to the first latch domain and/or the second aptamer domain is hybridized to the second latch domain; and the device transitions to an open configuration when the first aptamer domain is not hybridized to the first latch domain and the second aptamer domain is not hybridized to the second latch domain,
in the structure C:
(i) two of the staple strands each comprises a latch domain linked to an oligonucleotide capable of hybridizing with an external oligonucleotide, said external oligonucleotide is positioned on another one of said nucleic acid origami devices; and
(ii) said nucleic acid origami device is in an open configuration when each one of the oligonucleotide capable of hybridizing with an external oligonucleotide is not hybridized to said external oligonucleotide; and the device transitions to a closed configuration when each oligonucleotide capable of hybridizing with an external oligonucleotide is hybridized to said external oligonucleotide,
wherein
each one of said at least one effector nucleic acid origami device and at least one regulator nucleic acid origami device is either alkylated, acylated or hydroxylated, or interacts with a compound capable of non-covalently binding to the major- or minor-groove of a double stranded nucleic acid, and therefore is resistant to nucleases, or
each one of said at least one effector nucleic acid origami device and at least one regulator nucleic acid origami device lacks TLR9 recognition elements or the TLR9 recognition elements of said nucleic acid origami device are masked or modified and therefore said nucleic acid origami device is non-immunogenic.

2. The system of claim 1, wherein each one of said nucleic acid origami devices is methylated.

3. The system of claim 2, wherein said compound capable of non-covalently binding to the major- or minor-groove of a double stranded nucleic acid is selected from the group consisting of netropsin, distamycin, an oligoamide, a sugar-oligoamide conjugate and a bis-amidine.

4. The system of claim 1, wherein one or more further staple strands in at least one of said nucleic acid origami devices each comprises a handle domain bound to a payload, optionally via a linker, thereby providing for one or more payloads in at least one of said nucleic acid origami devices, wherein at least one of said payload(s) is one of said at least one output, and optionally, at least one of said payload(s) is one of said at least one input or emulates one of said at least one input.

5. The system of claim 4, wherein said linker comprises an oligonucleotide having a sequence complementary to the sequence of the handle domain and optionally comprising a further domain comprising a recognition site for enzymatic cleavage, and the payload is bound to the handle domain through the hybridization of the oligonucleotide to the handle domain, said further domain optionally comprising a peptide linker comprising a protease recognition site for cleavage by a protease or wherein said linker comprises a protein capable of binding a small-molecule.

6. The system of claim 4, wherein said payload each independently is a drug selected from the group consisting of insulin, an antibody or a fragment thereof, a cell surface receptor ligand or a biologically active fragment thereof, a small molecule, a nucleic acid molecule, an oligonucleotide, a nuclease, an aptamer, a lipid, a glycan, a protein, a glycoprotein, a glycolipid, a nanoparticle, a fluorophore, a radioactive compound, a nano-antenna, and a liposome.

7. The system of claim 4, wherein the plurality of staple strands are selected such that at least one of the payloads is positioned on an inner surface of the nucleic acid origami device when the device is in the closed configuration; and the transition to the open configuration causes said payload to be positioned on an outer surface of the nucleic acid origami device, or wherein one of the staple strands in at least one of said nucleic acid origami devices comprises a handle domain positioned on an outer surface of the device when the device is in the closed configuration; and the transition to the open configuration causes said payload to be positioned on an inner surface of the nucleic acid origami device, optionally wherein the handle domain is bound to a payload selected from the group consisting of an oligonucleotide and a liposome.

8. The system of claim 1, wherein:
(i) in at least one of said nucleic acid origami devices having the structure A or B, the plurality of staple strands are selected such that said nucleic acid origami device(s) comprises a first domain and a second domain, wherein the first domain comprises said aptamer domain of (a) capable of binding to a binding partner; said oligonucleotide of (b) capable of binding a DNA binding protein; or said oligonucleotide of (c), attached to a nano-antenna; and the second domain comprises said latch domain of structure A or said first or second latch domain of structure B,
wherein a first end of the first domain is attached to a first end of the second domain by at least one single-stranded nucleic acid hinge and the second end of the first domain is attached to the second end of the second domain by the hybridization or binding of each one of said aptamer domain or oligonucleotide to said latch domains, respectively; or
(ii) in at least one of said nucleic acid origami devices having the structure C, the plurality of staple strands are selected such that said nucleic acid origami device(s) comprises a first domain and a second domain, wherein each one of said first and second domains comprises one of said latch domains linked to an oligonucleotide capable of hybridizing with an external oligonucleotide,
wherein a first end of the first domain is attached to a first end of the second domain by at least one single-stranded nucleic acid hinge and the second end of the first domain is not attached to the second end of the second domain.

9. The system of claim 8, wherein
(i) the plurality of staple strands in at least one of said nucleic acid origami devices having the structure A or B are selected such that the second end of the first domain becomes unattached to the second end of the second domain if said aptamer domain is contacted by its respective binding partner or if said nano-antenna receives an electromagnetic field and undergoes inductive coupling and subsequent heating; or (ii) the plurality of staple strands in at least one of said nucleic acid origami devices having the structure C are selected such that the second end of the first domain becomes attached to the second end of the second domain if each one of said latch domains is hybridized to a different external oligonucleotide.

10. The system of claim 1, wherein each one of said binding partner independently is an antigen selected from the group consisting of a tumor associated antigen, a cell-membrane receptor, a secreted or membrane bound growth factor, a hormone, a cytokine, a ligand, a chemokine, a bacterial antigen, a viral antigen, a parasitic antigen, a lipid, an oligonucleotide, a sugar; a signal molecule, an enzyme or a DNA binding protein.

11. The nucleic acid origami device of claim 10, wherein said enzyme is a glucokinase and said aptamer domain of (a) is capable of binding to the glucokinase having the first configuration but is incapable of binding to the glucokinase having the second configuration; or the DNA binding protein is a glucose response factor and said oligonucleotide of (b) is a glucose responsive regulatory element capable of binding to the glucose response factor having the first configuration but incapable of binding to the glucose response factor having the second configuration.

12. The system of claim 10 comprising one effector device having one or more handle domains each bound to a payload, at least one regulator device, at least one input and one output, wherein said output has a first output state when said effector device is in the closed configuration and a second output state when said effector device is in the open configuration, wherein the first output state corresponds to a logical off state and the second output state corresponds to a logical on state, the gate being selected from the group consisting of (a) a logical NAND gate, comprising two inputs, and being in a logical on state if both inputs are absent, the system comprising one effector device and one regulator device, wherein
  (i) said effector device has the structure C and is initially in an open configuration; and
  (ii) said regulator device is a negative regulator device having the structure B and comprising two handle domains each bound to a nucleic acid molecule acting as a signal molecule capable of hybridizing to a different one of said latch domains of said effector device, said negative regulator device is initially in a closed configuration wherein said signal molecule is positioned on an inner surface of the negative regulator device and, when both inputs are present, transitions to an open configuration wherein said signal molecule is positioned on an outer surface of the negative regulator device,
  wherein the gate is in a logical on state when each signal molecule hybridizes to a different one of said latch domains of said effector device thereby promoting closure of the effector device or preventing transition of the effector device to an open configuration; (b) a logical NOT gate, comprising one input, and being in a logical on state if the input is absent, the system comprising one effector device and one regulator device, wherein
  (i) said effector device has the structure C and is initially in an open configuration; and
  (ii) said regulator device is a negative regulator device having the structure A and comprising two handle domains each bound to a nucleic acid molecule acting as a signal molecule capable of hybridizing to a different one of said latch domains of said effector device, said negative regulator device is initially in a closed configuration wherein said signal molecule is positioned on an inner surface of the negative regulator device and, when the input is present, transitions to an open configuration wherein said signal molecule is positioned on an outer surface of the negative regulator device,
  wherein the gate is in a logical on state when each signal molecule hybridizes to a different one of said latch domains of said effector device thereby promoting closure of the effector device or preventing transition of the effector device to an open configuration; (c) a logical implicit OR gate, comprising two inputs, and being in a logical on state if at least one of the two inputs is present, the system comprising one effector device and two regulator devices, wherein
  (i) said effector device has the structure B, is initially in a closed configuration and, when both inputs are present, transitions to an open configuration;
  (ii) the first of said two regulator devices is a first positive regulator device having the structure A and comprises one handle domain bound to a nucleic acid molecule acting as a signal molecule capable of emulating the second of said two inputs by hybridizing to the aptamer domain of said effector device that is capable of binding to the second of said two inputs, said first positive regulator device is initially in a closed configuration wherein said signal molecule is positioned on an inner surface of said first positive regulator device and, when the first of said two inputs is present, transitions to an open configuration wherein said signal molecule is positioned on an outer surface of the positive regulator device; and
  (iii) the second of said two regulator devices is a second positive regulator device having the structure A and comprises one handle domain bound to a nucleic acid molecule acting as a signal molecule capable of emulating the first of said two inputs by hybridizing to the aptamer domain of said effector device that is capable of binding to the first of said two inputs, said second positive regulator device is initially in a closed configuration wherein said signal molecule is positioned on an inner surface of said second positive regulator device and, when the second of said two inputs is present, transitions to an open configuration wherein said signal molecule is positioned on an outer surface of the positive regulator device,
  wherein the gate is in a logical on state when:
  the first of said two inputs binds to the aptamer domain of the effector device capable of binding to the first of said two inputs and the second of said two inputs binds to the aptamer domain of the effector device capable of binding to the second of said two inputs, such that the first of said two inputs displaces the latch domain initially hybridized to said aptamer domain of the effector device capable of binding to the first of said two inputs, and the second of said two inputs displaces the latch domain initially hybridized to said aptamer domain of the effector device capable of binding to the second of said two inputs;
  the first of said two inputs binds to the aptamer domain of said effector device capable of binding to the first of said two inputs and the signal molecule of the first positive regulator device hybridizes to the aptamer domain of said effector device capable of binding to the second of said two inputs, such that the first input displaces the latch domain initially hybridized to said aptamer domain of the effector device capable of binding to the first of said two inputs and the signal molecule of the first positive regulator device displaces the latch domain initially hybridized to said aptamer domain capable of binding to the second of said two inputs; or the second of said two inputs binds to the aptamer domain of said effector device capable of binding to the second of said two inputs and the signal molecule of the second positive regulator device hybridizes to the aptamer domain of said effector device capable of binding to the first of said two inputs, such that the second input displaces the latch domain initially hybridized to said aptamer domain of the effector device capable of binding to the second of said two inputs and the signal molecule of the second positive regulator device displaces the latch domain initially hybridized to said aptamer domain capable of binding to the first of said two inputs, respectively; and (d) a logical exclusive OR (XOR) gate, comprising two inputs, and being in a logical on state if only one of the two inputs is present, the system comprising one effector device and three regulator devices, wherein (i) said effector device has the structure B, is initially in a closed configuration and, when both inputs are present, transitions to an open configuration;

(ii) the first of said three regulator devices is a first positive regulator device having the structure A and comprises one handle domain bound to a first nucleic acid molecule acting as a first signal molecule capable of emulating the second of said two inputs by hybridizing to the first aptamer domain of said effector device that is capable of binding to the second of said two inputs, said first positive regulator device is initially in a closed configuration wherein said first signal molecule is positioned on an inner surface of said first positive regulator device and, when the first of said two inputs is present, transitions to an open configuration wherein said first signal molecule is positioned on an outer surface of the positive regulator device;

(iv) the second of said three regulator devices is a second positive regulator device having the structure A and comprises one handle domain bound to a second nucleic acid molecule acting as a second signal molecule capable of emulating the first of said two inputs by hybridizing to the aptamer domain of said effector device that is capable of binding to the first of said two inputs, said second positive regulator device is initially in a closed configuration wherein said second signal molecule is positioned on an inner surface of said second positive regulator device and, when the second of said two inputs is present, transitions to an open configuration wherein said signal molecule is positioned on an outer surface of the positive regulator device; and (v) the third of said three regulator devices is a negative regulator device having the structure B and comprising two handle domains each bound to a third nucleic acid molecule acting as a third signal molecule capable of hybridizing to a different one of said latch domains of said effector device, said negative regulator device is initially in a closed configuration wherein each one of said third signal molecule is positioned on an inner surface of the negative regulator device and, when both inputs are present, transitions to an open configuration wherein each one of said signal molecule is positioned on an outer surface of the negative regulator device, wherein the gate is in a logical on state when:

the first of said two inputs binds to the first aptamer domain of said effector device capable of binding to the first of said two inputs and the signal molecule of the first positive regulator device hybridizes to the second aptamer domain of said effector device capable of binding to the second of said two inputs, such that the first input displaces the latch domain initially hybridized to said first aptamer domain of the effector device capable of binding to the first of said two inputs and the signal molecule of the first positive regulator device displaces the latch domain initially hybridized to said second aptamer domain of the effector device capable of binding to the second of said two inputs, respectively; or the second of said two inputs binds to the second aptamer domain of said effector device capable of binding to the second of said two inputs and the signal molecule of the second positive regulator device hybridizes to the first aptamer domain of said effector device capable of binding to the first of said two inputs, such that the second input displaces the latch domain initially hybridized to said second aptamer domain of the effector device capable of binding to the second of said two inputs and the signal molecule of the second positive regulator device displaces the latch domain initially hybridized to said first aptamer domain of the effector device capable of binding to the first of said two inputs, and wherein both inputs are present, the first of said two inputs binds to the first aptamer domain of the effector device capable of binding to the first of said two inputs and the second of said two inputs binds to the second aptamer domain of the effector device capable of binding to the second of said two inputs, such that said first of said two inputs displaces the latch domain initially hybridized to said first aptamer domain of the effector device capable of binding to the first of said two inputs and said second of said two inputs displaces the latch domain initially hybridized to said second aptamer domain of the effector device capable of binding to the second of said two inputs, and each signal molecule of the negative regulator device hybridizes to a different latch domain of said effector device thereby promoting closure of the effector device or preventing transition of the effector device to an open configuration.

13. The system of claim 10, comprising two effector devices each having one or more handle domains each bound to a different payload, at least one regulator device, at least one input and two outputs, wherein the first of said two outputs has a first output state when the first of said two effector devices is in the closed configuration and a second output state when the first of said two effector devices is in the open configuration; and the second of said two outputs has a first output state when the second of said two effector devices is in the closed configuration and a second output state when the second of said two effector devices is in the open configuration, optionally wherein each one of said first output states corresponds to a logical off state and each one of said second output states corresponds to a logical on state.

14. A system exhibiting quorum sensing comprising a plurality of effector nucleic acid origami devices each as defined in claim 1 or a plurality of members selected from the group consisting of liposomes, particles and artificial cells; at least one input; and at least one output, wherein said plurality of effector nucleic acid origami devices or members aggregates at a predetermined concentration, and wherein:
(i) each one of the effector nucleic acid origami devices, having the structure A, B or C, comprises a first handle domain bound to a first oligonucleotide capable of hybridizing with an aptamer domain of another of said effector nucleic acid origami devices having the structure A or B and positioned on the outer surface of the device when the device is in the closed configuration; or
(ii) each one of the members comprises on an outer surface thereof (a) a staple strand comprising a first handle domain bound to a first oligonucleotide; and (b) a further staple strand comprising a second oligonucleotide selected such that the second oligonucleotide is capable of hybridizing to a first oligonucleotide of another of said plurality of members,
wherein the first oligonucleotide is capable of acting as one output and an input for each one of the effector nucleic acid origami devices and an input for another of said effector nucleic acid origami devices, and each one of said effector nucleic acid origami devices or members having an open and a closed configuration and is initially in the closed configuration.

15. The system of claim 14, wherein upon aggregation of said plurality of effector nucleic acid origami devices, said first oligonucleotide of each one of said effector nucleic acid origami devices binds to said aptamer domain of another of said effector nucleic acid origami devices such that the first oligonucleotide, acting as the first of said at least one input, displaces the latch domain of said another of said effector nucleic acid origami devices, thereby promoting transition of said another of said effector nucleic acid origami devices to an open configuration.

16. The system of claim 14, wherein each one of said effector nucleic acid origami devices or each one of said members comprises yet a further staple strand comprising an aptamer capable of binding to a binding partner acting as another of said at least one input.

17. The system of claim 14, wherein each one of said effector nucleic acid origami devices or members further comprises a second handle domain bound to a quorum sensing molecule, optionally via a linker, said quorum sensing molecule acting as a further one of said at least one input, wherein said linker comprises a third oligonucleotide having a sequence complementary to the sequence of the second handle domain and optionally a further domain comprising a recognition site for enzymatic cleavage, and the quorum sensing molecule is bound to the second handle domain through the hybridization of the third oligonucleotide to the handle domain and optionally a further domain comprising a recognition site for enzymatic cleavage, and the quorum sensing molecule is bound to the second handle domain through the hybridization of the third oligonucleotide to the second handle domain, said further domain preferably comprising a peptide linker comprising a protease recognition site for cleavage by a protease, such as a matrix metalloproteinase.

18. The system of claim 14, wherein each one of said effector nucleic acid origami devices or members further comprises a third handle domain bound to a quorum sensing molecule optionally via a linker, said quorum sensing molecule acting as a further one of said at least one input, said linker comprising a third oligonucleotide having a sequence complementary to the sequence of the third handle domain and optionally a further domain comprising a recognition site for enzymatic cleavage, and the quorum sensing molecule is bound to the third handle domain through the hybridization of the third oligonucleotide to the third handle domain, each one of said effector nucleic acid origami devices or members comprising still a further staple strand positioned on its outer surface, said further staple strand comprising a fourth oligonucleotide selected such that it is capable of hybridizing to said third handle domain of another of said effector nucleic acid origami devices or members, such that the fourth oligonucleotide displaces the third oligonucleotide of said another of said effector nucleic acid origami devices or members, linked to the quorum sensing molecule, thereby releasing said quorum sensing molecule linked to said third oligonucleotide, optionally wherein the released quorum sensing molecule is capable of causing transition of one of said effector nucleic acid origami devices or members from its closed configuration to its open configuration.

19. A pharmaceutical composition comprising a system of claim 1 and a pharmaceutically acceptable carrier.

20. The system of claim 2, wherein each one of said nucleic acid origami devices is methylated at CpG dinucleotides.

21. The system of claim 5, wherein said small molecule is selected from the group consisting of a cyclooxygenase protein capable of binding paracetamol, a sodium channel subunit capable of binding tetrodotoxin and an anti-digoxin antibody capable of binding digoxin.

* * * * *